US008168803B2

(12) United States Patent
Palladino et al.

(10) Patent No.: US 8,168,803 B2
(45) Date of Patent: May 1, 2012

(54) METHODS OF USING [3.2.0] HETEROCYCLIC COMPOUNDS AND ANALOGS THEREOF

(75) Inventors: Michael Palladino, Encinitas, CA (US); Saskia Theodora Cornelia Neuteboom, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 556 days.

(21) Appl. No.: 12/136,688

(22) Filed: Jun. 10, 2008

(65) Prior Publication Data

US 2009/0182027 A1 Jul. 16, 2009

Related U.S. Application Data

(63) Continuation of application No. 10/871,368, filed on Jun. 18, 2004, now abandoned.

(60) Provisional application No. 60/480,270, filed on Jun. 20, 2003, provisional application No. 60/566,952, filed on Apr. 30, 2004.

(51) Int. Cl.
*A61K 31/4015* (2006.01)
*C07D 493/04* (2006.01)
*C07D 498/04* (2006.01)

(52) U.S. Cl. ............... 548/453; 514/211.06; 514/421

(58) Field of Classification Search ............ None
See application file for complete search history.

(56) References Cited

U.S. PATENT DOCUMENTS

| | | | |
|---|---|---|---|
| 5,445,829 A | 8/1995 | Paradissis et al. |
| 5,576,012 A | 11/1996 | Bauer et al. |
| 5,601,845 A | 2/1997 | Buxton et al. |
| 5,641,515 A | 6/1997 | Ramtoola |
| 5,653,987 A | 8/1997 | Modi et al. |
| 5,654,286 A | 8/1997 | Hostetler |
| 5,667,809 A | 9/1997 | Trevino et al. |
| 5,683,676 A | 11/1997 | Akehurst et al. |
| 5,688,529 A | 11/1997 | Lidgate et al. |
| 5,707,615 A | 1/1998 | Cardin et al. |
| 5,707,641 A | 1/1998 | Gertner et al. |
| 5,726,181 A | 3/1998 | Hausheer et al. |
| 5,733,888 A | 3/1998 | Carver et al. |
| 5,756,764 A | 5/1998 | Fenteany et al. |
| 5,874,443 A | 2/1999 | Kiely et al. |
| 5,886,210 A | 3/1999 | Rayle et al. |
| 5,922,683 A | 7/1999 | Or et al. |
| 6,133,308 A | 10/2000 | Soucy et al. |
| 6,147,223 A | 11/2000 | Fenteany et al. |
| 6,214,862 B1 | 4/2001 | Fenteany et al. |
| 6,271,199 B2 | 8/2001 | Brand et al. |
| 6,294,560 B1 | 9/2001 | Soucy et al. |
| 6,333,358 B1 | 12/2001 | Nakazato et al. |
| 6,335,358 B1 | 1/2002 | Fenteany et al. |
| 6,350,759 B1 | 2/2002 | Casara et al. |
| 6,458,825 B1 | 10/2002 | Fenteany et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,566,553 B2 | 5/2003 | Soucy et al. |
| 6,645,999 B1 | 11/2003 | Schreiber et al. |
| 6,794,516 B2 | 9/2004 | Soucy et al. |
| 6,838,477 B2 | 1/2005 | Schreiber et al. |
| 6,849,743 B2 | 2/2005 | Soucy et al. |
| 7,144,723 B2 | 12/2006 | Fenical et al. |
| 7,176,232 B2 | 2/2007 | Fenical et al. |
| 7,176,233 B2 | 2/2007 | Fenical et al. |
| 7,179,834 B2 | 2/2007 | Fenical et al. |
| 7,183,417 B2 | 2/2007 | Corey |
| 7,276,530 B2 | 10/2007 | Potts et al. |
| 7,371,875 B2* | 5/2008 | Xiao et al. ............ 549/510 |
| 7,511,156 B2* | 3/2009 | Corey ............ 548/453 |
| 7,544,814 B2 | 6/2009 | Potts et al. |
| 7,572,606 B1 | 8/2009 | Lam et al. |
| 7,579,371 B2 | 8/2009 | Palladino et al. |
| 7,635,712 B2 | 12/2009 | Fenical et al. |
| 7,879,576 B2 | 2/2011 | Fenical et al. |
| 7,910,616 B2 | 3/2011 | Macherla et al. |
| 7,928,138 B2 | 4/2011 | Fenical et al. |
| 2001/0002391 A1 | 5/2001 | Brand et al. |
| 2001/0051654 A1 | 12/2001 | Elliott et al. |
| 2002/0049157 A1 | 4/2002 | Wu et al. |
| 2002/0106689 A1 | 8/2002 | Faustman et al. |
| 2003/0157695 A1 | 8/2003 | Fenical et al. |
| 2004/0106539 A1 | 6/2004 | Schubert et al. |
| 2004/0138196 A1 | 7/2004 | Fenical et al. |
| 2005/0049294 A1 | 3/2005 | Palladino et al. |
| 2005/0203029 A1 | 9/2005 | Schubert et al. |

(Continued)

FOREIGN PATENT DOCUMENTS

CA 2429163 6/2002

(Continued)

OTHER PUBLICATIONS

The Merck Manual of Diagosis and Therapy, Seventeenth Edition, published 1999 by Merck Research Laboratories, pp. 1085-1088, 1101-1135, 1237-1276.*
Mutomba et al., "Inhibition of proteasome activity blocks cell cycle progression at specific phase boundaries in African trypanosomes" Molecular and Biochemical Parisitology (1997) vol. 90 pp. 491-504.*
Silva-Jardim et al., "The *Leishmania chagasi* proteasome: role in promastigotes growth and amastigotes survival within murine macrophages" Acta Tropica (2004) vol. 91 pp. 121-130.*
Cusack, "Rationale for the treatment of solid tumors with the proteasome inhibitor bortezomib" Cancer Treatment Reviews (2003) vol. 29 suppl. 1, pp. 21-31.*

(Continued)

*Primary Examiner* — Eric S Olson
(74) *Attorney, Agent, or Firm* — Knobbe Martens Olson & Bear LLP

(57) ABSTRACT

Disclosed are methods of treating cancer, inflammatory conditions, and/or infectious disease in an animal comprising: administering to the animal, a therapeutically effective amount of a heterocyclic compound. The animal is a mammal, preferably a human or a rodent.

12 Claims, 31 Drawing Sheets

U.S. PATENT DOCUMENTS

| | | | |
|---|---|---|---|
| 2005/0203162 A1 | 9/2005 | Xiao et al. | |
| 2005/0239866 A1 | 10/2005 | Fenical et al. | |
| 2006/0008852 A1 | 1/2006 | Fenical et al. | |
| 2006/0229353 A1 | 10/2006 | Stadler et al. | |
| 2006/0264495 A1 | 11/2006 | Palladino et al. | |
| 2006/0287520 A1 | 12/2006 | Danishefsky et al. | |
| 2007/0004676 A1 | 1/2007 | Palladino et al. | |
| 2007/0155815 A1 | 7/2007 | Fenical et al. | |
| 2007/0161693 A1 | 7/2007 | Corey | |
| 2007/0225350 A1 | 9/2007 | Anderson et al. | |
| 2007/0249693 A1 | 10/2007 | Ling et al. | |
| 2008/0070273 A1 | 3/2008 | Fenical et al. | |
| 2008/0070969 A1 | 3/2008 | Potts et al. | |
| 2008/0280968 A1 | 11/2008 | Palladino et al. | |
| 2009/0022730 A1 | 1/2009 | Raulf et al. | |
| 2009/0036390 A1 | 2/2009 | Anderson et al. | |
| 2009/0062547 A1 | 3/2009 | Romo et al. | |
| 2009/0069401 A1 | 3/2009 | Fenical et al. | |
| 2009/0148445 A1* | 6/2009 | Bonavida et al. | 424/133.1 |
| 2009/0156469 A1 | 6/2009 | Ghobrial et al. | |
| 2009/0197937 A1 | 8/2009 | Fenical et al. | |
| 2009/0234137 A1 | 9/2009 | Ling et al. | |
| 2009/0298906 A1 | 12/2009 | Macherla et al. | |
| 2009/0318529 A1 | 12/2009 | Fenical et al. | |
| 2010/0144826 A1 | 6/2010 | Fenical et al. | |
| 2010/0168046 A1 | 7/2010 | Palladino et al. | |

FOREIGN PATENT DOCUMENTS

| | | |
|---|---|---|
| EP | 2088205 | 8/2009 |
| WO | WO 94/17816 | 8/1994 |
| WO | WO 96/32105 | 10/1996 |
| WO | WO 98/35691 | 8/1998 |
| WO | WO 98/41648 | 9/1998 |
| WO | WO 99/09006 | 2/1999 |
| WO | WO 99/15183 | 4/1999 |
| WO | WO 99/22729 | 5/1999 |
| WO | WO 00/23614 | 4/2000 |
| WO | WO 00/33654 | 6/2000 |
| WO | WO 02/47610 | 6/2002 |
| WO | WO 2004/043374 A | 11/2003 |
| WO | WO 2004/004749 | 1/2004 |
| WO | WO 2004/071382 | 8/2004 |
| WO | WO2004/071382 * | 8/2004 |
| WO | WO 2005/002572 | 1/2005 |
| WO | WO 2005/003137 | 1/2005 |
| WO | WO 2006/028525 | 3/2005 |
| WO | WO 2005/094423 | 10/2005 |
| WO | WO 2005/099687 | 10/2005 |
| WO | WO 2006/005551 | 1/2006 |
| WO | WO 2006/060609 | 6/2006 |
| WO | WO 2006/060676 | 6/2006 |
| WO | WO 2006/060809 | 6/2006 |
| WO | WO 2006/099261 | 9/2006 |
| WO | WO 2006/118973 | 11/2006 |
| WO | WO 2007/021897 | 2/2007 |
| WO | WO 2007/033039 | 3/2007 |
| WO | WO 2007/104537 | 9/2007 |
| WO | WO 2007/130404 | 11/2007 |
| WO | WO 2007/138116 | 12/2007 |
| WO | WO 2008/124699 | 10/2008 |
| WO | WO 2008/137780 | 11/2008 |
| WO | WO 2009/101083 | 8/2009 |
| WO | WO 2009/134531 | 11/2009 |
| WO | WO 2009/140287 | 11/2009 |

OTHER PUBLICATIONS

Feling et al., "Salinosporamide A: A Highly Cytotoxic Proteasome Inhibitor from a Novel Microbial Source, a Marine Bacterium of the New Genus *Salinospora*" Angew. Chem. Int. Ed. (2003) vol. 42 No. 3, pp. 355-357.*

Newton. "Il fondo agli oceani potenti antibiotici e anticancro." www.newton.rcs.it/PrimoPiano/News/2003/02_Febbraio/03/Antobiotico.html. (Feb. 2, 2003) XP002304843.

Ciechanover, et al., (Eds.) "The Ubiquitin-Proteasome Proteolytic System—From Classical Biochemistry to Human Diseases" by Baumeister et al., (2002) pp. 68-70.

Online www.netdoctor.co.uk "Isoniazid: Treatment of Tuberculosis", [accessed on Apr. 8, 2008] pp. 1-2.

Pieters et al., "Microbiology: Chemical Warfare and Mycobacterial Defense", *Science*, (Dec. 2003) 302:1900-1902.

Stella et al., (Ed.), "Prodrugs: Challenges and Rewards, Part 1", American Association of Pharma. Scientists (2007), p. 24.

International Search Report and Written Opinion dated Nov. 29, 2004 in International Application No. PCT/US2004/019453; International Filing Date: Jun. 18, 2004.

International Preliminary Report on Patentability dated Mar. 14, 2005 in International Application No. PCT/US2004/019453, International Filing Date: Jun. 18, 2004.

International Search Report and Written Opinion dated Dec. 29, 2006 in International Application No. PCT/US2005/014846; International Filing Date: Apr. 29, 2005.

International Preliminary Report on Patentability dated Jan. 23, 2007 in International Application No. PCT/US2005/014846, International Filing Date: Apr. 29, 2005.

International Search Report dated Aug. 2, 2002 in International Application No. PCT/US01/043758, International Filing Date Nov. 16, 2001.

International Preliminary Report on Patentability dated Aug. 24, 2004 in International Application No. PCT/US2001/043758, International Filing Date: Nov. 16, 2001.

International Search Report and Written Opinion dated Feb. 27, 2007 in International Application No. PCT/US06/016104, International Filing Date: Apr. 27, 2006.

International Preliminary Report on Patentability dated Oct. 30, 2007 in PCT/US2006/016104, International Filing Date Apr. 27, 2006.

International Search Report and Written Opinion dated Jan. 29, 2009 in International Application No. PCT/US2008/062553, filed May 2, 2008.

U.S. Appl. No. 11/966,801, filed Dec. 28, 2007.

Office Action dated Apr. 17, 2009 in U.S. Appl. No. 12/114,449, filed May 2, 2008.

Johnson et al., "Relationships between drug activity in NCI preclinical in vitro and in vivo models and early clinical trials", *British J Cancer*, (2001) 84(11): 1424-1431.

NCI/NIH Developmental Therapeutic Program, "Cell Lines in the in Vitro Screen", online: http://dtp.nci.nih.gov/docs/misc/common_files/cell_list/html, accessed Oct. 27, 2009.

Reed et al., "Salinosporamides D-J from the Marine Actinomycete *Salinispora tropica*, Bromosolinosporamide, and Thioester Derivatives Are Potent Inhibitors of the 20S Proteasome", *J Nat Prod.*, (2007) 70: 269-276.

Sausville et al., "Contributions of human tumor xenografts to anticancer drug development", *Cancer Res.* (2006) 66(7): 3351-3354.

International Preliminary Report on Patentability dated Nov. 19, 2009 in International Application No. PCT/US2008/062553, filed May 2, 2008.

Final Office Action in U.S. Appl. No. 11/841,588, Dated Aug. 6, 2009.

Notice of Allowance in U.S. Appl. No. 11/841,588, Dated Mar. 1, 2010.

Office Action in U.S. Appl. No. 11/966,787, Dated Apr. 22, 2009.

Office Action in U.S. Appl. No. 11/966,787, Dated Nov. 5, 2009.

Office Action in U.S. Appl. No. 11/966,801, Dated Nov. 2, 2009.

Office Action in U.S. Appl. No. 12/114,449, Dated Dec. 10, 2009.

Corey, et al., "Total Synthesis of Lactacystin," *J. Am. Chem. Soc.*, (1992) 114(26):10677-10678.

Corey, et al., "An Efficient Total Synthesis of a New and Highly Active Analog of Lactacystin," *Tetrahedron Letters*, (1998) 39:7475-7478.

Ding, et al., "Proteasome Inhibition Induces Reversible Impairments in Protein Synthesis," *The FASEB Journal.*, (2006) 20:1055-1063.

Donauer et al. "Expression Profiling on Chronically Rejected Transplant Kidneys." *Transplantation* (2003) 76:539-547.

Hogan, et al., "Proteasome Inhibition by a Totally Synthetic β-Lactam Related to Salinosporamide A and Omuralide," *J. Am. Chem. Soc.*, (2005) 127(44):15386-15387.

Kisselev et al., "Importance of the Different Proteolytic Sites of the Proteasome and the Efficacy of Inhibitors Varies with the Protein Substrate," J Bio Chem., (Mar. 2006) 281(13): 8582-8590.

Lenz, et al., "Clinical Update: Proteasome Inhibitors in Solid Tumors", *Cancer Treatment Reviews*, (2003) 29 (1 Supplement):41-48.

Luo, Hongyu. "A Proteasome Inhibitor Effectively Prevents Mouse Heart Allograft Rejection." *Transplantation* (2001) 72(2):196-202.

Manchand, et al., "Syntheses of the Anti-AIDS Drug 2',3'-Dideoxycytidine from Cytidine," *J. Org. Chem.*, (1992) 57:3473-3478.

Mateos-Mazon et al. "Use of bortezomib in the management of chronic graft-versus-host disease among multiple myeloma patients relapsing after allogenic transplantation." *Haematologica* (2007) 92:1295-1296.

Mattingly et al. "Use of Systemic Proteasome Inhibition as an Immune-Modulating Agent in Disease." *Endocrine, Metabolic & Immune Disorders—Drug Targets* (2007) 7:29-34.

Merriam-Webster Online Dictrionary, "Heteroatom", 2010, Merriam-Webster Online, accessed Jun. 16, 2010, http://merriam-webster.com/dictionary/heteroatom.

Momose, et al., "2(3H)-and 2(5H)-Furanones. VII. Chirality Transfer on the Tetronic Acid Templates," *Heterocycles*, (1999) 51(6):1321-1343.

Online URL:http://aidsinfo.nih.gov/DrugsNew/DrugDetailNT.aspx?MenuItem=Drugs&Search=On&int_id=244; pp. 1-2, downloaded Nov. 22, 2010.

Online URL:http://web.archive.org/web/20060117081111/hivhep.tempdomainname.com/hiv and aids/norvir effects . . . Nov. 22, 2010. 1 page.

Rockwell, et al., "Proteasome Inhibition in Neuronal Cells Induces a Proinflammatory Response Manifested by Upregulation of Cyclooxygenase-2, Its Accumulation as Ubiquitin Conjugates, and Production of the Prostaglandin $PGE_2$," *Arch. Biochem. and Biophysics*, (2000) 374(2):325-333.

Saravanan, et al., "A Short, Stereocontrolled, and Practical Synthesis of α-Methylomuralide, a Potent Inhibitor of Proteasome Function," *J. Org. Chem.*, (2003) 68(7):2760-2764.

Tabuchi, et al., "Application of 'Proteasome Tolerance' to Therapies for Neurodegenerative Disease," *Alzheimer's and Dementia*, (2006) 2(3) (1 Supplement):S628.

Yew, et al., "Proteasome Inhibition by Lactacystin in Primary Neuronal Cells Induces Both Potentially Neuroprotective and Pro-Apoptotic Transcriptional Responses: a Microarray Analysis," *J. Neurochem.*, (2005) 94(4):943-956.

International Search Report and Written Opinion dated Sep. 28, 2009 for International Application No. PCT/US2009/043644, International Filing Date: May 12, 2009.

International Preliminary Report on Patentability (Chapter II) dated Aug. 6, 2010 for International Application No. PCT/US2009/043644, International Filing Date: May 12, 2009.

International Search Report and Written Opinion dated May 12, 2006 in International Application No. PCT/US2005/043668, International Filing Date: Dec. 2, 2005.

International Preliminary Report on Patentability dated Jun. 14, 2007 in International Application No. PCT/US2005/043668, International Filing Date: Dec. 2, 2005.

International Search Report and Written Opinion dated Nov. 15, 2005 in International Application No. PCT/US2005/012218, International Filing Date: Apr. 11, 2005.

International Preliminary Report on Patentability dated Oct. 11, 2006 in International Application No. PCT/US2005/012218, International Filing Date: Apr. 11, 2005.

International Search Report and Written Opinion dated Oct. 19, 2005 in International Application No. PCT/US2005/012113, International Filing Date: Apr. 11, 2005.

International Preliminary Report on Patentability dated Oct. 11, 2006 in International Application No. PCT/US2005/012113, International Filing Date: Apr. 11, 2005.

International Search Report and Written Opinion dated Jan. 10, 2007 in International Application No. PCT/US2006/031314, International Filing Date: Aug. 10, 2006.

International Preliminary Report on Patentability dated Feb. 12, 2008 in International Application No. PCT/US2006/031314, International Filing Date: Aug. 10, 2006.

International Search Report and Written Opinion dated Aug. 3, 2007 in International Application No. PCT/US2006/035196, International Filing Date: Sep. 8, 2006.

International Preliminary Report on Patentability dated Mar. 18, 2008 in International Application No. PCT/US2006/035196, International Filing Date: Sep. 8, 2006.

EFS File History of U.S. Appl. No. 10/871,368, filed Mar. 3, 2005.

EFS File History of U.S. Appl. No. 11/118,260, filed Apr. 29, 2005.

EFS File History of U.S. Appl. No. 09/991,518, filed Nov. 16, 2001.

EFS File History of U.S. Appl. No. 11/228,416, filed Sep. 15, 2005.

EFS File History of U.S. Appl. No. 11/841,588, filed Aug. 20, 2007 as of Aug. 4, 2010.

EFS File History of U.S. Appl. No. 11/966,787, filed Dec. 28, 2007 as of Jun. 28, 2010.

EFS File History of U.S. Appl. No. 11/966,801, filed Dec. 28, 2007 as of Aug. 2, 2010.

EFS File History of U.S. Appl. No. 10/600,854, filed Jun. 20, 2003.

EFS File History of U.S. Appl. No. 10/838,157, filed Apr. 30, 2004.

EFS File History of U.S. Appl. No. 11/147,622, filed Jun. 7, 2005.

EFS File History of U.S. Appl. No. 11/705,694, filed Feb. 12, 2007.

EFS File History of U.S. Appl. No. 12/638,860, filed Dec. 15, 2009.

EFS File History of U.S. Appl. No. 11/412,476, filed Apr. 27, 2006.

EFS File History of U.S. Appl. No. 11/865,704, filed Oct. 1, 2007.

EFS File History of U.S. Appl. No. 11/453,374, filed Jun. 15, 2006.

EFS File History of U.S. Appl. No. 12/114,449, filed May 2, 2008.

EFS File History of U.S. Appl. No. 12/464,686, filed May 12, 2009.

EFS File History of U.S. Appl. No. 11/293,354, filed Dec. 2, 2005.

EFS File History of U.S. Appl. No. 12/183,007, filed Jul. 30, 2008 as of Nov. 9, 2010.

EFS File History of U.S. Appl. No. 10/821,621, filed Apr. 9, 2004.

EFS File History of U.S. Appl. No. 11/539,648, filed Oct. 9, 2006.

EFS File History of U.S. Appl. No. 12/028,024, filed Feb. 8, 2008.

EFS File History of U.S. Appl. No. 11/224,589, filed Sep. 12, 2005.

Beers, et al. (Eds), "The Merck Manual of Diagnosis and Therapy", 17th Ed., The Merck Research Laboratories, Whitehouse Station N.J., (1999): 1085-1088, 1101-1135, and 1237-1276.

Brosius, et al., "Complete nucleotide sequence of a 16S ribosomal RNA gene from *Eschericia coli*," *Biochemistry*, (1978) 75(10)4801-4805.

Chauhan, et al., "A Novel Orally Available Proteasome Inhibitor NPI-0052 Induces Killing in Multiple Myeloma (MM) Cells Resistant to Conventional and Bortezomib Therapies," *Blood*, (2004) 104(11): 2405.

Cole, et al., "The Ribosomal Database Project (RDP-II): sequences and tools for high-throughput rRNA analysis," *Nucleic Acids Research*, (2005) 33: D294-D296.

Fenical, et al., "Discovery and Development of the Anticancer Agent Salinosporamide A (NPI-0052)," *Bioorganic & Med. Chem.*, (2009) 17:2175-2180.

Fingl, et al., "General Principals," *The Pharmaceutical Basis of Therapeutics*, 5th Ed., (Goodman et al. Eds., 1975), MacMillan Publishing Co. Inc., New York, Chapter 1:1-46.

Gale, et al. (Eds.), *The Molecular Basis of Antibiotic Action*, 2nd ed., John Wiley and Sons, London (1981) Table of Contents, pp. 1-13.

Jensen, et al., "Marine Microorganisms and Drug Discovery: Current Status and Future Potential," *Drugs from the Sea*, Nobuhiro Fusetani Ed., *Krager*, Basel Switzerland (2000) 6-29.

Manam, et al., Leaving Groups Prolong the Duration of 20S Proteasome Inhibition and Enhance the Potency of Salinosporamide, *J Med Chem.*, (2008) 51(21): 6711-6724.

EFS File History of U.S. Appl. No. 11/841,588, filed Aug. 20, 2007.

EFS File History of U.S. Appl. No. 11/966,787, filed Dec. 28, 2007.

EFS File History of U.S. Appl. No. 11/966,801, filed Dec. 28, 2007 as of Mar. 24, 2011.

EFS File History of U.S. Appl. No. 12/638,860, filed Dec. 15, 2009 as of May 16, 2011.

EFS File History of U.S. Appl. No. 12/183,007, filed Jul. 30, 2008 as of Jun. 6, 2011.

Adams, Julian, "Proteasome Inhibitors as New Anticancer Drugs", *Curr. Opin. Oncol.*, (2002) 14:628.

Adams, et al., "Proteasome Inhibitors: A Novel Class of Potent and Effective Antitumor Agents", *Cancer Res.*, (1999) 59:2615.

Adams, J., "The Development of Novel Targeted Therapeutics for Treatment of Multiple Myeloma Research Roundtable", *Euro. J. Haematology*, (2003) 70:263-272.

Alessandri, et al., "Mobilization of Capillary Endothelium in Vitro Induced by Effectors of Angiogenesis in Vivo", *Cancer Res.*, (1983) 43(4):1790-1797.

Alm, et al., "Effects of Topically Applied PGF2 and its Isopropylester on Normal and Glaucomatous Human Eyes", *Prog. Clin. Biol. Res.*, (1989) 312:447-58.

Beers et al., "The Merck Manual of Diagnosis and Therapy," 17th Ed. 1999, published by Merck Research Laboratories, pp. 397-398, 948-949, 1916 and 1979-1981.

Beers, et al., "Bacterial Diseases" *The Merck Research Laboratories*, Whitehouse Station N.J. XP002318189 157(13): 1157-1158, (1999).

Beers, et al., "Parasitic Infections" *Merck Research Laboratories*, Whitehouse Station N.J. XP002318189. 1241-1252, (1999).

Bernan, et al., "Marine Microorganisms as a Source of New Natural Products", *Advances in Applied Microbiology*, (1997) 43:57-90.

Bhalla, et al., "High-Dose Mitoxantrone Induces Programmed Cell Death or Apoptosis in Human Myeloid Leukemia Cells", *Blood*, (1993) 82(10):3133-3140.

Bicknell, et al., "Tumour Angiogenesis", *Oxford University Press*, New York (1997) pp. 5 Content.

Blum, et al., "Adriamycin: A New Anticancer Drug with Significant Clinical Activity", *Ann Intern Med*, (1974) 80:249-59.

Blunt, et al., "Marine Natural Products", *Nat. Prod. Rep.*, (2003) 20:1-48.

Bodart, et al., "Anthrax, MEK and Cancer", *Cell Cycle*, (2002) 1:10-15.

Bradley, et al., "Identification of the Cellular Receptor for Anthrax Toxin", *Nature*, (2001) 414:225-9.

Bull, et al., "Search and Discovery Strategies for Biotechnology: the Paradigm Shift", *Microbiol Mol. Biol. Rev.*, (2000) 64:573-606.

Carey, Francis, "Organic Chemistry", 2d ed., McGraw Hill, Inc., New York (1992) 328-331.

Chauhan, et al., "A Novel Orally Active Proteasome Inhibitor Induces Apoptosis in Multiple Myeloma Cells with Mechanisms Distinct from Bortezomib", *Cancer Cell*, (2005) 8:407-19.

Chauhan, et al., "A Novel Proteasome Inhibitor NPI-0052 as an Anticancer Therapy," *British Journal of Cancer*, (2006) 95(8):961-965.

Cheng, et al., "Arenaric Acid, a New Pentacyclic Polyether Produced by a Marine Bacterium (Actinomycetales)", *J. Natural Products*, (1999) 62:605-607.

Cheng, et al., "Luisols A and B, New Aromatic Tetraols Produced by an Estuarine Marine Bacterium of the Genus *Streptomyces* (Actinomycetales)", *J. Natural Products*, (1999) 62:608-610.

Claverol, et al., "Mapping and Structural Dissection of Human 20 S Proteasome Using Proteomic Approaches", *Mol Cell Proteomics*, (2002) 1:567-78.

Colquhoun, et al, "Rapid Characterization of Deep-Sea Actionmycetes for Biotechnology Screening Programmes", *Antonie Van Leeuwenoek*, Dordrecht, (2000) 77:359-367.

Colquhoun, et al., "Novel *Rhodococci* and Other Mycolate Actinomycetes From the Deep Sea", *Antonie van Leeuwenhoek*, (1998) 74:27-40.

Colquhoun, et al., "Taxonomy and Biotransformation Activites of Some Deep-Sea Actinomycetes", *Extremophiles*, (1998) 2:269-277.

Crane, et al., "A Novel Enantioselective Synthetic Route to Omuralide Analogues with the Potential for Species Selectivity in Proteasome Inhibition", *Organic Letters*, (2001) 1395-1397.

Cragg, et al. "Chemical Diversity: A Function of Biodiversity", *Trends Pharmacol Sci*, (2002) 23:404.

Crueger, et al., "Biotechnology: A Textbook of Industrial Microbiology", 2nd ed., *Science Tech Publishers*, (1989) Chapter 2:5-8.

Cusak, et al., "Enhanced Chemosensitivity to CPT-11 with Proteasome Inhibitor PS-341: Implications for Systemic Nuclear Factor-kB Inhibition", *Cancer Res.*, (2001) 61:3535-64.

Cusak, et al., NPI-0052 Enhances Tumoricidal Response to Conventional Cancer Therapy in a Colon Cancer Model, *Clin Cancer Res.*, (2006) 22:6758-64.

Davidson, Bradley S., "New Dimensions in Natural Products Research: Cultured Marine Microorganisms", *Current Opinion in Biotechnology*, (1995) 6:284-291.

Decker, et al., "Inhibition of Caspase-3-mediated Poly (ADP-ribose) Polymerase (PARP) Apoptotic Cleavage by Human PARP Autoantibodies and Effect on Cells Undergoing Apoptosis", *J. Biol. Chem.*, (2000) 275(12):9043-9046.

Delong, et al. "Environmental Diversity of Bacteria and Archaea", *Syst. Biol.*, (2001) 50(4):470-478.

Dick, et al., "Mechanistic Studies on the Inactivation of the Proteasome by Lactacystin", *J Biol Chem.*, (1996) 271(13):7273-76.

"DTP Human Tumor Cell Line Screen." Screening Services. DPI. Sep. 28, 2005 http://dtp.nci.nih.gov/branches/btb/ivclsp.html.

Duesbery, et al., "Proteolytic Inactivation of MAP-Kinase-Kinase by Anthrax Lethal Factor", *Science*, (1998) 280:734-7.

Elliott, et al., "Proteasome Inhibition: A New Anti-Inflammatory Strategy", *J Mol Med*, (2003) 81:235-245.

Elliot, et al., "The Proteasome: A New Target for Novel Drug Therapies", *American Journal of Clinical Pathology*, (2001) 637-646.

Erba, et al., "Mode of Action of Thiocoraline:A Natural Marine Compound With Anti-Tumor Activity", *British Journal of Cancer*, (1999) 88(7):971-980.

Escuyer, et al., "Anthrax Protective Antigen Interacts with a Specific Receptor on the Surface of CHO-K1 Cells", *Infect Immun.*, (1991) 59(10):3381-6.

Faulkner, D.J., "Marine Natural Products", *Nat Prod Rep*, (2001) 18:1-49.

Feling, et al. "Salinosporamide A: A Highly Cytotoxic Proteasome Inhibitor from a Novel Microbial Source, a Marine Bacterium of the New Genus Salinospora", *Angew. Chem. Int. Ed.*, (2003) 42(3):355-357.

Fenical, et al., "Marine Microorganisms as a Developing Resource for Drug Discovery", *Pharmaceutical News*, (2002) 489-494.

Fenical, et al., "Marine Microorganisms as a Biomedical Source: Are they unculturable or Uncultured?", PowerPoint Presentation, Center for Marine Biotechnology and Biomedicine (Feb. 24, 2002).

Fenical, et al., "Marine Microorganisms as a Developing Resource for Drug Discovery", *Pharmaceutical New*, (2002) 9:489-494.

Fenical, et al., "Salinospora, a Major New Marine Actinomycete Taxon for Drug Discovery", Powerpoint Presentation, Center for Marine Biotechnology and Biomedicine (Jun. 24, 2001).

Fenical, William, "Chemical Studies of Marine Bacteria: Developing a New Resource", *Chem Review*, (1993) 93:1673-1683.

Fenical, William, "New Pharmaceuticals From Marine Organisms", *Marine Biotechnology*, (1997) 15:339-341.

Fenteany, et al., "Inhibition of Proteasome Activities and Subunit-Specific Amino-Terminal Threonine modification by Lactacystin", *Science*, (1995) 268:726-73.

Fenteany, et al., "Lactacystin, Proteasome Function, and Cell Fate," *J. Biol. Chem.* (1998) 273:8545.

Fernandez-Chimeno, et al., "IB-96212, a Novel Cytotoxic Macrolide Produced by a Marine *Micromonospora*", *Journal of Antibiotics*, (2000) 53(5):474-478.

Folkman, Judah, "Tumor Angiogenesis", *Adv Cancer Res.*, (1985) 43:175-203.

Folkman, Judah, "Angiogenesis-Dependent Diseases", *Seminars in Oncology*, (Dec. 2001) 28:536-42.

Fukuchi, et al., "Direct Proteasome Inhibition by Clasto-Lactacystin B-Lactone Permits the Detection of Ubiquitinated p21 in ML-1 Cells", *Biochem Biophys Acta*, (1999) 1451:206-210.

Fusetani, Nobuhiro, "Marine Microorganisms and Drug Discovery: Current Status and Future Potential," *Drugs from the Sea*, Krager, Basel, CH (2000), 6-29.

Gantt, et al., "Proteasome Inhibitors Block Development of Plasmodium SPP", *Antimicrobial Agents and Chemotherapy*, (1998) 2731-2738.

Geier, et al., "A Giant Protease with Potential to Substitute for Some Functions of the Proteasome", *Science*, (1999) 283:978-81.

Giovannoni, Stephen, "Oceans of Bacteria", *Nature*, (Jul. 29, 2004) 430:515-516.

Goldberg, et al., "Not Just Research Tools—Proteasome Inhibitors Offer Therapeutic Promise", *Natural Medicine*, (2002) 338-340.

Golub, et al., "Molecular Classification of Cancer; Class Discovery and Class Prediction by Gene Expression Monitoring", *Science*, (1999) 286:531-537.

Goodfellow, et al., "Actinomycetes in Biotechnology", Okami, et al., ed., *Search and Discovery of New Antibiotics*. Academic Press: San Diego, (1988), 33-67.

Goodfellow, et al., "Actinomycetes in Marine Sediments", *Biological Biochemical and Biomedical Aspects of Actinomycetes*, Academic Press, Inc., Orlando (1984) 453-472.

Goodfellow, et al., "Ecology of Actinomycestes", *Ann. Rev. Microbiol.*, (1983) 37:189-216.

Goodfellow, et al., "Search and Discovery of Industrially Significant Actinomycetes", *Microbial Products: NewAapproaches, Society for General Microbiology Symposium*, (1989) 44:343-383.

Grant, et al., "Intracellular Mechanisms Involved in Basement Membrane Induced Blood Vessel Differentiation in Vitro", *In Vitro Cell Dev. Biol.*, (1991) 27A:327-336.

Grosios, et al., "Angiogenesis Inhibition by the Novel VEGF Receptor Tyrosine Kinase Inhibitor; PTK787/ZK222584, Causes Significant Anti-Arthritic Effects in Models Of Rheumatoid Arthritis", *Inflamm Res*, 53, (2004) 133-142.

Hanna, et al., "On the Role of Macrophages in Anthrax", *Proc Natl Acad Sci USA*, (1993) 90:10198-10201.

Hardt, et al., "Neomarinone, and New Cytotoxic Marinone Derivatives, Produced by a Marine Filamentous Bacterium (Actinomycetales)", *Tetrahedron Letters*, (2000) 41(13):2073-2076.

Harker, et al., "Multidrug Resistance in Mitoxantrone-Selected HL-60 Leukemia Cells in the Absence of P-Glycoprotein Overexpression", *Cancer Res.*, (1989) 15:4542-4549.

He, et al., "Lomaiviticins A and B, Potent Antitumor Antibiotics from *Micromonospora iomaivitiensis*", *J. Am. Chem. Soc.*, (2001) 123:5362-5363.

Helmke, et al., "*Rhodococcus marinonascens* sp. nov.: An Actinomycete From the Sea", *International J. of Systematic Bacteriology*, (Apr. 1984) 34(2):127-128.

Hideshima, et al., "NF-κB as a Therapeutic Target in Multiple Myeloma," *J. Biol. Chem.*, (2002) 277(19):16639-16647.

Higuchi, et al., "Pro-Drugs as Novel Delivery Systems", vol. 14, A.C.S. Symposium Series *American Chemical Society*, Atlantic City, NJ., Sep. 10, 1974, (1975) pp. 3 Content.

Hopwood, et al., "Genetic Manipulation of *Streptomyces* Polyketide Synthase Genes for Novel Secondary Metabolite Production", *FEMS Microbiology Reviews*, (1995) 16:233-234.

Horan, Ann C., "Aerobic Actinomycetes: A Continuing Source of Novel Natural Products" Chapter 1 In *The Discovery of natural products with Therapeutic Potential*, Biotechnology (1994) 1-30.

Hull, et al., "Antiangiogenic Agents Are Effective Inhibitors of Endometriosis." *J Clinical Endocrinology Metabolism*, (2003) 88:2889-2899.

Jensen, et al., "Strategies for the Discovery of Secondary Metabolites from Marine Bacteria: Ecological Perspectives", *Annu. Rev. Microbiology*, (1994) 48:559-584.

Jensen, et al., "Distribution of Actinomycetes in Near-Shore Tropical Marine Sediments", *Applied and Environmental Microbiology*, (Apr. 1991) 57(4):1102-1108.

Jensen, et al., "The Relative Abundance and Seawater Requirements of Gram-Positive Bacteria in Near-Shore Tropical Marine Samples", *Microbial Ecology*, (1995) 29(3):249-257.

Jiang, et al., "Antinoflavoside, A Novel Flavonoid-Like Glycoside Produced by a Marine Bacterium of the Genus *Streptomyces*", *Tetrahedron Letters*, (1997) 38(29):5065-5068.

Joseph, et al., "Laboratory Cultivation of Widespread and Previously Uncultured Soil Bacteria", *Applied and Environmental Microbiology*,(2003) 69(12):7210-7215.

Joshi, A., "Microparticulates for Ophthalmic Drug Delivery", *J Ocul Pharmacol*, (1994) 10:29-45.

Kalns, et al., "TNF Receptor 1, IL-1 Receptor, and iNOS Genetic Knockout Mice Are Not Protected from Anthrax Infection", *Biochem Biophys Res Commun.*, (2002) 292:41-44.

Kalns, et al., "Delayed Treatment With Doxycycline Has Limited Effect on Anthrax Infection in BLK57/B6 Mice", *Biochem Biophys Res Commun.*, (2002) 297:506.

Kerr, et al., "Marine Natural Products as Therapeutic Agents", *Exp. Opinion on Therapeutic Patents*, (1999) 9:1207-1223.

Kim, et al., "Sensitizing Anthrax Lethal Toxin-Resistant Macrophages to Lethal Toxin-Induced Killing by Tumor Necrosis Factor", *J Biol Chem*, (2003) 278:7413-21.

King, et al., "How Proteolysis Drives the Cell Cycle", *Science*, (1996) 274:1652-59.

Kisselev, et al., "Proteasome Inhibitors: From Research Tools to Drug Candidates", *Chem Biol*, (2001) 8:739-758.

Koch, et al., "16S Ribosomal DNA Analysis of The Genera *Micromonospora*, *Actinoplanes*, *Catellatospora*, *Catenuloplanes*, *Dactylosporangium*, and *Pillimelia* and Emendation or the Family Micromonosporaceae", *Intl Journal of Systematic Bacteriology*, (Jul. 1996) 46(3):765-768.

Kozlowski, et al., "Lactacystin Inhibits Cathepsin A Activity in Melanoma Cell Lines", *TumorBiology*, (2001) 22:211-215.

Lacy, et al., "Mapping the Anthrax Protective Antigen Binding Site on the Lethal and Edema Factors", *J Biol Chem*, (2002) 277:3006-3011.

Lam, et al., "Isolation of a Bromo Analog of Rebeccamycin From *Saccharothrix aerocolonigenes*", *J of Antibiotics*, (Sep. 1991) 44(9):934-939.

Lam, et al., "Production, Isolation and Structure Determination of Novel Fluoroindolocarbazoles from *Saccharothrix aerocolonigenes* ATCC 39243", *J of Antibiotics*, (2001) 54(1):1-9.

Lawley, et al., "Induction of Morphologic Differentiation of Endothelial Cells in Culture", *J Investigative Dermatology*, (Aug. 1989) 93(2 Supplement):59S-61S.

Lightcap, et al., "Proteasome Inhibition Measurements Clinical Application", *Clin Chem*, (2000) 46(5):673-683.

Lin, et al., "Cytotoxic Effects of Anthrax Lethal Toxin on Macrophage-Like Cell Line J774A.1", *Curr Microbiol*, (1996) 33:224-227.

Liu, et al., "Precursor Supply for Polyketide Biosynthesis: The Role of Crotonyl-CoA Reductase", *Metab Eng*, (2001) 3:40-48.

Liu, et al., "Angiogenesis Inhibitors May Regulate Adiposity", *Nutr Rev*, (2003) 61:384-387.

Macherla, et al., "Structure-Activity Relationship Studies of Salinosporamide A (NPI-0052), a Novel Marine Derived Proteasome Inhibitor", *J Med Chem*, (2005) 48:3684-7.

Mayer, et al., "Efficacy of a Novel Hydrogel Formulation in Human volunteers", *Ophthalmologica*, (1996) 210(2):101-103.

Mayer, et al., "Marine Pharmacology in 1999: Antitumor and Cytotoxic Compounds." *Anticancer Res.*, (2001) 21:2489-2500.

McMurry, John, *Organic Chemistry*, 5th ed., Brooks/Cole, Pacific Grove, CA. (2000) 398-408.

Meng, et al., "Eponemycin Exerts its Antitumor Effect Through the Inhibition of Proteasome Function," *Cancer Res.*, (1999), 59(12):2798-2801.

Meng, et al., "Epoxomicin, a Potent and Selective Proteasome Inhibitor, Exhibits in Vivo Anti-Inflammatory Activity", *Proc. Natl. Acad. Sci.*, (Aug. 1999) 96:10403-10408.

Min, et al., "Urokinase Receptor Antagonists Inhibit Angiogenesis and Primary Tumor Growth in Syngeneic Mice", *Cancer Res.*, (May 15, 1996) 56(10):2428-2433.

Mincer, et al., "Widespread and Persistent Populations of a Major New Marine Actinomycete Taxon in Ocean Sediments", *Applied and Environmental Microbiology*, (Oct. 2002) 68(10):5005-5011.

Mogridge, et al., "Stiochiometry of Anthrax Toxin Complexes", *Biochemistry*, (2002) 41:1079-1082.

Moore, B.S., "Biosynthesis of Marine Natural Products: Microorganisms and Macroalgae", *Nat Prod Rep.* (1999) 16(6):653-674.

Mordenti, et al., "Intracular Pharmacokinetics and Safety of a Humanized Monoclonal Antibody in Rabbits after Intravitreal Administration of a Solution or a PLGA Microsphere Formulation", *Toxicol. Sci.*, (1999) 52(1):101-106.

Moran, et al., "Evidence for Indigenous Streptomyces Populations in Marine Environment Determined with a 16S rRNA Probe" *Applied and Environmental Microbiology*, (Oct. 1995) 61(10):3695-3700.

Mousa, et al., "Angiogenesis Inhibitors: Current & Future Directions", *Current Pharmaceutical Design*, (2004) 10:1-9.

Mulholland et al., "A Concise Total Synthesis of Salinosporamide A," *Org. Biomol. Chem.*, 2006, 4, 2845-6.

Murray, J. Clifford, Angiogenesis Protocols (Methods in Molecular Medicine), *Humana Press*, Totowa, NJ. (2001) Index 4 pages.
NCBI website, sequence for EF105548, http://www.ncbi.nlm.nih.gov/entrez/viewer.fcgi?db=nucleotide&val=118640518, 2 pages, downloaded Feb. 15, 2007, 2 pages.
NCBI website, sequence for AB242910, http://www.ncbi.nlm.nih.gov/entrez/viewer.fcgi?db=nucleotide&val=124300751, 2 pages, downloaded Feb. 15, 2007, 2 pages.
NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.
Nesterneko, et al., "*Rhodococcus luteus* nom. nov., and *Rhodococcus maris* nom. nov.", *Int'l Journal of Systematic Bacteriology*, (Jan. 1982) 32(1):1-14.
Newton. "Il fondo agli oceani potenti antibiotici e anticancro." www.newton.rcs.it/PrimoPiano/News/2003/02_Febbraio/03/Antobiotico.html. (Feb. 2, 2003) 1 page, XP002304843.
Nicholson, D.W., "ICE/CED 3-Like Proteases as Therapeutic Targets for the Control of Inappropriate Apoptosis", *Nat Biotechnology*, (1996) 14:297-301.
Nicosia, et al., "Growth of Microvessels in Serum-Free Matrix Culture of Rat Aorta: A Quantitative Assay of Angiogenesis In Vitro," *Laboratory Investigation*, (Jul. 1990) 63(1):115-122.
Nicolaus B.J. R. "Symbiotic Approach to Drug Design", *Decision Making in Drug Research*, (1983) 173-189 XP002197412.
Nolan, et al., "Isolation and Screening of Actinomycetes", *Actinomycetes in Biotechnology*, (1988), Chapter 1:1-32.
O'Donnel, Anthony G., "Recognition of Novel Actinomycetes", *Actinomycetes in Biotechnology, Academic Press* (1988) Chapter 3:69-88.
Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells", *Cancer Letters*, (1991) 59:57-66.
Okami, et al., "Search and Discovery of New Antibiotics", *Actinomycetes in Biotechnology, Academic Press* (1988)Chapter 2:33-67.
Okami, Y., "The Search for Bioactive Metabolites from Marine Bacteria", *J. Marine Biotechnology*, (1993) 1:59-65.
Omura, et al., "Lactacystin, A Novel Microbial Metabolite, Induces Neuritogenesis of Neuroblastoma Cells", *J Antibiotics*, (1991) 44(1): 113-116.
Ostrowska, et al., "Lactacystin, A Specific Inhibitor of the Proteasome, Inhibits Human Platelet Lysosomal Cathepsin A-like Enzyme." *Biochem Biophys Res Commun*, (1997) 234:729-732.
Ostrowska, et al., "Separation of Cathepsin A-like Enzyme and the Proteasome: Evidence that Lactacystin/ B-Lactone is not a Specific Inhibitor of the Proteasome", *Int J Biochem Cell Biol*, (2000) 32:747-757.
Otoguro, et al., "An Intergrated Method for the Enrichment and Selective Isolation of *Actinokineospora* SPP.", *J. Appl. Microbiol.*, (2001) 92:118-130.
Peckham et al., eds. "The Oxford Textbook of Oncology", *Oxford University Press*, (1995) vol. 1:447-453.
Pagano, et al., "Role of the Ubiquitin-Proteasome Pathway in Regulating Abundance of the Cyclin-Dependent Kinase Inhibitor p27", *Science*, (1995) 269(5224):682-5.
Page, Roderic D.M., "TreeView: An Application to Display Phylogenetic Trees on Personal Computers", *Computer Applications in the Biosciences*, (1996) 12:357-358.
Painter, R.B., "Inhibition of DNA Replicon Initiation by 4-Nitroquinoline 1-Oxide, Adriamycin, and Ethyleneimine", *Cancer Res*, (1978) 38(12):4445-9.
Palayoor, et al., "Constitutive Activation of ikB Kinase and NF-kB in Prostate Cancer Cells is Inhibited by Ibuprofen", *Oncogene*, (1999) 18:7389-7394.
Plunkett, et al., "Methods in Laboratory Investigation: An In Vivo Quantitative Angiogenesis Model Using Tumor Cells Entrapped in Alginate", *Laboratory Investigation*, (Apr. 1990) 62(4):510-517.
Qureshi, et al., "The Proteasome as a Libopolysaccharide-Binding Protein in Macrophages: Differential Effects of Proteasome Inhibition on Lipopolysaccharide-Induced Signaling Events," *J. Immunol.*, (2003) 171(3):1515-1525.

Rappe, et al., "Cultivation of the Ubiquitous SAR11 Marine Bacterioplankton Clade", *Nature*, (Aug. 8, 2002) 418:630-633.
Reddy, et al., "A Simple Stereocontrolled Synthesis of Salinosporamide A", *Journal of the American Chemical Society*, (2004) 126(20):6230-6231 XP008038141.
A.R. Gennaro ed., *Remington's Pharmaceutical Sciences*, 17th Ed., *Mack Publishing Co.*, Easton, PA, (1985) pp. 5 Contents.
A.R. Gennaro ed., *Remington's Pharmaceutical Sciences*, 18th Ed., *Mack Publishing Co.*, Easton, PA (1990) pp. 5 Contents.
Riva, S., "Biocatalytic Modification of Natural Products", *Curr Opin Chem Biol*, (2001) 5:106-111.
Roche, Edward B., ed.,"Bioreversible Carriers in Drug Design: Theory and Application", *Pergamon Press*, Elmsford, NY (1987) 14-21.
Romero, et al., "Thiocoraline, a New Depsipeptide with Antitumor Activity Produced by a Marine *Micromonospora*", *The Journal of Antibodics*, (1997) 50(9):734-737.
Rubanyi, Gabor M., "Angiogenesis in Health and Disease: Basic Mechanisms and Clinical Applications", *Marcel Dekker*, New York, NY (1999) pp. 6 Contents.
Ruiz, et al., The Proteasome Inhibitor NPI-0052 is a More Effective Inducer of Apoptosis than Bortezomib in Lymphocytes from Patients with Chronic Lymphocytic Leukemia, *Mol Cancer Ther.*, (2006) 5(7): 1836-43.
Sapi, et al., "Simple And Condensed beta-Lactams . . . ". *Collection of Czechoslovak Chemical Communications* (1999) 64(2):190-202.
Schnaper, et al., "Plasminogen Activators Augment Endothelial Cell Organization In Vitro by Two Distinct Pathways", *J. of Cellular Physiology*, (1995) 165:107-118.
Shah, et al., "Early Clinical Experience With the Novel Proteasome Inhibitor PS-519", *J. Clin. Pharmacol.*, (2002) 54:269-276.
Shadomy, et al., "Chemotherapeutics, Antimycotic and Antirickettsial. In: Antibiotics, Chemotherapeutics, and Antibacterial Agents for Disease Control", *John Wiley and Sons*, New York (1982) Index 3 pages.
Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study", *Clin. Ther.*, (2001) 23(3):440-50.
Shimada, et al., "Contributions of Mitogen-Activated Protein Kinase and Nuclear Factor Kappa B to N-(4-hydroxyphenyl) Retinamide-Induced Apoptosis in Prostate Cancer Cells", *Molecular Carcinogenesis*, (2002) 35(3):127-37.
Stach, et al., "Statistical Approaches for Estimating Actinobacterial Diversity in Marine Sediments", *Applied and Environmental Mircrobiology*, (Oct. 2003) 69(10):6189-6200.
Stach, et al., "New Primers for the Class Actinobacteria: Application to Marine and Terrestrial Environments", *Applied and Environmental Mircrobiology*, (2003) 5(10):828-841.
Stackebrandt, et al., "Proposal for a new Hierarchic classification systems, *Actinobacteria* classis Nov.", *Int'l Journal of Systematic Bacteriology*, (Apr. 1997) 47:479-491.
Stadler et al., "Cinnabaramides A-G: Analogues of Lactacystin and Salinosporamide from a Terrestrial Streptomycete," *J. Nat. Prod.* Feb. 2007;70(2):246-52.
Stanford, et al., "Bortezomib Treatment for Multiple Myeloma", *The Ann. Of Pharma.*, (2003) 37:1825-1830.
Streitwieser, "Introduction to Organic Chemistry", 2d ed., *Macmillan Publishing Co. Inc.*, New York, NY (1981) 169-171.
Sunwoo, et al., "Novel Proteasome Inhibitor PS-341 Inhibits Activation of Nuclear Factor-kB, Cell Survival, Tumor Growth, and Angiogenesis in Squamous Cell Carcinoma", *Clin Cancer Res*, (2001) 7:1419-28.
Takeuchi, et al., "Troglitazone Induces G1 Arrest by p27 Induction That Is Mediated by Inhibition of Proteasome in Human Gastric Cancer Cells", *Jpn J Cancer Res*, (2002) 93:774-82.
Tang, et al., "Proteasome Activity is Required For Anthrax Lethal Toxin to Kill Macrophages", *Infection and Immunity.*, (1999) 67:3055-3060.
Tang, et al., "Cloning and Hererologous Expression of the Epothilong Gene Cluster", *Science*, (Jan. 28, 2000) 287:640-2.

Tauchi, et al., "Molecular Mechanisms of Resistance of Leukemia to Imatinib Mesylate", *Leukemia Research*, (May 2004) 28:39-45.

Thompson, et al., "CLUSTAL W: Improving the Sensitivity of Progressive Multiple Sequence Alignment Through Sequence Weighting, Position-Specific Gap Penalties and Weight Matrix Choice", *Nucleic Acids Research*, (1994) 22:4673-4680.

Versalovic, et al., "Distribution of Repetive DNA Sequences in Eubacteria and Application to Fingerprinting of Bacterial Genomes", *Nucleic Acids Research*, (1991) 19(24):6823-6831.

Vitale, et al., "Susceptibility of Mitogen-Activated Protein Kinase Kinase Family Members to Proteolysis by Anthrax Lethal Factor", *Viochem J*, (2000) 352(3):739-45.

Vitale, et al., "Anthrax Lethal Factor Cleaves the N-Terminus of MAPKKS and Induces Tyrosine/Threonine Phosphorylation of MAPKS in Cultured Macrophages", *J Applied Microbiology*, (1999) 87:288.

Ward, Bess B., "How Many Species of Prokaryotes are There?", *PNAS*, (Aug. 6, 2002) 99(16):10234-10236.

Watve, et al., "How Many Antibiotics Are Produced by the Genus *Streptomyces?*", *Arch. Microbio.*, (2001) 176:386-390.

Weyland, H., "Actinomycetes in North Sea and Atlantic Ocean Sediments", *J. Nature*, (1969) 223:858.

Weyland, H., "Distribution of Actinomycetes on the Sea Floor", *Actinomycestes ZBL*. Bakt. Suppl., (1981) 11:185-193.

Wheelis, et al., "On the Nature of Global Classification", *PNAS*, (Apr. 1992) 89:2930-2934.

Williams et al., "New Cytotoix Salinosporamides Form the Marine Actinomycete *Salinispora tropica*", *J. of Organic Chemistry*, (2005) 70(16):6196-6203.

Woese, Carl R., "Bacterial Evolution", *Microbiological Rev.*, (Jun. 1987) 51(2):221-271.

Zaks, A., "Industrial Biocatalysis", *Curr Opin Chem Biol*, (2001) 5:130-6.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia", *Stroke*, (2001) 2926-2931.

Zheng, et al., "Detection of Antitumor and Antimicrobial Activites in Marine Organism Associated Actinomycetes Isolated From the Taiwan Strait, China", *FEMS Microbiology Letters*, (2000) 188:87-91.

Beers, et al., "The Merck Manual of Diagnosis and Therapy" The Merck Research Laboratories, Whitehouse Station N.J. XP002510943, (1999) p. 1193, col. 3, para. 1; Chapter 157, pp. 1193-1201 and 1204.

Corey et al. "The Structural Requirements for Inhibition of Proteasome Function by the Lactacystin-derived beta-lactone and Synthetic Analogs", *Tetrahedron* (1999) 55(11):3305-3316.

Crueger, et al., "Biotechnology: A Textbook of Industrial Microbiology", 2nd ed., *Sinauer Associates, Inc.*, (1990) p. 4-8.

Endo, et al., "Total Synthesis of Salinosporamide A", *J Am Chem Soc.*, (2005) 127(23): 8298-8299 and Supporting Information S1-S23.

Giannangeli, et al., "Effect of modifications of the alkylpiperazine moiety of trazodone on 5HT2A and alpha1 receptor binding affinity", *J Med Chem.*, (1999) 42(3):336-45.

O'Neil, M. "The Merck Index Thirteenth Edition" Merck Research Laboratories, Whitehouse Station, N.J. XP002510887, (2001) pp. THER-5, col. 3—pp. THER-7, col. 2.

Online URL:http://en.wikipedia.org/wiki/Myeloma; pp. 1-8, (Jul. 2008).

Online URL:http://en.wikipedia.org/wiki/Sarcoma; pp. 1-2, (May 2008).

Prudhomme, et al., "Marine actinomycetes: a new source of compounds against the human malaria parasite", *PLoS ONE* (2008) 3(6):e2335 XP008100452.

Schiewe, H. (Reprint) Haustedt, et al., "Rational approahces to natural-product-based drug design", *Curr Opin Drug Disc Devel.* (2006) 9(4):445-462.

Shoemaker, R., "The NCI60 Human Tumour Cell Line Anticancer Drug Screen", *Nature Reviews Cancer*, (2006) 6:813-823.

Silverman "The Organic Chemistry of Drug Design and Drug Action", *Academic Press*, (1992) p. 2 & 19-21.

Stackebrandt, et al., "Taxonomic Note: A Place for DNA-DNA Reassociation and 16S rRNA Sequence Analysis in the Present Species Definition in Bacteriology", *Int J Syst Bacteriol.*, (1994) 44(4):846-849.

Voskoglou-Nomikos, et al., "Clinical Predictive Value of the in Vitro Cell Line, Human Xenograft, and Mouse Allograft Preclinical Cancer Models", *Clin Cancer Res.*, (2003) (:4227-4239.

International Search Report and Written Opinion mailed Jul. 12, 2006 in International Application No. PCT/US2005/044091; International Filing Date: Dec. 2, 2005.

International Preliminary Report on Patentability dated Jun. 5, 2007 in International Application No. PCT/US2005/044091, International Filing Date: Dec. 2, 2005.

International Search Report and Written Opinion (corrected version) dated Jul. 8, 2005 in International Application No. PCT/US2004/019543; International Filing Date: Jun. 18, 2004.

International Preliminary Report on Patentability dated Jan. 3, 2006 in International Application No. PCT/US2004/019543, International Filing Date Jun. 18, 2004.

Office Action in U.S. Appl. No. 11/118,260, Dated Oct. 30, 2006.
Notice of Allowance in U.S. Appl. No. 11/118,260, Dated Apr. 24, 2007.
Office Action in U.S. Appl. No. 09/991,518, Dated Sep. 15, 2003.
Office Action in U.S. Appl. No. 09/991,518, Dated Feb. 24, 2004.
Office Action in U.S. Appl. No. 09/991,518, Dated Aug. 20, 2004.
Office Action in U.S. Appl. No. 09/991,518, Dated Feb. 15, 2005.
Office Action in U.S. Appl. No. 09/991,518, Dated Jun. 27, 2005.
Office Action in U.S. Appl. No. 09/991,518, Dated Nov. 4, 2005.
Notice of Allowance in U.S. Appl. No. 09/991,518, Dated Apr. 24, 2006.
Office Action in U.S. Appl. No. 11/228,416, Dated Feb. 21, 2007.

Andtbacka, et al., "The Proteasome Inhibitor NPI-0052 Sensitizes Pancreatic Cancer Cells to TRAIL In Vitro and In Vivo," Amer. Assoc. Cancer Res., (2005) 46: Abstract #1721.

Andtbacka, et al., "The Proteasome Inhibitor NPI-0052 Overcomes TRAIL Resistance in Human Pancreatic Cancer Cells In Vitro and In Vivo," Cancer Research, (2007) (under revision).

Barral, et al., "The Proteasome Inhibitor NPI-0052 Reduces Tumor Growth and Overcomes Resistance of Prostate Cancer to rhTRAIL via Inhibition of the NF-kB Pathway," Amer. Assoc. Cancer Res., (2007): abstract 1465.

Beers et al. (Eds.), *The Merck Manual of Diagnosis and Therapy*, 17th Ed. 1999, The Merck Research Laboratories, Whitehouse Station N. J., pp. 397-399, 948-949, 1916-1917, 1974-1975 and 1978-1983.

Cusack, et al., "Oral proteasome inhibitor (NPI-0052) enhances sensitivity to combination Gemcitabine and Erbitux in a pancreatic cancer xenograft model," Nereus Pharmaceuticals, Inc., (Apr. 19, 2005), abstract 4943 for presentation at the American Association of Cancer Research Annual Meeting held on Apr. 19, 2005 in Orange County, CA, 1 page.

Khanbolooki, et al., "Novel NFkB inhibitors NPI-1342/NPI-1387 and proteasome inhibitor NPI-0052 overcome resistance of pancreatic carcinoma to rhTRAIL," Nereus Pharmaceuticals, Inc., (Apr. 2, 2006), abstract 780 for presentation at the American Association of Cancer Research Annual Meeting held on Apr. 2, 2006 in Washington, D.C., 1 page.

Manam, et al., "Stereoselective Enzymatic Reduction of Keto-Salinosporamide to (−)—salinosporamide a (NPI-0052)," *Tetra. Lettr.*, (2007) 48: 2537-2540.

Roccaro, et al., "Dual Targeting of the Proteasome Regulates Survival and Homing in Waldenstrom Macroglobulinemia." Blood, (Mar. 2008) 111(9): 4752-4763.

Stanford, et al., "Bortezomib Treatment for Multiple Myeloma," *Ann. Pharmacother.*, (2003) 37:1825-1830.

Suzuki, et al., "Chemosensitization of Drug and Rituximab-Resistant Daudi B-NHL Clones to Drug-Induced Apoptosis by the Proteasome Inhibitor NPI-0052," Blood, (2005) 106:1521 abstract.

Tang, et al., "Cloning and Hererologous Expression of the Epothilong Gene Cluster," *Science*, (Jan. 28, 2000) 287:640-642.

EFS File History of U.S. Appl. No. 11/966,801, filed Dec. 28, 2007.
EFS File History of U.S. Appl. No. 12/638,860, filed Dec. 15, 2009 as of Aug. 3, 2011.

EFS File History of U.S. Appl. No. 10/561,711, filed Sep. 11, 2009 as of Aug. 26, 2011.

EFS File History of U.S. Appl. No. 12/720,557, filed Mar. 9, 2010 as of Jul. 1, 2010.

EFS File History of U.S. Appl. No. 13/052,827, filed Mar. 21, 2011 as of Sep. 19, 2011.

EFS File History of U.S. Appl. No. 12/183,007, filed Jul. 30, 2008 as of Aug. 9, 2011.

EFS File History of U.S. Appl. No. 12/329,504, filed Dec. 5, 2008 as of Aug. 16, 2011.

* cited by examiner

Pan-tropical Distribution of the *Salinospora*

X = *Salinospora* collection sites

Typical 16S rDNA Sequence of the *Salinospora*

Bars represent characteristic signature nucleotides of the *Salinospora* that separate them from their nearest relatives (*Micromonospora* species). >2% sequence divergence from nearest neighbor (M. olivasterospora)

II-20

II-24C

II-19

II-2

II-3

II-4

II-5A

II-5B

IV-3C

IV-3C

II-13C

II-8C

II-25

II-21

II-22

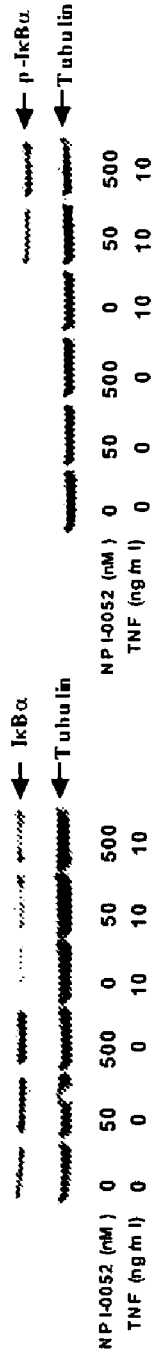
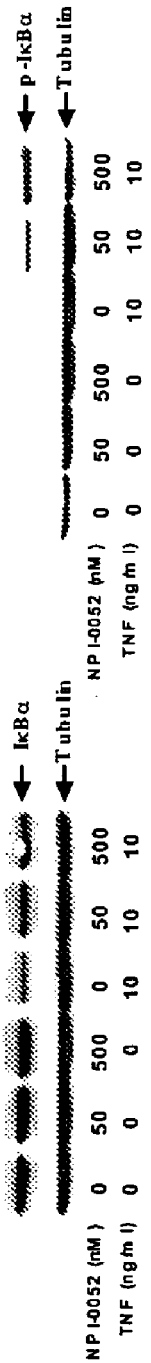
FIG. 32A
FIG. 32B
Reduction of IκBα degradation and Retention of Phosphorylated IκBα by II-16 in HEK293 Cells (A) and the HEK293 NF-κB/Luciferase Reporter Clone (B).

Accumulation of Cell Cycle Regulatory Proteins, p21 and p27 by 11-16 Treatment of HEK293 Cells (A) and the HEK293 NF-κB/Luciferase Reporter Clone (B).

METHODS OF USING [3.2.0] HETEROCYCLIC COMPOUNDS AND ANALOGS THEREOF

This application is a continuation of U.S. application Ser. No. 10/871,368, filed Jun. 18, 2004 now abandoned, entitled "METHODS OF USING (3.2.0) HETEROCYCLIC COMPOUNDS AND ANALOGS THEREOF," which claims priority under 35 U.S.C. §119(e) to U.S. Provisional Application No. 60/480,270, filed on Jun. 20, 2003, entitled USE OF SALINOSPORAMIDE A TO TREAT LeTx INTOXICATION AND B. ANTHRACIS INFECTION, and to U.S. Provisional Application No. 60/566,952, filed on Apr. 30, 2004, entitled METHODS OF USING (3.2.0) HETEROCYCLIC COMPOUNDS AND ANALOGS THEREOF; the disclosures of all aforementioned application are incorporated herein by reference in their entireties.

BACKGROUND

1. Field of the Invention

The present invention relates to certain compounds and to methods for the preparation and the use of certain compounds in the fields of chemistry and medicine. Embodiments of the invention disclosed herein relate to methods of using heterocyclic compounds. In some embodiments, the compounds are used as proteasome inhibitors. In other embodiments, the compounds are used to treat inflammation, cancer, and infectious diseases.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY

The embodiments disclosed herein generally relate to chemical compounds, including heterocyclic compounds and analogs thereof. Some embodiments are directed to the use of compounds as proteasome inhibitors.

In other embodiments, the compounds are used to treat neoplastic diseases, for example, to inhibit the growth of tumors, cancers and other neoplastic tissues. The methods of treatment disclosed herein may be employed with any patient suspected of carrying tumorous growths, cancers, or other neoplastic growths, either benign or malignant ("tumor" or "tumors" as used herein encompasses tumors, cancers, disseminated neoplastic cells and localized neoplastic growths). Examples of such growths include but are not limited to breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; kidney cancers; endocrine cancers; skin cancers; melanomas; angiomas; and brain or central nervous system (CNS) cancers. In general, the tumor or growth to be treated may be any tumor or cancer, primary or secondary. Certain embodiments relate to methods of treating neoplastic diseases in animals. The method can include, for example, administering an effective amount of a compound to a patient in need thereof. Other embodiments relate to the use of compounds in the manufacture of a pharmaceutical or medicament for the treatment of a neoplastic disease. The compounds can be administered in combination with a chemotherapeutic agent.

In still other embodiments, the compounds are used to treat inflammatory conditions. Certain embodiments relate to methods of treating inflammatory conditions in animals. The method can include, for example, administering an effective amount of a compound to a patient in need thereof. Other embodiments relate to the use of compounds in the manufacture of a pharmaceutical or medicament for the treatment of inflammation.

In certain embodiments, the compounds are used to treat infectious diseases. The infectious agent can be a microbe, for example, bacteria, fungi, protozoans, and microscopic algae, or viruses. Further, the infectious agent can be *B. anthracis* (anthrax). In some embodiments the infectious agent is a parasite. For example, the infectious agent can be *Plasmodium, Leishmania*, and *Trypanosoma*. Certain embodiments relate to methods of treating infectious agents in animals. The method can include, for example, administering an effective amount of a compound to a patient in need thereof. Other embodiments relate to the use of compounds in the manufacture of a pharmaceutical or medicament for the treatment of infectious agents.

Some embodiments relate to uses of a compound having the structure of Formula I, and pharmaceutically acceptable salts and pro-drug esters thereof:

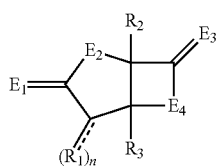

Formula I wherein the dashed lines represent a single or a double bond, wherein R1 may be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where n is equal to 1 or 2, and if n is equal to 2, then $R_1$ can be the same or different;

wherein $R_2$, may be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl (including, for example, cyclohexylcarbinol), alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl;

wherein $R_3$ may be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl; and wherein each of $E_1$, $E_2$, $E_3$ and $E_4$ is a substituted or unsubstituted heteroatom; in the treatment of cancer, inflammation, and infectious disease.

Other embodiments relate to methods of treating a neoplastic disease in an animal. The methods can include, for example, administering to the animal, a therapeutically effective amount of a compound of a formula selected from Formulae I-V, and pharmaceutically acceptable salts and pro-drug esters thereof.

Further embodiments relate to pharmaceutical compositions which include a compound of a formula selected from Formulae I-V. The pharmaceutical compositions can further include an anti-microbial agent.

Still further embodiments relate to methods of inhibiting the growth of a cancer cell. The methods can include, for example, contacting a cancer cell with a compound of a formula selected from Formulae I-V, and pharmaceutically acceptable salts and pro-drug esters thereof.

Other embodiments relate to methods of inhibiting proteasome activity that include the step contacting a cell with a compound of a formula selected from Formulae I-V, and pharmaceutically acceptable salts and pro-drug esters thereof.

Other embodiments relate to methods of inhibiting NF-κB activation including the step contacting a cell with a compound of a formula selected from Formulae I-V, and pharmaceutically acceptable salts and pro-drug esters thereof.

Some embodiments relate to methods for treating an inflammatory condition, including administering an effective amount of a compound of a formula selected from Formulae I-V to a patient in need thereof.

Further embodiments relate to methods for treating a microbial illness including administering an effective amount of a compound of a formula selected from Formulae I-V to a patient in need thereof.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings:

FIG. 32 shows reduction of IκBα degradation and retention of phosphorylated IκBα by II-16 in HEK293 cells (A) and the HEK293 NF-κB/Luciferase reporter clone (B).

FIG. 48 depicts the effect of Formulae II-2, II-3, and II-4 against LeTx-mediated cytotoxicity.

FIG. 49 depicts the 1H NMR spectrum of a compound having structure Formula II-17.

DETAILED DESCRIPTION

Figure 1:
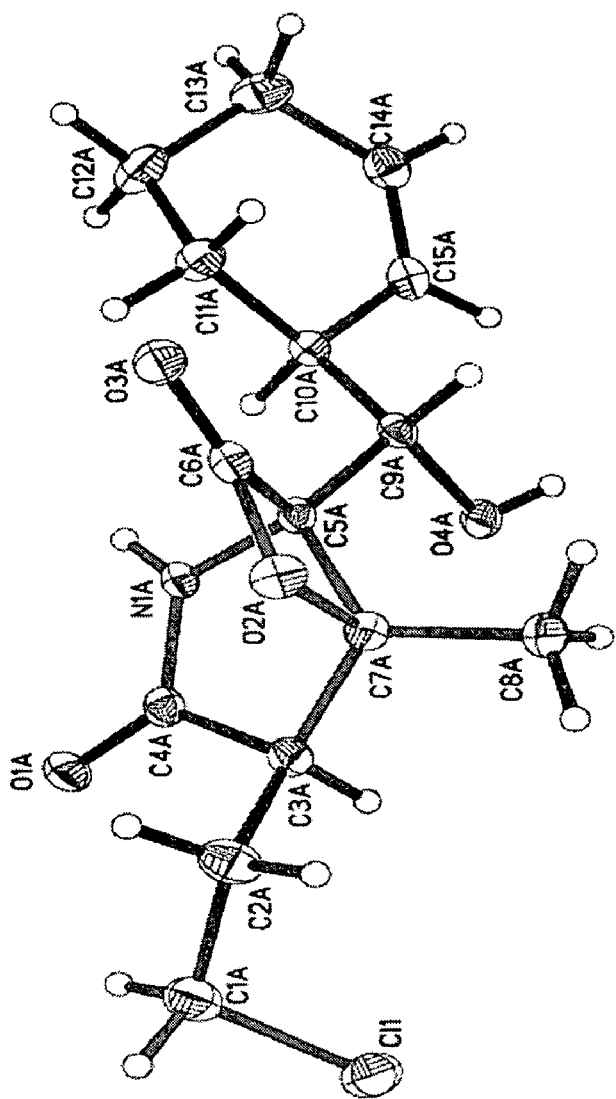
FIG. 1 shows the chemical structure of Salinosporamide A.
Figure 1:
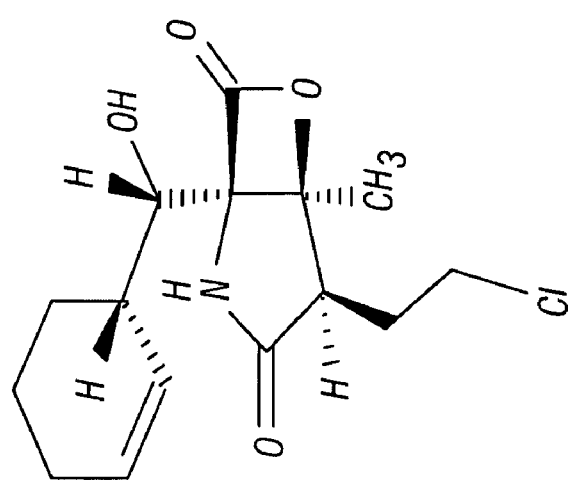

Numerous references are cited herein. The references cited herein, including the U.S. patents cited herein, are each to be considered incorporated by reference in their entirety into this specification.

Embodiments of the invention include, but are not limited to, providing a method for the preparation of compounds, including compounds, for example, those described herein and analogs thereof, and to providing a method for producing pharmaceutically acceptable anti-microbial, anti-cancer, and anti-inflammatory compositions, for example. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating cancer, inflammation, and infectious diseases, particularly those affecting humans. The methods may include, for example, the step of administering an effective amount of a member of a class of new compounds. Preferred embodiments relate to the compounds and methods of making and using such compounds disclosed herein, but not necessarily in all embodiments of the present invention, these objectives are met.

For the compounds described herein, each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that the compounds encompasses all possible stereoisomers.

Compounds of Formula I

Some embodiments provide compounds, and methods of producing a class of compounds, pharmaceutically acceptable salts and pro-drug esters thereof, wherein the compounds are represented by Formula I:

Formula I

In certain embodiments the substituent(s) $R_1$, $R_2$, and $R_3$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl. Further, in certain embodiments, each of $E_1$, $E_2$, $E_3$ and $E_4$ may be a substituted or unsubstituted heteroatom, for example, a heteroatom separately selected from the group consisting of nitrogen, sulfur and oxygen.

In some embodiments n may be equal to 1 or equal to 2. When n is equal to 2, the substituents can be the same or can be different. Furthermore, in some embodiments $R_3$ is not a hydrogen.

Preferably, $R_2$ may be a formyl. For example, the compound may have the following structure I-1:

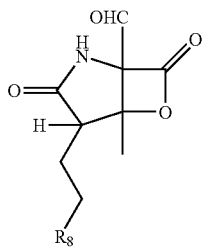

Formula I-1

$R_8$ may include, for example, hydrogen, fluorine, chlorine, bromine and iodine.

Preferably, the structure of Formula I-1 may have the following stereochemistry:

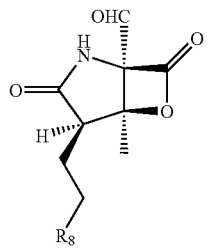

$R_8$ may include, for example, hydrogen, fluorine, chlorine, bromine and iodine.

Preferably, $R_2$ may be a carbinol. For example, the compound may have the following structure I-2:

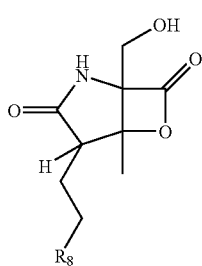

Formula I-2

$R_8$ may include, for example, hydrogen, fluorine, chlorine, bromine and iodine.

As an example, the structure of Formula I-2 may have the following stereochemistry:

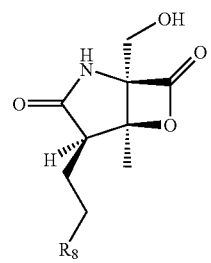

$R_8$ may include, for example, hydrogen, fluorine, chlorine, bromine and iodine.

As exemplary compound of Formula I may be the compound having the following structure I-3:

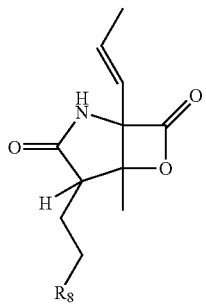

Formula I-3

$R_8$ may include, for example, hydrogen, fluorine, chlorine, bromine and iodine.

The compound of Formula I-3 may have the following stereochemical structure:

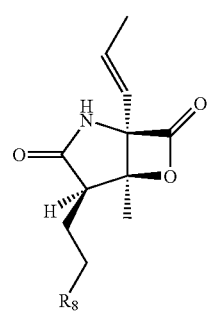

$R_8$ may include, for example, hydrogen, fluorine, chlorine, bromine and iodine.

Another exemplary compound Formula I may be the compound having the following structure I-4:

Formula I-4

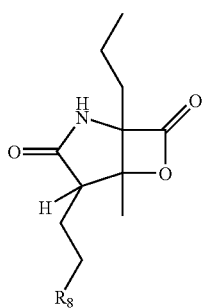

R$_8$ may include, for example, hydrogen, fluorine, chlorine, bromine and iodine.

Preferably, the compound of Formula I-4 may have the following stereochemical structure:

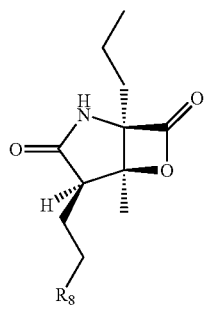

R$_8$ may include, for example, hydrogen, fluorine, chlorine, bromine and iodine.

Still a further exemplary compound of Formula I is the compound having the following structure I-5:

Formula I-5

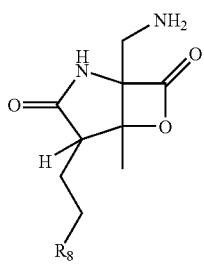

R$_8$ may include, for example, hydrogen, fluorine, chlorine, bromine and iodine.

For example, the compound of Formula I-5 may have the following stereochemistry:

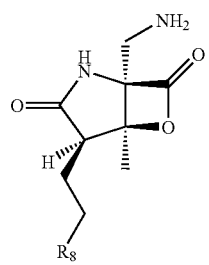

R$_8$ may include, for example, hydrogen, fluorine, chlorine, bromine and iodine.

In some embodiments, R$_2$ of Formula I may be, for example, a 3-methylenecyclohexene. For example, the compound may have the following structure of Formula I-6:

Formula I-6

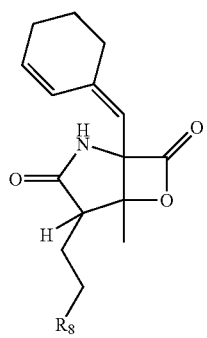

R$_8$ may include, for example, hydrogen, fluorine, chlorine, bromine and iodine.

Preferably, the compound of Formula I-6 may have the following stereochemistry:

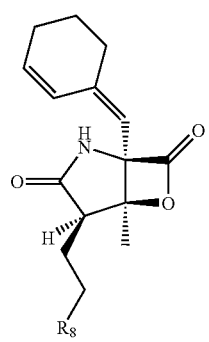

R$_8$ may include, for example, hydrogen, fluorine, chlorine, bromine and iodine.

In other embodiments, R$_2$ may be a cyclohexylalkylamine.

Also, in other embodiments, R$_2$ may be a C-Cyclohexyl-methyleneamine. In others, R$_2$ may be a cyclohexanecarbaldehyde O-oxime.

Furthermore, in some embodiments, R$_2$ may be a cycloalkylacyl.

Compounds of Formula II

Other embodiments provide compounds, and methods of producing a class of compounds, pharmaceutically acceptable salts and pro-drug esters thereof, wherein the compounds are represented by Formula II:

Formula II

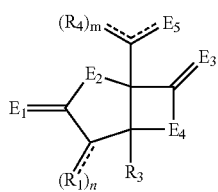

In certain embodiments the substituent(s) $R_1$, $R_3$, and $R_4$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl. Further, in certain embodiments, each of $E_1$, $E_2$, $E_3$ and $E_4$ may be a substituted or unsubstituted heteroatom, for example, a heteroatom or substituted heteroatom selected from the group consisting of nitrogen, sulfur and oxygen.

In some embodiments n may be equal to 1, while in others it may be equal to 2. When n is equal to 2, the substituents can be the same or can be different. Furthermore, in some embodiments $R_3$ is not a hydrogen. m can be equal to 1 or 2, and when m is equal to 2, $R_4$ can be the same or different.

$E_5$ may be, for example, OH, O, $OR_{10}$, S, $SR_{11}$, $SO_2R_{11}$, NH, $NH_2$, NOH, NHOH, $NR_{12}$, and $NHOR_{13}$, wherein $R_{10-13}$ may separately include, for example, hydrogen, a substituted or unsubstituted of any of the following: alkyl, an aryl, a heteroaryl, and the like. Also, $R_1$ may be $CH_2CH_2X$, wherein X may be, for example, H, F, Cl, Br, and I. $R_3$ may be methyl. Furthermore, $R_4$ may include a cyclohexyl. Also, each of $E_1$, $E_3$ and $E_4$ may be O and $E_2$ may be NH. Preferably, $R_1$ may be $CH_2CH_2X$, wherein X is selected from the group consisting of H, F, Cl Br, and I; wherein $R_4$ may include a cyclohexyl; wherein $R_3$ may be methyl; and wherein each of $E_1$, $E_3$ and $E_4$ separately may be O and $E_2$ may be NH.

For example, an exemplary compound of Formula II has the following structure II-1:

Formula II-1

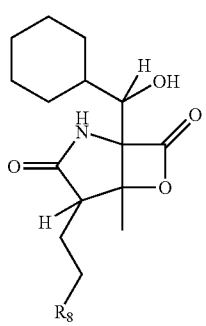

$R_8$ may include, for example, hydrogen, fluorine, chlorine, bromine and iodine.

Exemplary stereochemistry may be as follows:

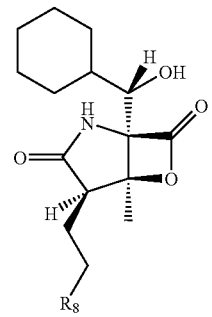

In preferred embodiments, the compound of Formula II has any of the following structures:

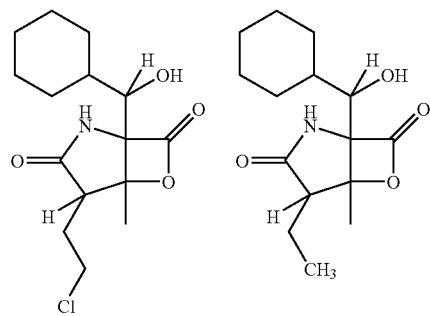

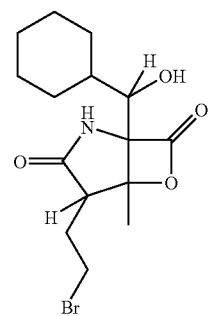

The following is exemplary stereochemistry for compounds having the structures II-2, II-3, and II-4, respectively:

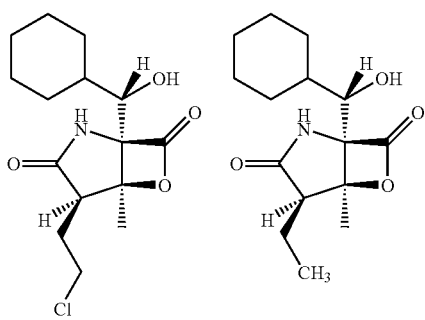

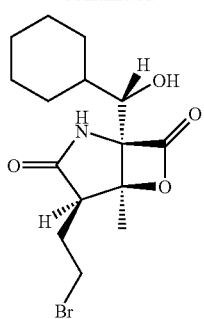

In other embodiments wherein $R_4$ may include a 7-oxa-bicyclo[4.1.0]hept-2-yl). An exemplary compound of Formula II is the following structure II-5:

Formula II-5

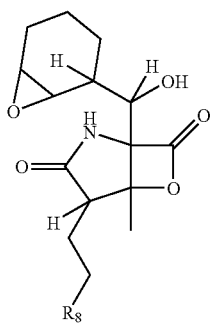

$R_8$ may include, for example, hydrogen, fluorine, chlorine, bromine and iodine.

The following are examples of compounds having the structure of Formula II-5:

Formulae II-5A and II-5B

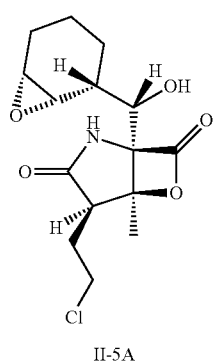 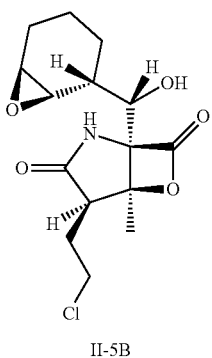

II-5A  II-5B

In still further embodiments, at least one $R_4$ may include a substituted or an unsubstituted branched alkyl. For example, a compound of Formula II may be the following structure II-6:

Formula II-6

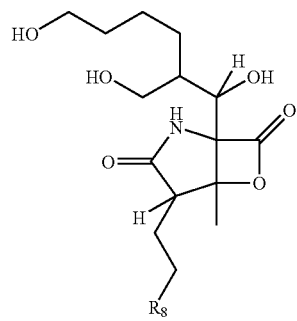

$R_8$ may include, for example, hydrogen, fluorine, chlorine, bromine and iodine.

The following is exemplary stereochemistry for a compound having the structure of Formula II-6:

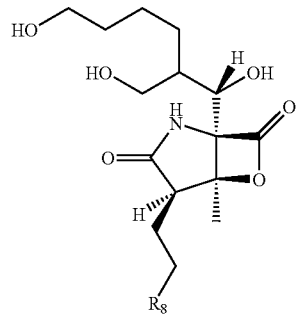

As another example, the compound of Formula II may be the following structure II-7:

Formula II-7

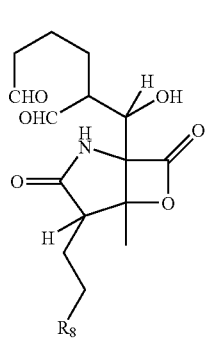

$R_8$ may include, for example, hydrogen, fluorine, chlorine, bromine and iodine.

The following is exemplary stereochemistry for a compound having the structure of Formula II-7:

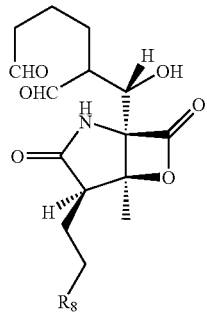

In other embodiments, at least one $R_4$ may be a cycloalkyl and $E_5$ may be an oxygen. An exemplary compound of Formula II may be the following structure II-8:

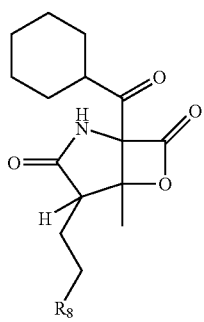

Formula II-8

$R_8$ may include, for example, hydrogen (II-8A), fluorine (II-8B), chlorine (II-8C), bromine (II-8D) and iodine (II-8E).

The following is exemplary stereochemistry for a compound having the structure of Formula II-8:

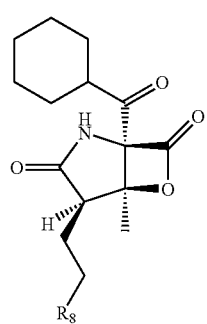

In some embodiments E5 may be an amine oxide, giving rise to an oxime. An exemplary compound of Formula II has the following structure II-9:

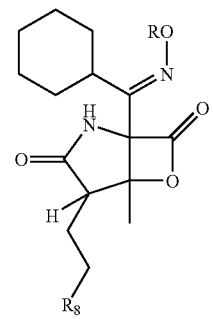

Formula II-9

$R_8$ may include, for example, hydrogen, fluorine, chlorine, bromine and iodine; R may be hydrogen, and a substituted or unsubstituted alkyl, aryl, or heteroaryl, and the like.

The following is exemplary stereochemistry for a compound having the structure of Formula II-9:

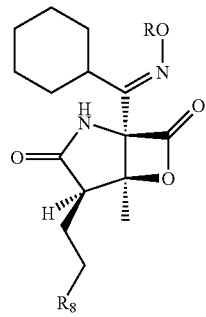

A further exemplary compound of Formula II has the following structure II-10:

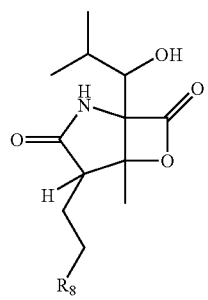

Formula II-10

$R_8$ may include, for example, hydrogen, fluorine, chlorine, bromine and iodine.

The following is exemplary stereochemistry for a compound having the structure of Formula II-10:

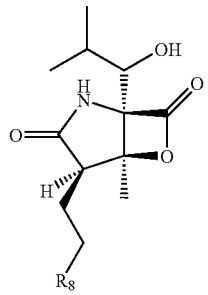

In some embodiments, $E_5$ may be $NH_2$. An exemplary compound of Formula II has the following structure II-11:

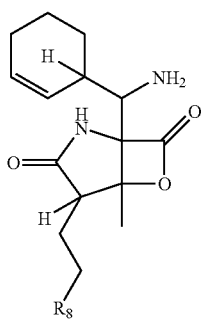

Formula II-11

$R_8$ may include, for example, hydrogen, fluorine, chlorine, bromine and iodine.

The following is exemplary stereochemistry for a compound having the structure of Formula II-11:

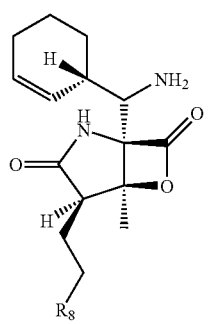

In some embodiments, at least one $R_4$ may include a cycloalkyl and $E_5$ may be $NH_2$. An exemplary compound of Formula II has the following structure II-12:

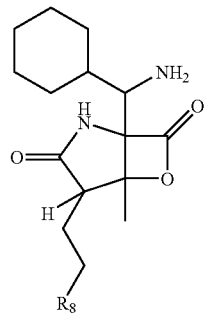

Formula II-12

$R_8$ may include, for example, hydrogen, fluorine, chlorine, bromine and iodine.

The following is exemplary stereochemistry for a compound having the structure of Formula II-12:

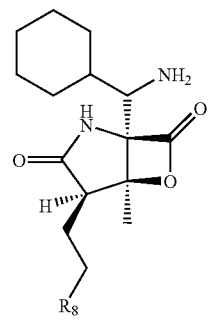

A further exemplary compound of Formula II has the following structure II-13:

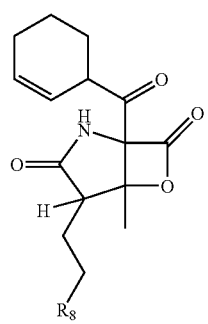

Formula II-13

$R_8$ may include, for example, hydrogen (II-13A), fluorine (II-13B), chlorine (II-13C), bromine (II-13D) and iodine (II-13E).

The following is exemplary stereochemistry for a compound having the structure of Frmula II-13:

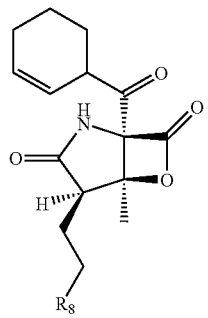

A still further exemplary compound of Formula II has the following structure II-14:

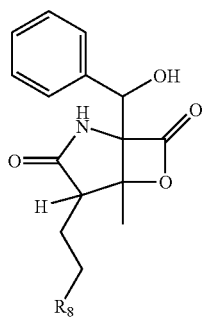

Formula II-14

R$_8$ may include, for example, hydrogen, fluorine, chlorine, bromine and iodine.

The following is exemplary stereochemistry for a compound having the structure of Formula II-14:

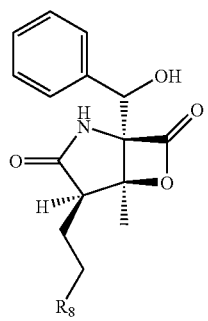

In some embodiments, the compounds of Formula II, may include as R$_4$ at least one cycloalkene, for example. Furthermore, in some embodiments, the compounds may include a hydroxy at E$_5$, for example. A further exemplary compound of Formula II has the following structure II-15:

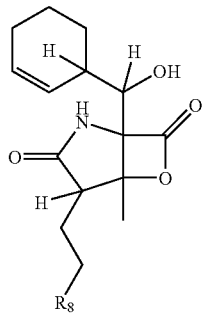

Formula II-15

R$_8$ may include, for example, hydrogen, fluorine, chlorine, bromine and iodine.

Exemplary stereochemistry may be as follows:

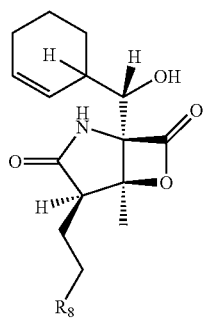

The following is exemplary stereochemistry for compounds having the structures II-16, II-17, II-18, and II-19, respectively:

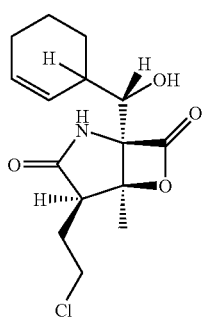

II-16

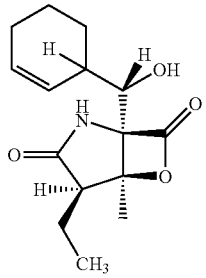

II-17

II-18

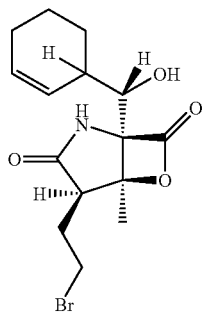

II-19

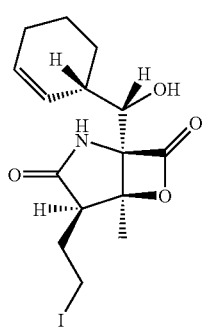

The compounds of Formulae II-16, II-17, II-18 and II-19 may be obtained by fermentation, synthesis, or semi-synthesis and isolated/purified as set forth below. Furthermore, the compounds of Formulae II-16, II-17, II-18 and II-19 may be used, and are referred to, as "starting materials" to make other compounds described herein.

In some embodiments, the compounds of Formula II, may include a methyl group as $R_1$, for example. A further exemplary compound, Formula II-20, has the following structure and stereochemistry:

II-20

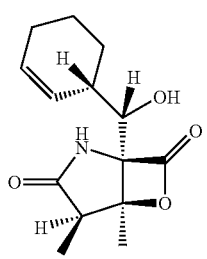

In some embodiments, the compounds of Formula II, may include hydroxyethyl as $R_1$, for example. A further exemplary compound, Formula II-21, has the following structure and stereochemistry:

II-21

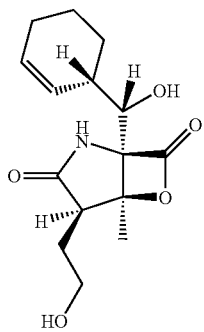

In some embodiments, the hydroxyl group of Formula II-21 may be esterified such that $R_1$ may include ethylpropionate, for example. An exemplary compound, Formula II-22, has the following structure and stereochemistry:

II-22

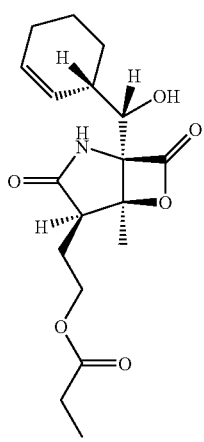

In some embodiments, the compounds of Formula II may include an ethyl group as $R_3$, for example. A further exemplary compound of Formula II has the following structure II-23:

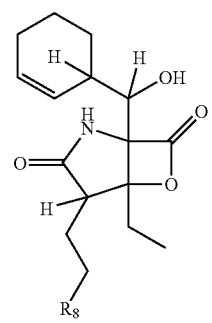

$R_8$ may include, for example, hydrogen, fluorine, chlorine, bromine and iodine. Exemplary stereochemistry may be as follows:

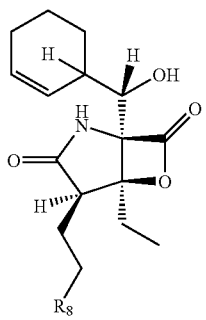

In some embodiments, the compounds of Formula II-23 may have the following structure and stereochemistry, exemplified by Formula II-24C, where $R_8$ is chlorine:

II-24C

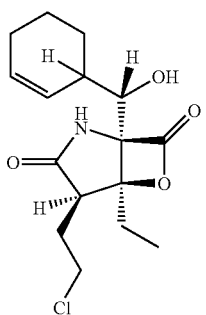

In some embodiments, the compounds of Formula II-15 may have the following stereochemistry, exemplified by the compound of Formula II-25, where $R_8$ is chlorine:

II-25

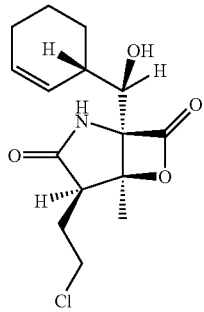

Compounds of Formula III

Other embodiments provide compounds, and methods of producing a class of compounds, pharmaceutically acceptable salts and pro-drug esters thereof, wherein the compounds are represented by Formula III:

Formula III

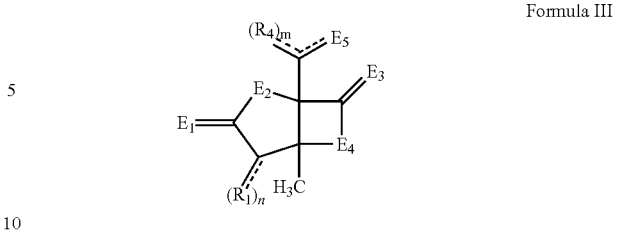

In certain embodiments, the substituent(s) $R_1$ separately may include, for example, a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. For example, n can be equal to 1 or 2.

In certain embodiments, $R_4$ may be, for example, a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. In some embodiments m can be equal to 1 or 2, and where m is equal to 2, the substituents can the same or different. Also, each of $E_1$, $E_2$, $E_3$, $E_4$ and $E_5$ may be, for example, a substituted or unsubstituted heteroatom. For example, the heteroatom may be nitrogen, sulfur or oxygen.

Compounds of Formula IV

Other embodiments provide compounds, and methods of producing a class of compounds, pharmaceutically acceptable salts and pro-drug esters thereof, wherein the compounds are represented by Formula IV:

Formula IV

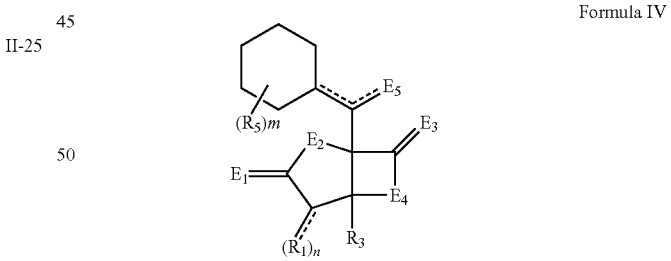

In certain embodiments, the substituent(s) $R_1$, $R_3$, and $R_5$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Also, each of $E_1$, $E_2$, $E_3$, $E_4$ and $E_5$ may be a heteroatom or substituted heteroatom, for example, nitrogen, sulfur or oxygen. In some embodiments, $R_3$ is not a hydrogen. n is equal to 1 or 2. When n is equal to 2, the substituents can be the same or can be different. Also, m can be 0, 1, 2, 3, 4, 5, 6, 7, 8, 9, 10, or 11. When m is greater than 1, the substituents can be the same or different.

In some embodiments $R_5$ may give rise to a di-substituted cyclohexyl. An exemplary compound of Formula IV is the following structure IV-1, with and without exemplary stereochemistry:

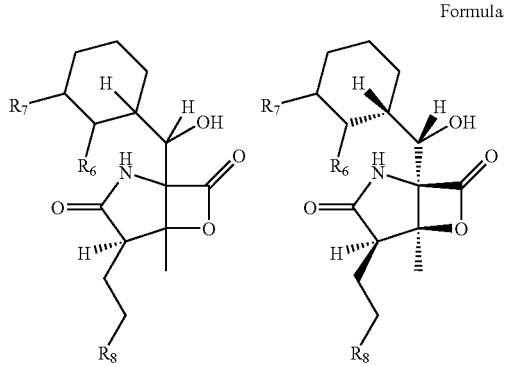

Formula IV-1

$R_8$ may include, for example, hydrogen, fluorine, chlorine, bromine and iodine. The substituent(s) $R_6$ and $R_7$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Further, $R_6$ and $R_7$ both may be the same or different.

For example, an exemplary compound of Formula IV has the following structure IV-2:

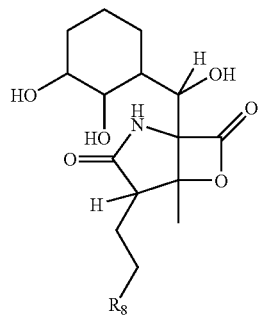

Formula IV-2

$R_8$ may include, for example, hydrogen, fluorine, chlorine, bromine and iodine.

Exemplary stereochemistry may be as follows:

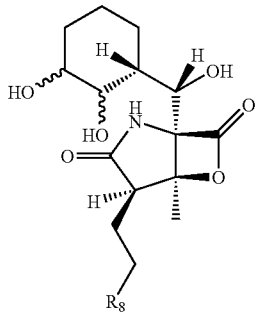

For example, an exemplary compound of Formula IV has the following structure IV-3:

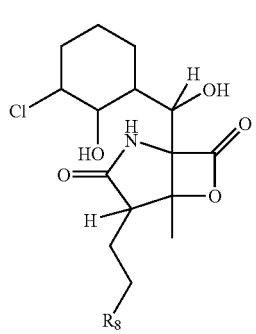

Formula IV-3

$R_8$ may include, for example, hydrogen (IV-3A), fluorine (IV-3B), chlorine (IV-3C), bromine (IV-3D) and iodine (IV-3E).

Exemplary structure and stereochemistry may be as follows:

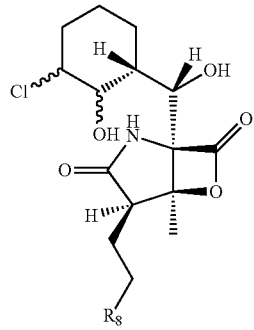

Additional exemplary structure and stereochemistry may be as follows:

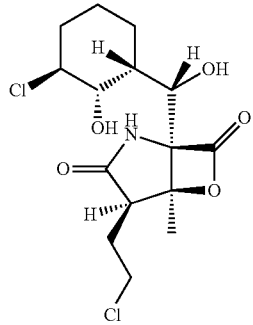

Formula IV-3C

For example, an exemplary compound of Formula IV has the following structure IV-4:

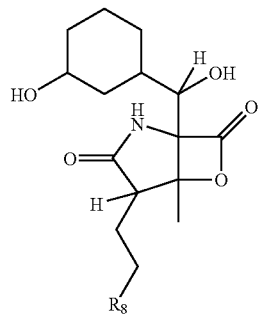

Formula IV-4

$R_8$ may include, for example, hydrogen, fluorine, chlorine, bromine and iodine.

Exemplary stereochemistry may be as follows:

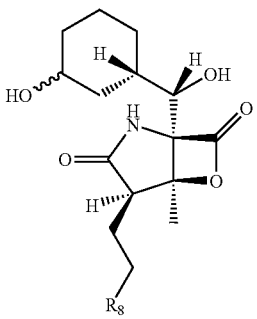

Compounds of Formula V

Some embodiments provide compounds, and methods of producing a class of compounds, pharmaceutically acceptable salts and pro-drug esters thereof, wherein the compounds are represented by Formula V:

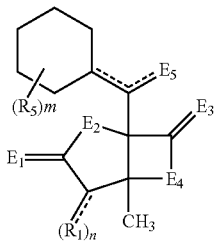

Formula V

In certain embodiments, the substituent(s) $R_1$ and $R_5$ may separately include a hydrogen, a halogen, a mono-substituted, a poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. In certain embodiments, each of $E_1$, $E_2$, $E_3$, $E_4$ and $E_5$ may be a heteroatom or substituted heteroatom, for example, nitrogen, sulfur or oxygen. n can be equal to 1 or 2, and when n is equal to 2, the substituents can be the same or different. Preferably, m may be, for example, 0, 1, 2, 3, 4, 5, 6, 7, 8, 9, 10, or 11. When m is greater than 1, $R_5$ may be the same or different.

Certain embodiments also provide pharmaceutically acceptable salts and pro-drug esters of the compound of Formulae I-V, and provide methods of obtaining and purifying such compounds by the methods disclosed herein.

The term "pro-drug ester," especially when referring to a pro-drug ester of the compound of Formula I synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood.

The term "pharmaceutically acceptable salt," as used herein, and particularly when referring to a pharmaceutically acceptable salt of a compound, including Formulae I-V, and Formula I-V as produced and synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds synthesized by the method of this embodiment that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formulae I-V obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

It will be also appreciated that the phrase "compounds and compositions comprising the compound," or any like phrase, is meant to encompass compounds in any suitable form for pharmaceutical delivery, as discussed in further detail herein. For example, in certain embodiments, the compounds or compositions comprising the same may include a pharmaceutically acceptable salt of the compound.

In one embodiment the compounds may be used to treat microbial diseases, cancer, and inflammation. Disease is meant to be construed broadly to cover infectious diseases, and also autoimmune diseases, non-infectious diseases and chronic conditions. In a preferred embodiment, the disease is caused by a microbe, such as a bacterium, a fungi, and protozoa, for example. The methods of use may also include the steps of administering a compound or composition comprising the compound to an individual with an infectious disease or cancer. The compound or composition can be administered in an amount effective to treat the particular infectious disease, cancer or inflammatory condition.

The infectious disease may be, for example, one caused by *Bacillus*, such as *B. anthracis* and *B. cereus*. The infectious disease may be one caused by a protozoa, for example, a *Leishmania*, a *Plasmodium* or a *Trypanosoma*. The compound or composition may be administered with a pharmaceutically acceptable carrier, diluent, excipient, and the like.

The cancer may be, for example, a multiple myeloma, a colorectal carcinoma, a prostate carcinoma, a breast adenocarcinoma, a non-small cell lung carcinoma, an ovarian carcinoma, a melanoma, and the like.

The inflammatory condition may be, for example, rheumatoid arthritis, asthma, multiple sclerosis, psoriasis, stroke, myocardial infarction, and the like.

The term "halogen atom," as used herein, means any one of the radio-stable atoms of column 7 of the Periodic Table of the Elements, i.e., fluorine, chlorine, bromine, or iodine, with bromine and chlorine being preferred.

The term "alkyl," as used herein, means any unbranched or branched, substituted or unsubstituted, saturated hydrocarbon, with $C_1$-$C_6$ unbranched, saturated, unsubstituted hydrocarbons being preferred, with methyl, ethyl, isobutyl, and tert-butylpropyl, and pentyl being most preferred. Among the substituted, saturated hydrocarbons, $C_1$-$C_6$ mono- and di- and per-halogen substituted saturated hydrocarbons and amino-substituted hydrocarbons are preferred, with perfluoromethyl, perchloromethyl, perfluoro-tert-butyl, and perchloro-tert-butyl being the most preferred.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. The other above-listed patents also provide standard definitions for the term "substituted" that are well-understood by those of skill in the art.

The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The term "heterocycle" or "heterocyclic" refer to any cyclic compound containing one or more heteroatoms. The substituted aryls, heterocycles and heteroaryls can be substituted with any substituent, including those described above and those known in the art.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring. The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

Certain of the compounds of Formula I-V may be obtained and purified or may be obtained via semi-synthesis from purified compounds as set forth herein. Generally, without being limited thereto, the compounds of Formula II-15, preferably, Formulae II-16, II-17, II-18 and II-19, may be obtained synthetically or by fermentation. Exemplary fermentation procedures are provided below. Further, the compounds of Formula II-15, preferably, Formulae II-16, II-17, II-18 and II-19 may be used as starting compounds in order to obtain/synthesize various of the other compounds described herein. Exemplary non-limiting syntheses are provided herein.

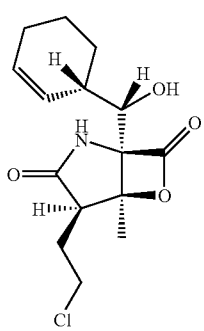

Formula II-16

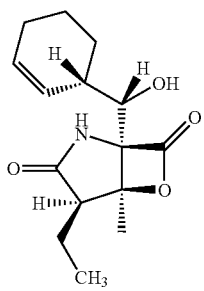

Formula II-17

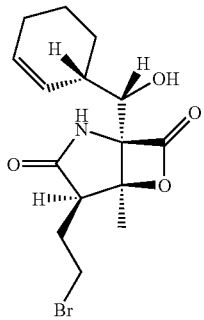

Formula II-18

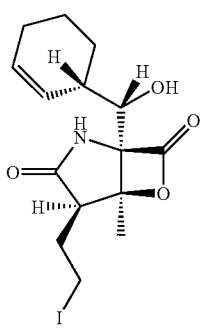

Formula II-19

Formula II-16 is currently produced through a high-yield saline fermentation (~200 mg/L) and modifications of the conditions has yielded new analogs in the fermentation extracts. FIG. 1 shows the chemical structure of II-16. Additional analogs can be generated through directed biosynthesis. Directed biosynthesis is the modification of a natural product by adding biosynthetic precursor analogs to the fermentation of producing microorganisms (Lam, et al., *J Antibiot* (Tokyo) 44:934 (1991), Lam, et al., *J Antibiot* (*Tokyo*) 54:1 (2001); which is hereby incorporated by reference in its entirety).

Exposing the producing culture to analogs of acetic acid, phenylalanine, valine, butyric acid, shikimic acid, and halogens, preferably, other than chlorine, can lead to the formation of new analogs. The new analogs produced can be easily detected in crude extracts by HPLC and LC-MS. For example, after manipulating the medium with different concentrations of sodium bromide, a bromo-analog, Formula II-18, was successfully produced in shake-flask culture at a titer of 14 mg/L.

A second approach to generate new analogs is through biotransformation. Biotransformation reactions are chemical reactions catalyzed by enzymes or whole cells containing these enzymes. Zaks, A., *Curr Opin Chem Biol* 5:130 (2001). Microbial natural products are ideal substrates for biotransformation reactions as they are synthesized by a series of enzymatic reactions inside microbial cells. Riva, S., *Curr Opin Chem Biol* 5:106 (2001).

Given the structure of the described compounds, including those of Formula II-15, for example, the possible biosynthetic origins are acetyl-CoA, ethylmalonyl-CoA, phenylalanine and chlorine. Ethylmalonyl-CoA is derived from butyryl-CoA, which can be derived either from valine or crotonyl-CoA. Liu, et al., *Metab Eng* 3:40 (2001). Phenylalanine is derived from shikimic acid.

Production of Compounds of Formulae II-16, II-17, and II-18

The production of compounds of Formulae II-16, II-17, and II-18 may be carried out by cultivating strain CNB476 in a suitable nutrient medium under conditions described herein, preferably under submerged aerobic conditions, until a substantial amount of compounds are detected in the fermentation; harvesting by extracting the active components from the fermentation broth with a suitable solvent; concentrating the solvent containing the desired components; then subjecting the concentrated material to chromatographic separation to isolate the compounds from other metabolites also present in the cultivation medium.

Figure 2:
FIG. 2 shows the pan-tropical distribution of the *Salinospora*. "X" denotes *Salinospora* collection sites.
Figure 3:
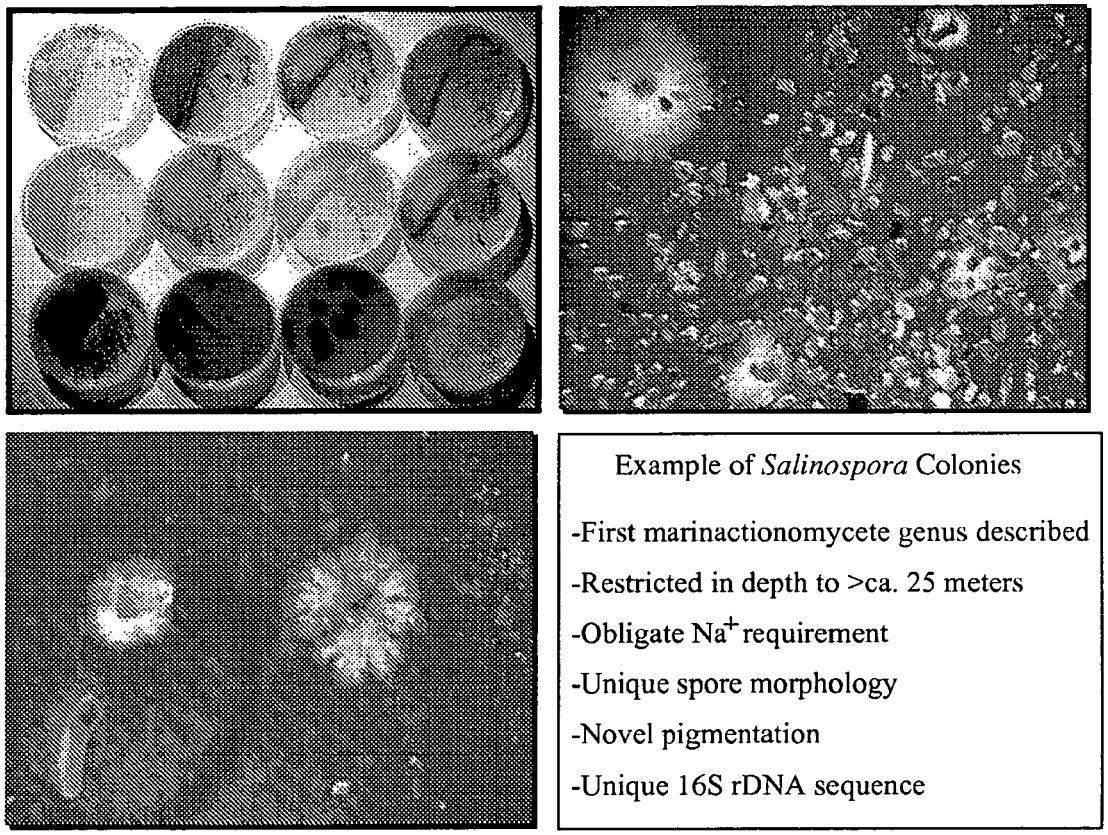
FIG. 3 shows colonies of *Salinospora*.
Figure 4:
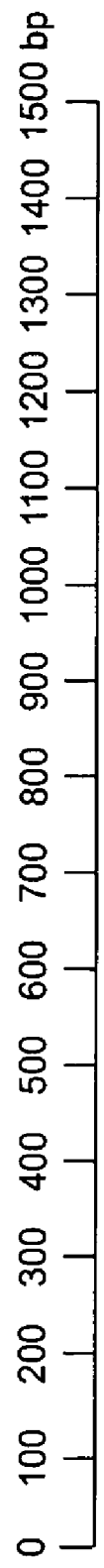
FIG. 4 shows the typical 16S rDNA sequence of the *Salinospora*. Bars represent characteristic signature nucleotides of the *Salinospora* that separate them from their nearest relatives.
Figure 4:
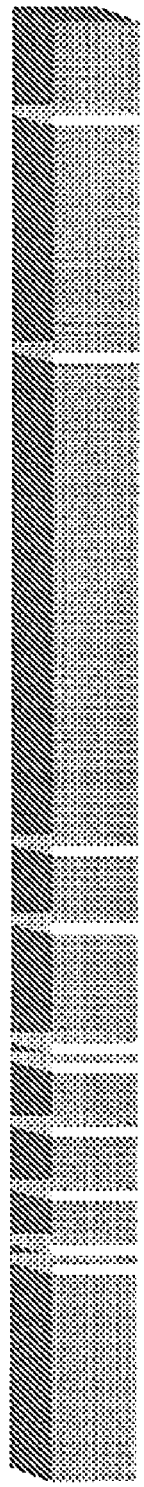

FIG. 2 shows some collection sites worldwide for the culture (CNB476), which is also referred to as *Salinospora*. FIG. 3 shows colonies of *Salinospora*. FIG. 4 shows the typical 16S rDNA sequence of the *Salinospora*. Bars represent characteristic signature nucleotides of the *Salinospora* that separate them from their nearest relatives.

The culture (CNB476) was deposited on Jun. 20, 2003 with the American Type Culture Collection (ATCC) in Rockville, Md. and assigned the ATCC patent deposition number PTA-5275. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce the starting compounds of Formulae II-16, II-17, and II-18.

Fermentation of Strain CNB476

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 400 rpm, preferably at 150 rpm to 250 rpm, for example.

Growth of the microorganisms may be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources may be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cotttonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Biological Activity and Uses of Compounds

Some embodiments relate to methods of treating cancer, inflammation, and infectious diseases, particularly those affecting humans. The methods may include, for example, the step of administering an effective amount of a member of a class of new compounds. Thus, the compounds disclosed herein may be used to treat cancer, inflammation, and infectious disease.

The compounds have various biological activities. For example, the compounds have chemosensitizing activity, anti-microbial, anti-inflammation, and anti-cancer activity.

The compounds have proteasome inhibitory activity. The proteasome inhibitory activity may, in whole or in part, contribute to the ability of the compounds to act as anti-cancer, anti-inflammatory, and anti-microbial agents.

The proteasome is a multisubunit protease that degrades intracellular proteins through its chymotrypsin-like, trypsin-like and peptidylglutamyl-peptide hydrolyzing (PGPH; and also know as the caspase-like activity) activities. The 26S proteasome contains a proteolytic core called the 20S proteasome and two 19S regulatory subunits. The 20S proteasome is responsible for the proteolytic activity against many substrates including damaged proteins, the transcription factor NF-κB and its inhibitor IκB, signaling molecules, tumor suppressors and cell cycle regulators. There are three distinct protease activities within the proteasome: 1) chymotrypsin-like; 2) trypsin-like; and the 3) peptidyl glutamyl peptide hydrolyzing (PGPH) activity.

Figure 5:
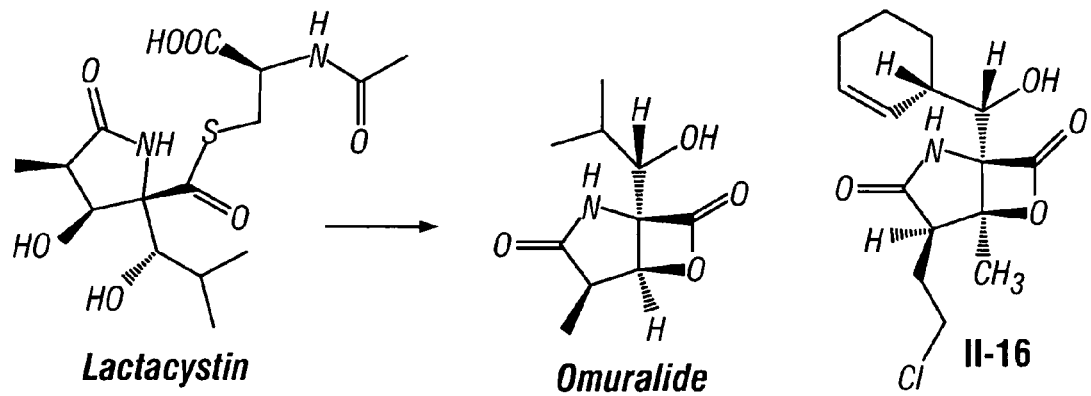
FIG. 5 shows Omuralide, a degradation product of the microbial metabolite Lactacystin. Also shown is a compound of Formula II-16, also referred to as Salinosporamide A.

As an example, compounds of Formula II-16 were more potent ($EC_{50}$ 2 nM) at inhibiting the chymotrypsin-like activity of rabbit muscle proteasomes than Omuralide ($EC_{50}$ 52 nM) and also inhibited the chymotrypsin-like activity of human erythrocyte derived proteasomes ($EC_{50}$~250 μM). FIG. 5 shows omuralide, which is a degradation product of Lactacystin, and it shows a compound of Formula II-16. Compounds of Formula II-16 exhibit a significant preference for inhibiting chymotrypsin-like activity of the proteasome over inhibiting the catalytic activity of chymotrypsin. Compounds of Formula II-16 also exhibit low nM trypsin-like inhibitory activity (~10 nM), but are less potent at inhibiting the PGPH activity of the proteasome ($EC_{50}$~350 nM).

Additional studies have characterized the effects of compounds described herein, including studies of Formula II-16 on the NF-κB/IκB signaling pathway. Treatment of HEK293 cells (human embryonic kidney) with Tumor Necrosis Factor-alpha (TNF-α) induces phosphorylation and proteasome-mediated degradation of IκBα followed by NF-κB activation. To confirm proteasome inhibition, HEK293 cells were pre-treated for 1 hour with compounds of Formula II-16 followed by TNF-α stimulation. Treatment with compounds of Formula II-16 promoted the accumulation of phosphorylated IκBα suggesting that the proteasome-mediated IκBα degradation was inhibited.

Furthermore, a stable HEK293 clone (NF-κB/Luc 293) was generated carrying a luciferase reporter gene under the regulation of 5×NF-κB binding sites. Stimulation of NF-κB/Luc 293 cells with TNF-α increases luciferase activity as a result of NF-κB activation while pretreatment with compounds of Formula II-16 decreases activity. Western blot analyses demonstrated that compounds of Formula II-16 promoted the accumulation of phosphorylated-IκBα and decreased the degradation of total IκBα in the NF-κB/Luc 293 cells. Compounds of Formula II-16 were also shown to increase the levels of the cell cycle regulatory proteins, p21 and p27.

Tumor cells may be more sensitive to proteasome inhibitors than normal cells. Moreover, proteasome inhibition increases the sensitivity of cancer cells to anticancer agents. The cytotoxic activity of the compounds described herein, including Formula II-16, were examined for cytotoxic activity against various cancer cell lines. Formula II-16 was examined, for example, in the National Cancer Institute screen of 60 human tumor cell lines. Formula II-16 exhibited selective cytotoxic activity with a mean $GI_{50}$ value (the concentration to achieve 50% growth inhibition) of less than 10 nM. The greatest potency was observed against SK-MEL-28 melanoma and MDA-MB-235 breast cancer cells [both with $LC_{50}$ (the concentration with 50% cell lethality)<10 nM].

A panel of cell lines including human colorectal (HT-29 and LoVo), prostate (PC3), breast (MDA-MB-231), lung (NCI-H292), ovarian (OVCAR3), acute T-cell leukemia (Jurkat), murine melanoma (B16-F10) and normal human fibroblasts (CCD-27sk) was treated with Salinosporamide A for 48 h to assess cytotoxic activity. HT-29, LoVo, PC3, MDA-MB-231, NCI-H292, OVCAR3, Jurkat, and B16-F10 cells were sensitive with $EC_{50}$ values of 47, 69, 78, 67, 97, 69, 10, and 33 nM, respectively. In contrast, the $EC_{50}$ values for CCD-27sk cells were 196 nM. Treatment of Jurkat cells with Salinosporamide A at the approximate $EC_{50}$ resulted in Caspase-3 activation and cleavage of PARP confirming the induction of apoptosis.

The anti-anthrax activity of the described compounds was evaluated using an in vitro LeTx induced cytotoxicity assay. As one example, the results indicate that Formula II-16 is a potent inhibitor of LeTx-induced cytotoxicity of murine macrophage-like RAW264.7 cells. Treatment of RAW264.7 cells with Formula II-16 resulted in a 10-fold increase in the viability of LeTx-treated cells compared to LeTx treatment alone (average $EC_{50}$ of <4 nM).

Potential Chemosensitizing Effects of Formula II-16

Additional studies have characterized the effects of the compounds described herein on the NF-κB/IκB signaling pathway (see the Examples). In unstimulated cells, the transcription factor nuclear factor-kappa B (NF-κB) resides in the cytoplasm in an inactive complex with the inhibitory protein IκB (inhibitor of NF-κB). Various stimuli can cause IκB phosphorylation by IκB kinase, followed by ubiquitination and degradation by the proteasome. Following the degradation of IκB, NF-κB translocates to the nucleus and regulates gene expression, affecting many cellular processes including inhibition of apoptosis. Chemotherapy agents such as CPT-11 (Irinotecan) can activate NF-κB in human colon cancer cell lines including LoVo cells, resulting in a decreased ability of these cells to undergo apoptosis. Painter, R. B. Cancer Res 38:4445 (1978). Velcade™ is a dipeptidyl boronic acid that inhibits the chymotrypsin-like activity of the proteasome (Lightcap, et al., Clin Chem 46:673 (2000), Adams, et al., Cancer Res 59:2615 (1999), Adams, Curr Opin Oncol 14:628 (2002)) while enhancing the trypsin and PGPH activities. Recently approved as a proteasome inhibitor, Velcade™, (PS-341; Millennium Pharmaceuticals, Inc.) has been shown to be directly toxic to cancer cells and also enhance the cytotoxic activity of CPT-11 in LoVo cells in vitro and in a LoVo xenograft model by inhibiting IκB degradation by the proteasome. Blum, et al., Ann Intern Med 80:249 (1974). In addition, Velcade™ was found to inhibit the expression of proangiogenic chemokines/cytokines Growth Related Oncogene-alpha (GRO-α) and Vascular Endothelial Growth Factor (VEGF) in squamous cell carcinoma, presumably through inhibition of the NF-κB pathway. Dick, et al., J Biol Chem 271:7273 (1996). These data suggest that proteasome inhibition may not only decrease tumor cell survival and growth, but also angiogenesis.

Anti-Anthrax Activity

Another potential application for proteasome inhibitors comes from recent studies on the biodefense Category A agent B. anthracis (anthrax). Anthrax spores are inhaled and lodge in the lungs where they are ingested by macrophages. Within the macrophage, spores germinate, the organism replicates, resulting ultimately in killing of the cell. Before killing occurs, however, infected macrophages migrate to the lymph nodes where, upon death, they release their contents allowing the organism to enter the bloodstream, further replicate, and secrete lethal toxins. Hanna, et al., Proc Natl Acad Sci USA 90:10198 (1993). Anthrax toxins are responsible for the symptoms associated with anthrax. Two proteins that play a key role in the pathogenesis of anthrax are protective antigen (PA, 83 kDa) and lethal factor (LF, 90 kDa) which are collectively known as lethal toxin (LeTx). LF has an enzymatic function, but requires PA to achieve its biological effect. Neither PA or LF cause death individually; however, when combined they cause death when injected intravenously in animals. Kalns, et al., Biochem Biophys Res Commun 297:506 (2002), Kalns, et al., Biochem Biophys Res Commun 292:41 (2002).

Protective antigen, the receptor-binding component of anthrax toxin, is responsible for transporting lethal factor into the host cell. PA oligomerizes into a ring-shaped heptamer (see FIG. 6). Each heptamer, bound to its receptor on the surface of a cell, has the ability to bind up to three molecules of LF. The complex formed between the PA heptamer and LF is taken into the cell by receptor-mediated endocytosis. Following endocytosis, LF is released into the cytosol where it attacks various cellular targets. Mogridge, et al., Biochemistry 41:1079 (2002), Lacy, et al., J Biol Chem 277:3006 (2002), Bradley, et al., Nature 414:225 (2001).

Lethal factor is a zinc dependent metalloprotease, which in the cytosol can cleave and inactivate signaling proteins of the mitogen-activated protein kinase kinase family (MAPKK). Duesbery, et al., Science 280:734 (1998), Bodart, et al., Cell Cycle 1:10 (2002), Vitale, et al., J Appl Microbiol 87:288 (1999), Vitale, et al., Biochem J 352 Pt 3:739 (2000). Of the seven different known MAPK kinases, six have been shown to be cleaved by LF. Within the cell, MAPK kinase pathways transduce various signals involved in cell death, proliferation, and differentiation making these proteins highly significant targets. However, certain inhibitors that prevent LeTx-induced cell death, do not prevent MAPKK cleavage by LF suggesting that this activity is not sufficient for induction of cell death. Kim, et al., J Biol Chem 278:7413 (2003), Lin, et al., Curr Microbiol 33:224 (1996).

Figure 6:
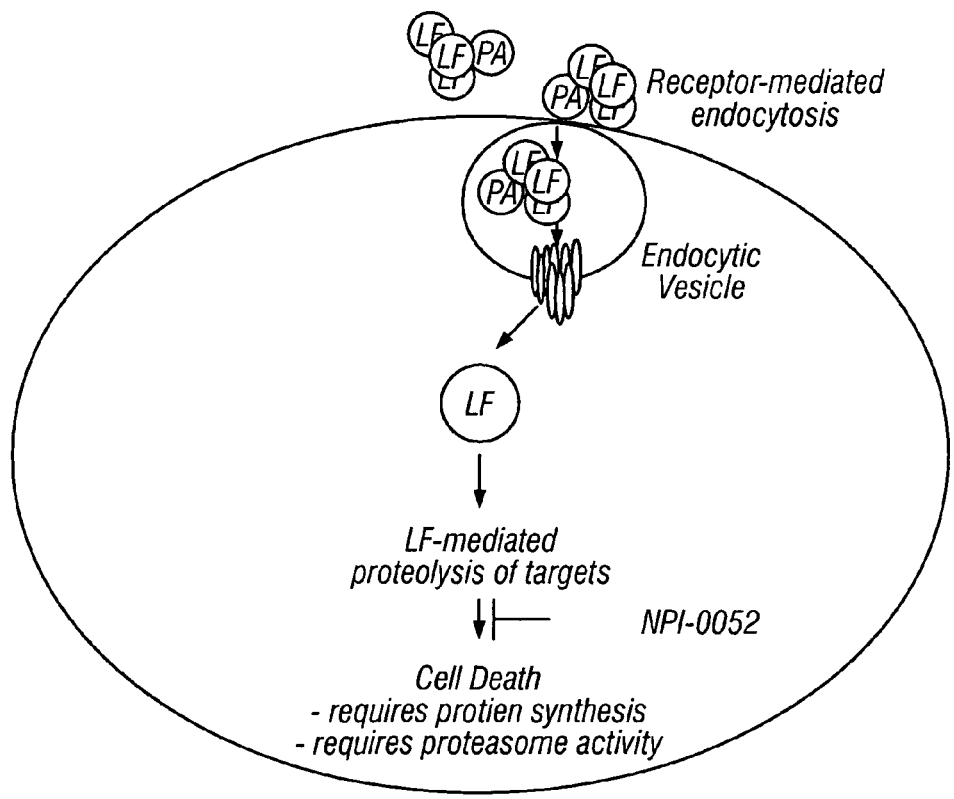
FIG. 6 illustrates lethal toxin-mediated macrophage cytotoxicity. NPI-0052 represents the compound of Formula II-16.

Studies have suggested that inhibition of the proteasome can prevent LeTx-induced cell death. Tang, et al., Infect Immun 67:3055 (1999). Data have shown that proteasome activity is required for LeTx-mediated killing of RAW264.7 macrophage-like cells and that proteasome inhibitors protect RAW264.7 cells from LeTx. Proteasome inhibition did not block MEK1 cleavage, suggesting the LeTx pathway is not blocked upstream of MEK1 cleavage in these studies. Additionally, there is no increase in proteasome activity in cells treated with LeTx. These data suggested that a novel, potent proteasome inhibitor like the compounds described herein, may also prevent LeTx-induced cell death as illustrated in FIG. 6.

The receptor for PA has been identified and is expressed by many cell types. Escuyer, et al., Infect Immun 59:3381 (1991). Lethal toxin is active in a few cell culture lines of macrophages causing cell death within a few hours. Hanna, et al., Proc Natl Acad Sci USA 90:10198 (1993), Kim, et al., J Biol Chem 278:7413 (2003), Lin, et al., Curr Microbiol 33:224 (1996). LeTx can induce both necrosis and apoptosis in mouse macrophage-like RAW264.7 and J774A.1 cells upon in vitro treatment.

The results indicate that the compounds described herein act as a potent inhibitor of LeTx-induced cytotoxicity of murine macrophage-like RAW264.7 cells. Treatment of RAW264.7 cells with, for example, compounds of Formula II-16, resulted in a 10-fold increase in the viability of LeTx-treated cells compared to LeTx treatment alone (average $EC_{50}$ of <4 nM) and therefore provide a valuable therapy for anthrax infections. Formula II-16, for example, promoted survival of RAW264.7 macrophage-like cells in the presence of LeTx indicating that this compound and its derivatives provide a valuable clinical therapeutic for anthrax infection.

Pharmaceutical Compositions

In one embodiment, the compounds disclosed herein are used in pharmaceutical compositions. The compounds preferably can be produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The compositions, particularly those of Formulae I-V, may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. Nos. 5,733,888 (injectable compositions); 5,726,181 (poorly water soluble compounds); 5,707,641 (therapeutically active proteins or peptides); 5,667,809 (lipophilic agents); 5,576,012 (solubilizing polymeric agents); 5,707,615 (anti-viral formulations); 5,683,676 (particulate medicaments); 5,654,286 (topical formulations); 5,688,529 (oral suspensions); 5,445,829 (extended release formulations); 5,653,987 (liquid formulations); 5,641,515 (controlled release formulations) and 5,601,845 (spheroid formulations); all of which are incorporated herein by reference in their entireties.

Further disclosed herein are various pharmaceutical compositions well known in the pharmaceutical art for uses that include intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Ophthalmologica,* 210(2):101-3 (1996)); ophthalmic ointments; ophthalmic suspensions, such as microparticulates, drug-containing small polymeric particles that are suspended in a liquid carrier medium (Joshi, A. 1994 *J Ocul Pharmacol* 10:29-45), lipid-soluble formulations (Alm et al., *Prog. Clin. Biol. Res.,* 312:447-58 (1989)), and microspheres (Mordenti, *Toxicol. Sci.,* 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, $18^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include anti-microbial preservatives and appropriate drug stabilizers. Pharmaceutical formulations for intraauricular delivery include suspensions and ointments for topical application in the ear. Common solvents for such aural formulations include glycerin and water.

When used as an anti-cancer, anti-inflammatory or anti-microbial compound, for example, the compounds of Formulae I-V or compositions including Formulae I-V can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer, anti-inflammatory or anti-microbial can be mixed with additional substances to enhance their effectiveness. In one embodiment, the anti-microbial is combined with an additional anti-microbial. In another embodiment, the anti-microbial is combined with a drug or medicament that is helpful to a patient that is taking anti-microbials.

Methods of Administration

In an alternative embodiment, the disclosed chemical compounds and the disclosed pharmaceutical compositions are administered by a particular method as an anti-microbial. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the compositions that include the described compounds, including those of Formulae I-V, required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above.

All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions may be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-microbial, anti-cancer, or anti-inflammatory agent, the compounds disclosed herein may be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, intradermally, or the like. Controlled release formulations, depot formulations, and infusion pump delivery are similarly contemplated.

The compositions disclosed herein in pharmaceutical compositions may also comprise a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the embodiment, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions may be formulated and administered either systemically or locally. A variety of techniques for formulation and administration may be found in Remington's Pharmaceutical Sciences, 18th ed., Mack Publishing Co., Easton, Pa. (1990).

To formulate the compounds of Formulae I-V as an antimicrobial, an anti-cancer, or an anti-inflammatory agent, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound produced by the method of the embodiment, particularly when the compound is to be administered orally.

The compounds and compositions may be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the embodiment may preferably be administered in the stated amounts continuously by, for example, an intravenous drip. Thus, for the example of a patient weighing 70 kilograms, the preferred daily dose of the active or anti-infective ingredient would be about 0.07 mg/day to about 700 gm/day, and more preferable, 7 mg/day to about 7 grams/day. Nonetheless, as will be understood by those of skill in the art, in certain situations it may be necessary to administer the anti-cancer, anti-inflammatory or the anti-infective compound of the embodiment in amounts that excess, or even far exceed, the above-stated, preferred dosage range to effectively and aggressively treat particularly advanced cancers or infections.

In the case of using the anti-microbial produced by methods of the embodiment as a biochemical test reagent, the compound produced by methods of the embodiment inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the embodiment for use as an anti-microbial, anticancer or anti-tumor compound is generally in the range of about 1 to about 100 µg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

In one embodiment, the method of using a compound as an anti-microbial, anti-cancer or anti-inflammatory involves administering an effective amount of any of the compounds of Formulae I-V or compositions of those compounds. In a preferred embodiment, the method involves administering the compound represented by Formula II, to a patient in need of an anti-microbial, until the need is effectively reduced or more preferably removed.

As will be understood by one of skill in the art, "need" is not an absolute term and merely implies that the patient can benefit from the treatment of the anti-microbial, the anti-cancer, or anti-inflammatory in use. By "patient" what is meant is an organism that can benefit by the use of an anti-microbial, anti-cancer or anti-inflammatory agent. For example, any organism with *B. anthracis, Plasmodium, Leishmania, Trypanosoma*, and the like, may benefit from the application of an anti-microbial that may in turn reduce the amount of microbes present in the patient. As another example, any organism with cancer, such as, a colorectal carcinoma, a prostate carcinoma, a breast adenocarcinoma, a non-small cell lung carcinoma, an ovarian carcinoma, multiple myelomas, a melanoma, and the like, may benefit from the application of an anti-cancer agent that may in turn reduce the amount of cancer present in the patient. Furthermore, any organism with an inflammatory conditions, such as, rheumatoid arthritis, asthma, multiple sclerosis, psoriasis, stroke, myocardial infarction, and the like, may benefit from the application of an anti-inflammatory that may in turn reduce the amount of cells associated with the inflammatory response present in the patient. In one embodiment, the patient's health may not require that an anti-microbial, anti-cancer, or anti-inflammatory be administered, however, the patient may still obtain some benefit by the reduction of the level of microbes, cancer cells, or inflammatory cells present in the patient, and thus be in need. In one embodiment, the anti-microbial or anti-cancer agent is effective against one type of microbe or cancer, but not against other types; thus, allowing a high degree of selectivity in the treatment of the patient. In other embodiments, the anti-inflammatory may be effective against inflammatory conditions characterized by different cells associated with the inflammation. In choosing such an anti-microbial, anti-cancer or anti-inflammatory agent, the methods and results disclosed in the Examples may be useful. In an alternative embodiment, the anti-microbial may be effective against a broad spectrum of microbes, preferably a broad spectrum of foreign, and, more preferably, harmful bacteria, to the host organism. In embodiments, the anti-cancer and/or anti-inflammatory agent may be effective against a broad spectrum of cancers and inflammatory conditions/cells/substances. In yet another embodiment, the anti-microbial is effective against all microbes, even those native to the host. Examples of microbes that may be targets of anti-microbials, include, but are not limited to, *B. anthracis, Plasmodium, Leishmania, Trypanosoma*, and the like. In still further embodiments, the anti-cancer agent is effective against a broad spectrum of cancers or all cancers. Examples of cancers, against which the compounds may be effective include a colorectal carcinoma, a prostate carcinoma, a breast adenocarcinoma, a non-small cell lung carcinoma, an ovarian carcinoma, multiple myelomas, a melanoma, and the like. Exemplary inflammatory conditions against which the agents are effective include rheumatoid arthritis, asthma, multiple sclerosis, psoriasis, stroke, myocardial infarction, and the like.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

"Anti-microbial" refers to a compound that reduces the likelihood of survival of microbes, or blocks or alleviates the deleterious effects of a microbe. In one embodiment, the likelihood of survival is determined as a function of an individual microbe; thus, the anti-microbial will increase the chance that an individual microbe will die. In one embodiment, the likelihood of survival is determined as a function of a population of microbes; thus, the anti-microbial will increase the chances that there will be a decrease in the population of microbes. In one embodiment, anti-microbial means antibiotic or other similar term. Such anti-microbials are capable of blocking the harmful effects, destroying or suppressing the growth or reproduction of microorganisms, such as bacteria. For example, such antibacterials and other anti-microbials are described in Antibiotics, Chemotherapeutics and Antibacterial Agents for Disease Control (M. Grayson, editor, 1982), and E. Gale et al., The Molecular Basis of Antibiotic Action 2d edition (1981). In another embodiment, an anti-microbial will not change the likelihood of survival, but will change the chances that the microbes will be harmful to the host in some way. For instance, if the microbe secretes a substance that is harmful to the host, the anti-microbial may act upon the microbe to stop the secretion or may counteract or block the harmful effect. In one embodiment, an anti-microbial, while, increasing the likelihood that the microbe(s) will die, is minimally harmful to the surrounding, non-microbial, cells. In an alternative embodiment, it is not important how harmful the anti-microbial is to surrounding, nonmicrobial, cells, as long as it reduces the likelihood of survival of the microbe.

"Anti-cancer agent" refers to a compound or composition including the compound that reduces the likelihood of survival of a cancer cell. In one embodiment, the likelihood of survival is determined as a function of an individual cancer cell; thus, the anti-cancer agent will increase the chance that an individual cancer cell will die. In one embodiment, the likelihood of survival is determined as a function of a population of cancer cells; thus, the anti-cancer agent will increase the chances that there will be a decrease in the population of cancer cells. In one embodiment, anti-cancer agent means chemotherapeutic agent or other similar term.

A "chemotherapeutic agent" is a chemical compound useful in the treatment of a neoplastic disease, such as cancer. Examples of chemotherapeutic agents include alkylating agents, such as a nitrogen mustard, an ethyleneimine and a methylmelamine, an alkyl sulfonate, a nitrosourea, and a triazene, folic acid antagonists, anti-metabolites of nucleic acid metabolism, antibiotics, pyrimidine analogs, 5-fluorouracil, cisplatin, purine nucleosides, amines, amino acids, triazol nucleosides, corticosteroids, a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gouadotropin-releasing hormone analog. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins, Melphalan, and other related nitrogen mustards. Also included in this definition are hormonal agents that act to regulate or inhibit hormone action on tumors, such as tamoxifen and onapristone.

The anti-cancer agent may act directly upon a cancer cell to kill the cell, induce death of the cell, to prevent division of the cell, and the like. Alternatively, the anti-cancer agent may indirectly act upon the cancer cell by limiting nutrient or blood supply to the cell, for example. Such anti-cancer agents are capable of destroying or suppressing the growth or reproduction of cancer cells, such as a colorectal carcinoma, a prostate carcinoma, a breast adenocarcinoma, a non-small cell lung carcinoma, an ovarian carcinoma, multiple myelomas, a melanoma, and the like.

A "neoplastic disease" or a "neoplasm" refers to a cell or a population of cells, including a tumor or tissue (including cell suspensions such as bone marrow and fluids such as blood or serum), that exhibits abnormal growth by cellular proliferation greater than normal tissue. Neoplasms can be benign or malignant.

An "inflammatory condition" includes, for example, conditions such as ischemia, septic shock, autoimmune diseases, rheumatoid arthritis, inflammatory bowel disease, systemic lupus eythematosus, multiple sclerosis, asthma, osteoarthritis, osteoporosis, fibrotic diseases, dermatosis, including psoriasis, atopic dermatitis and ultraviolet radiation (UV)-induced skin damage, psoriatic arthritis, alkylosing spondylitis, tissue and organ rejection, Alzheimer's disease, stroke, atherosclerosis, restenosis, diabetes, glomerulonephritis, cancer, Hodgkins disease, cachexia, inflammation associated with infection and certain viral infections, including acquired immune deficiency syndrome (AIDS), adult respiratory distress syndrome and Ataxia Telangiestasia.

In one embodiment, a described compound, preferably a compound having the Formulae I-V, including those as described herein, is considered an effective anti-microbial, anti-cancer, or anti-inflammatory if the compound can influence 10% of the microbes, cancer cells, or inflammatory cells, for example. In a more preferred embodiment, the compound is effective if it can influence 10 to 50% of the microbes, cancer cells, or inflammatory cells. In an even more preferred embodiment, the compound is effective if it can influence 50-80% of the microbes, cancer cells, or inflammatory cells. In an even more preferred embodiment, the compound is effective if it can influence 80-95% of the microbes, cancer cells, or inflammatory cells. In an even more preferred embodiment, the compound is effective if it can influence 95-99% of the microbes, cancer cells, or inflammatory cells. "Influence" is defined by the mechanism of action for each compound. Thus, for example, if a compound prevents the reproduction of microbes, then influence is a measure of prevention of reproduction. Likewise, if a compound destroys microbes, then influence is a measure of microbe death. Also, for example, if a compound prevents the division of cancer cells, then influence is a measure of prevention of cancer cell division. Further, for example, if a compound prevents the proliferation of inflammatory cells, then influence is a measure of prevention of inflammatory cell proliferation. Not all mechanisms of action need be at the same percentage of effectiveness. In an alternative embodiment, a low percentage effectiveness may be desirable if the lower degree of effectiveness is offset by other factors, such as the specificity of the compound, for example. Thus a compound that is only 10% effective, for example, but displays little in the way of harmful side-effects to the host, or non-harmful microbes or cells, can still be considered effective.

In one embodiment, the compounds described herein are administered simply to remove microbes, cancer cells or inflammatory cells, and need not be administered to a patient. For example, in situations where microbes can present a problem, such as in food products, the compounds described herein can be administered directly to the products to reduce the risk of microbes in the products. Alternatively, the compounds can be used to reduce the level of microbes present in the surrounding environment, such working surfaces. As another example, the compounds can be administered ex vivo to a cell sample, such as a bone marrow or stem cell transplant to ensure that only non-cancerous cells are introduced into the recipient. After the compounds are administered they may optionally be removed. This may be particularly desirable in situations where work surfaces or food products may come into contact with other surfaces or organisms that could risk being harmed by the compounds. In an alternative embodiment, the compounds may be left in the food products or on the work surfaces to allow for a more protection. Whether or not this is an option will depend upon the relative needs of the situation and the risks associated with the compound, which in part can be determined as described in the Examples below.

The following non-limiting examples are meant to describe the preferred embodiments of the methods. Variations in the details of the particular methods employed and in the precise chemical compositions obtained will undoubtedly be appreciated by those of skill in the art.

EXAMPLES

Example 1

Fermentation of Compound of Formulae II-16, II-20, and II-24C

Strain CNB476 was grown in a 500-ml flask containing 100 ml of vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Four ml each of the first seed culture was inoculated into three 500-ml flasks containing of 100 ml of the vegetative medium. The second seed cultures were incubated at 28 degree C. and 250 rpm on a rotary shaker for 2 days. Four ml each of the second seed culture was inoculated into thirty-five 500-ml flasks containing of 100 ml of the vegetative medium. The third seed cultures were incubated at 28 degree and 250 rpm on a rotary shaker for 2 days. Four ml each of the third seed culture was inoculated into four hundred 500-ml flasks containing 100 ml of the production medium consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on roatry shakers for 1 day. Approximately 2 to 3 grams of sterile Amberlite XAD-7 resin were added to the production cultures. The production cultures were further incubated at 28 degree C. and 250 rpm on rotary shakers for 5 days. The culture broth was filtered through cheese cloth to recover the Amberlite XAD-7 resin. The resin was extracted with 2 times 6 liters ethyl acetate followed by 1 time 1.5 liters ethyl acetate. The combined extracts were dried in vacuo. The dried extract, containing 3.8 grams the compound of Formula II-16 and lesser quantities of compounds of formulae II-20 and II-24C, was then processed for the recovery of the compounds of Formula II-16, II-20 and II-24C.

Example 2

Purification of Compound of Formulae II-16, II-20 and II-24C

The pure compounds of Formulae II-16, II-20 and II-24C were obtained by flash chromatography followed by HPLC. Eight grams crude extract containing 3.8 grams of the compound of Formula II-16 and lesser quantities of II-20 and II-24C was processed by flash chromatography using Biotage Flash40i system and Flash 40M cartridge (KP-Sil Silica, 32-63 µm, 90 grams). The flash chromatography was developed by the following step gradient:
1. Hexane (1 L)
2. 10% Ethyl acetate in hexane (1 L)
3. 20% Ethyl acetate in hexane, first elution (1 L)
4. 20% Ethyl acetate in hexane, second elution (1 L)
5. 20% Ethyl acetate in hexane, third elution (1 L)
6. 25% Ethyl acetate in hexane (1 L)
7. 50% Ethyl acetate in hexane (1 L)
8. Ethyl acetate (1 L)

Fractions containing the compound of Formula II-16 in greater or equal to 70% UV purity by HPLC were pooled and subject to HPLC purification, as described below, to obtain II-16, along with II-20 and II-24C, each as pure compounds

| | |
|---|---|
| Column | Phenomenex Luna 10u Silica |
| Dimensions | 25 cm × 21.2 mm ID |
| Flow rate | 25 ml/min |
| Detection | ELSD |
| Solvent | Gradient of 24% EtOAc/hexane for 19 min, 24% EtOAc/hexane to 100% EtOAc in 1 min, then 100% EtOAc for 4 min |

The fraction enriched in compound of Formula II-16 (described above; ~70% pure with respect to II-16) was dissolved in acetone (60 mg/ml). Aliquots (950 ul) of this solution were injected onto a normal-phase HPLC column using the conditions described above. The compound of Formula II-16 eluted at about 14 minutes, and minor compounds II-24C and II-20 eluted at 11 and 23 minutes, respectively. Fractions containing II-16, II-24C, and II-20 were pooled based on composition of compound present. Fractions containing the desired compounds were concentrated under reduced pressure to yield pure compound of Formula II-16, as well as separate fractions containing II-24C and II-20, which were further purified as described below.

Sample containing II-24C (70 mg) was dissolved in acetonitrile at a concentration of 10 mg/ml, and 500 µl was loaded on an HPLC column of dimensions 21 mm i.d. by 15 cm length containing Eclipse XDB-C18 support. The solvent gradient increased linearly from 15% acetonitrile/85% water to 100% acetonitrile over 23 minutes at a flow rate of 14.5 ml/min. The solvent composition was held at 100% acetonitrile for 3 minutes before returning to the starting solvent mixture. Compound II-24C eluted at 19 minutes as a pure compound under these conditions.

To obtain pure compound II-20, the enriched samples generated from the preparative HPLC method described above were triturated with EtOAc to remove minor lipophilic impurities. The resulting sample contained compound II-20 in >95% purity.

Compound of Formula II-16: UV (Acetonitrile/$H_2O$) $\lambda_{max}$ 225(sh) nm. Low Res. Mass: m/z 314 (M+H), 336 (M+Na)

Figure 7:
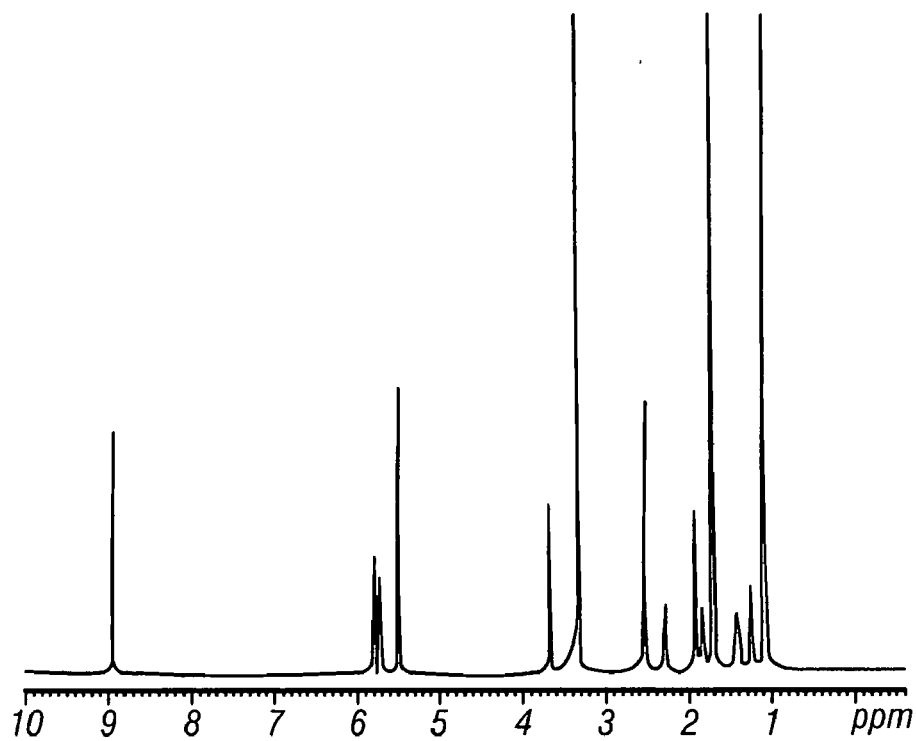
FIG. 7 depicts the 1H NMR spectrum of a compound having structure Formula II-20.

Compound of Formula II-20: UV (Acetonitrile/$H_2O$) $\lambda_{max}$ 225(sh) nm. Low Res. Mass: m/z 266 (M+H). FIG. 7 depicts the 1H NMR spectrum of a compound having the structure of Formula II-20.

Figure 8:
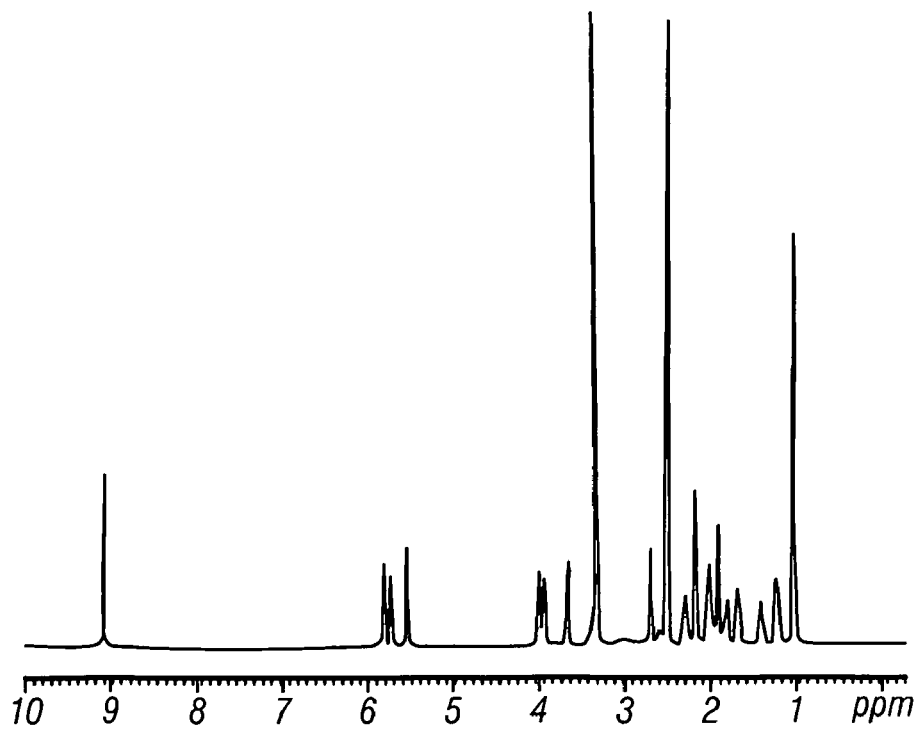
FIG. 8 depicts the 1H NMR spectrum of a compound having structure Formula II-24C.

Compound of Formula II-24C: UV (Acetonitrile/$H_2O$) $\lambda_{max}$ 225(sh) nm. Low Res. Mass: m/z 328 (M+H), 350 (M+Na). FIG. 8 depicts the 1H NMR spectrum of a compound having the structure of Formula II-24C.

Example 3

Fermentation of Compounds of Formulae II-17 and II-18

Strain CNB476 was grown in a 500-ml flask containing 100 ml of the first vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into a 500-ml flask containing 100 ml of the second vegetative medium consisting of the following per liter of deionized water: starch, 10 g; yeast extract, 4 g; peptone, 2 g; ferric sulfate, 40 mg; potassium bromide, 100 mg; calcium carbonate, 1 g; and sodium bromide, 30 g. The second seed cultures were incubated at 28° C. for 7 days on a rotary shaker operating at 250 rpm. Approximately 2 to 3 gram of sterile Amberlite XAD-7 resin were added to the second seed culture. The second seed culture was further incubated at 28° C. for 2 days on a rotary shaker operating at 250 rpm. Five ml of the second seed culture was inoculated into a 500-ml flask containing 100 ml of the second vegetative medium. The third seed culture was incubated at 28° C. for 1 day on a rotary shaker operating at 250 rpm. Approximately 2 to 3 gram of sterile Amberlite XAD-7 resin were added to the third seed culture. The third seed culture was further incubated at 28° C. for 2 days on a rotary shaker operating at 250 rpm. Five ml of the third culture was inoculated into a 500-ml flask containing 100 ml of the second vegetative medium. The fourth seed culture was incubated at 28° C. for 1 day on a rotary shaker operating at 250 rpm. Approximately 2 to 3 gram of sterile Amberlite XAD-7 resin were added to the fourth seed culture. The fourth seed culture was further incubated at 28° C. for 1 day on a rotary shaker operating at 250 rpm. Five ml each of the fourth seed culture was inoculated into ten 500-ml flasks containing 100 ml of the second vegetative medium. The fifth seed cultures were incubated at 28° C. for 1 day on a rotary shaker operating at 250 rpm. Approximately 2 to 3 grams of sterile Amberlite XAD-7 resin were added to the fifth seed cultures. The fifth seed cultures were further incubated at 28° C. for 3 days on a rotary shaker operating at 250 rpm. Four ml each of the fifth seed culture was inoculated into one hundred and fifty 500-ml flasks containing 100 ml of the production medium having the same composition as the second vegetative medium. Approximately 2 to 3 grams of sterile Amberlite XAD-7 resin were also added to the production culture. The production cultures were incubated at 28° C. for 6 day on a rotary shaker operating at 250 rpm. The culture broth was filtered through cheese cloth to recover the Amberlite XAD-7 resin. The resin was extracted with 2 times 3 liters ethyl acetate followed by 1 time 1 liter ethyl acetate. The combined extracts were dried in vacuo. The dried extract, containing 0.42 g of the compound Formula II-17 and 0.16 gram the compound of Formula II-18, was then processed for the recovery of the compounds.

Example 4

Purification of Compounds of Formula II-17 and II-18

The pure compounds of Formula II-17 and II-18 were obtained by reversed-phase HPLC as described below:

| Column | ACE 5 C18-HL |
| Dimensions | 15 cm × 21 mm ID |
| Flow rate | 14.5 ml/min |
| Detection | 214 nm |
| Solvent | Gradient of 35% Acetonitrile/65% $H_2O$ to 90% Acetonitrile/10% $H_2O$ over 15 min |

Crude extract (100 mg) was dissolved in 15 ml of acetonitrile. Aliquots (900 ul) of this solution were injected onto a reversed-phase HPLC column using the conditions described above. Compounds of Formulae II-17 and II-18 eluted at 7.5 and 9 minutes, respectively. Fractions containing the pure compounds were first concentrated using nitrogen to remove organic solvent. The remaining solution was then frozen and lyophilized to dryness.

Figures 48, 49:
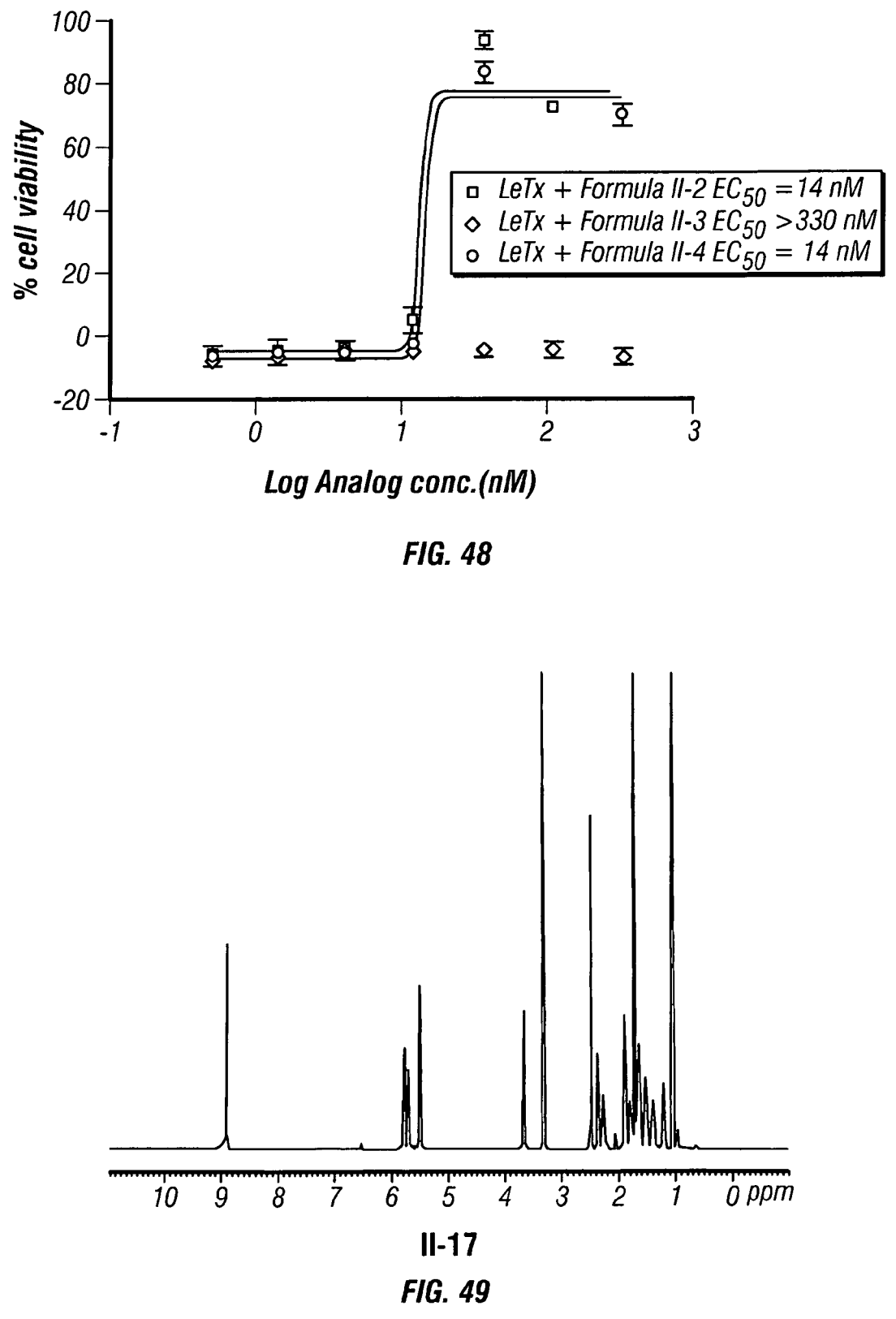

Compound of Formula II-17: UV (Acetonitrile/$H_2O$) $\lambda_{max}$ 225(sh) nm. High Res. Mass (APCI): m/z 280.156 (M+H), $\Delta_{calc}$=2.2 ppm, $C_{15}H_{22}NO_4$. FIG. 49 depicts the $^1$H NMR spectrum of a compound having the structure of Formula II-17.

Figure 50:
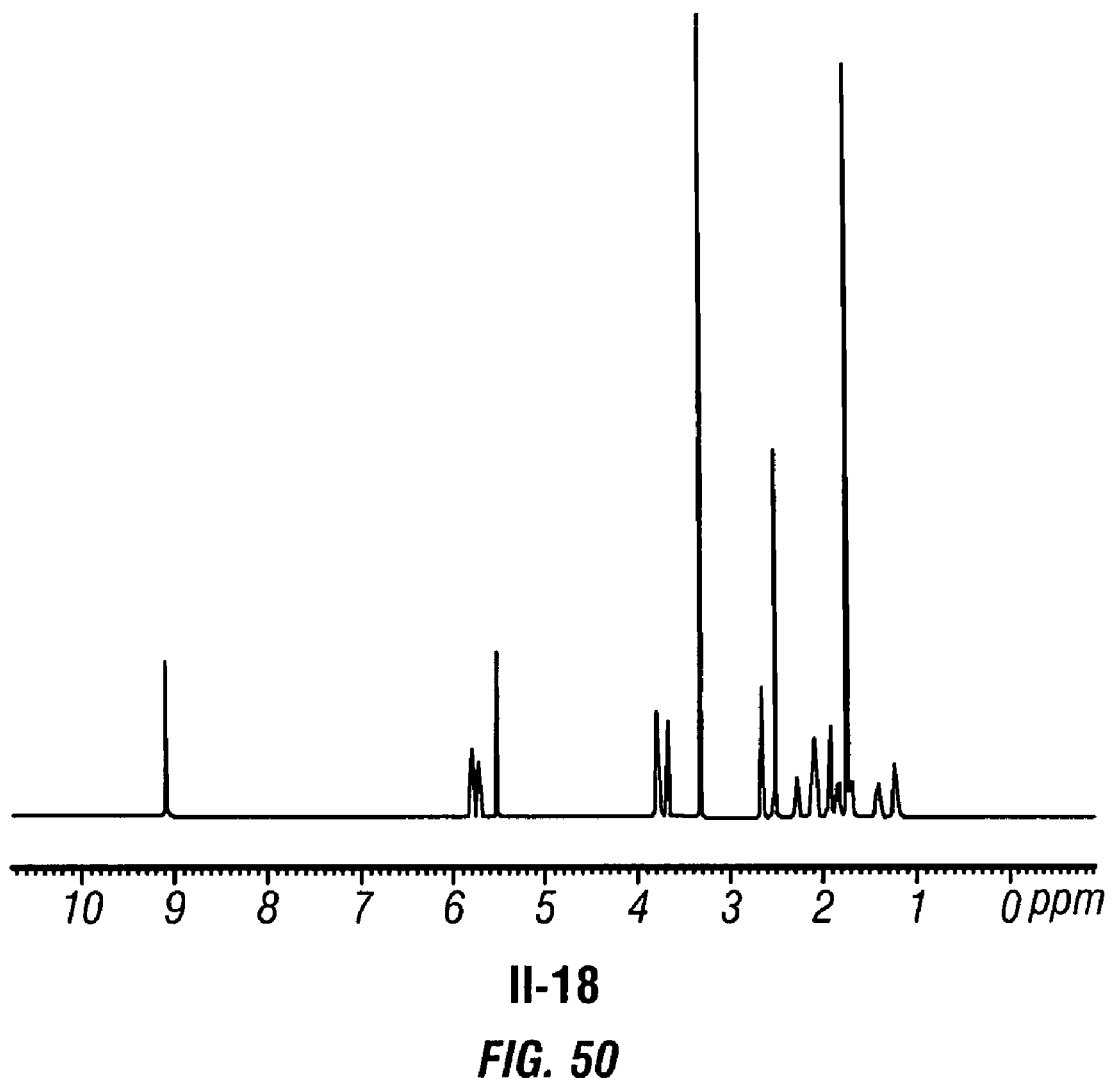
FIG. 50 depicts the 1H NMR spectrum of a compound having structure Formula II-18.

Compound of Formula II-18: UV (Acetonitrile/$H_2O$) $\lambda_{max}$ 225(sh) nm. High Res. Mass (APCI): m/z 358.065 (M+H), $\Delta_{calc}$=–1.9 ppm, $C_{15}H_{21}NO_4Br$. FIG. 50 depicts the $^1$H NMR spectrum of a compound having the structure of Formula II-18.

Example 5

Preparation of Compound of Formula II-19 from II-16

Figure 9:
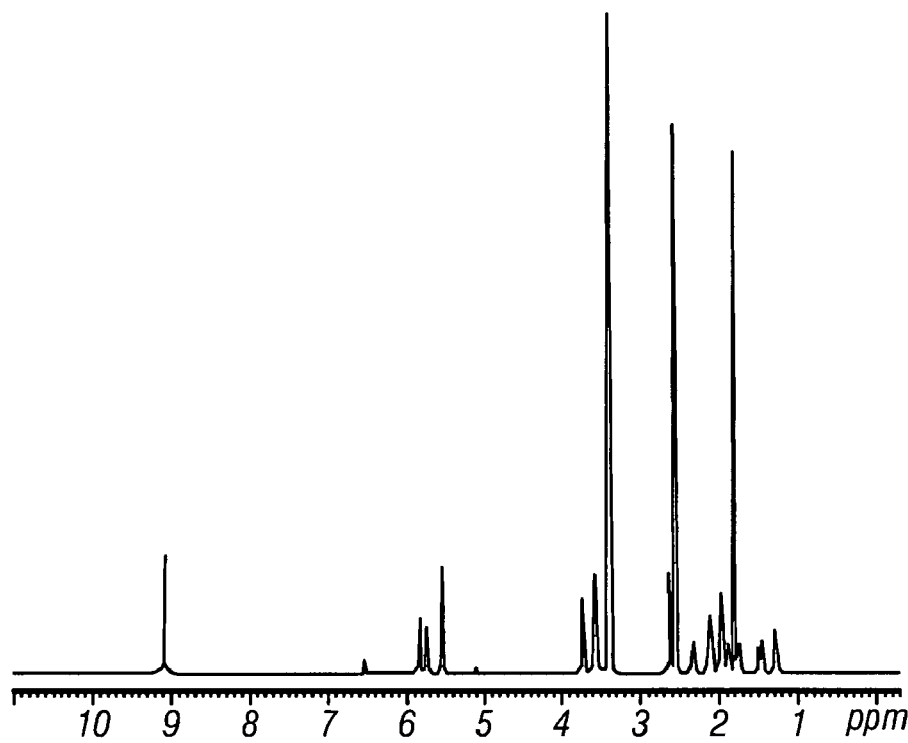
FIG. 9 depicts the 1H NMR spectrum of a compound having structure Formula II-19.

A sample of compound of Formula II-16 (250 mg) was added to an acetone solution of sodium iodide (1.5 g in 10 ml) and the resulting mixture stirred for 6 days. The solution was then filtered through a 0.45 micron syringe filter and injected directly on a normal phase silica HPLC column (Phenomenex Luna 10u Silica, 25 cm×21.2 mm) in 0.95 ml aliquots. The HPLC conditions for the separation of compound formula II-19 from unreacted II-16 employed an isocratic HPLC method consisting of 24% ethyl acetate and 76% hexane, in which the majority of compound II-19 eluted 2.5 minutes before compound II-16. Equivalent fractions from each of 10 injections were pooled to yield 35 mg compound II-19. Compound II-19: UV (Acetonitrile/$H_2O$) 225 (sh), 255 (sh) nm; ESMS, m/z 406.0 (M+H); $^1$H NMR in DMSO-$d_6$ (see FIG. 9).

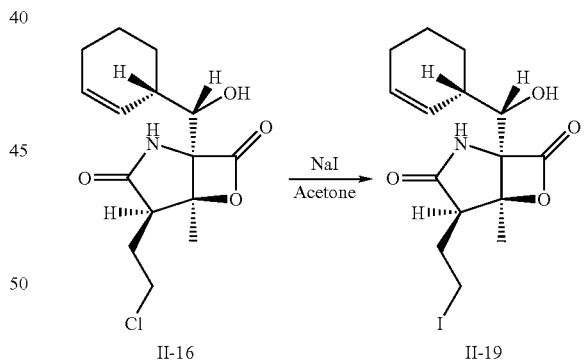

Example 6

Synthesis of the Compounds of Formulae II-2, II-3, and II-4

Compounds of Formulae II-2, II-3 and II-4 can be synthesized from compounds of Formulae II-16, II-17 and II-18, respectively, by catalytic hydrogenation.

51

Exemplary Depiction of Synthesis

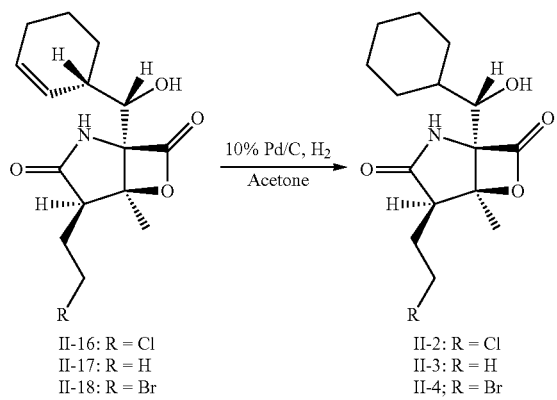

II-16: R = Cl
II-17: R = H
II-18: R = Br

II-2: R = Cl
II-3: R = H
II-4: R = Br

Example 6A

Catalytic Hydrogenation of Compound of Formula II-16

Figure 10:
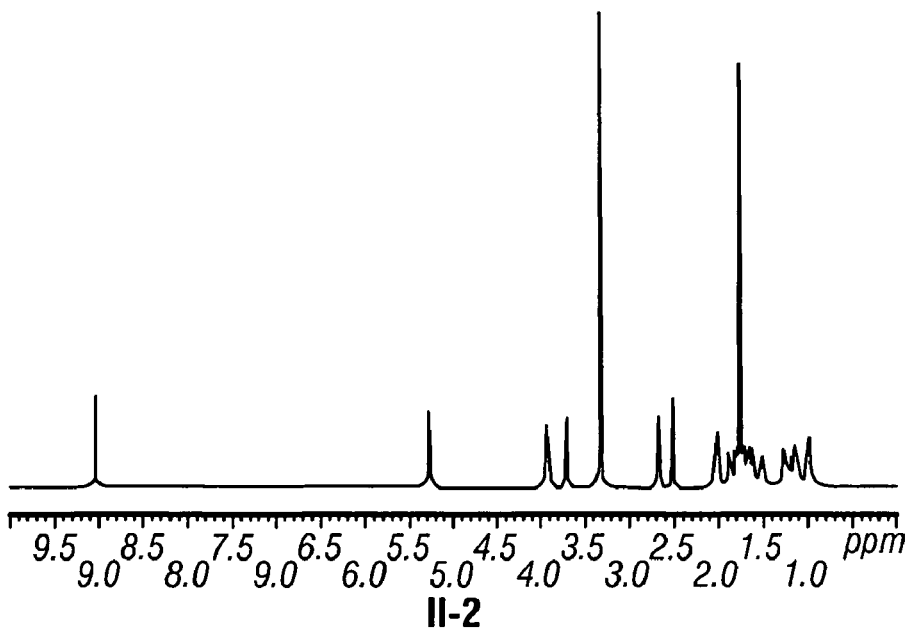
FIG. 10 depicts the 1H NMR spectrum of a compound having structure Formula II-2.
Figure 11:
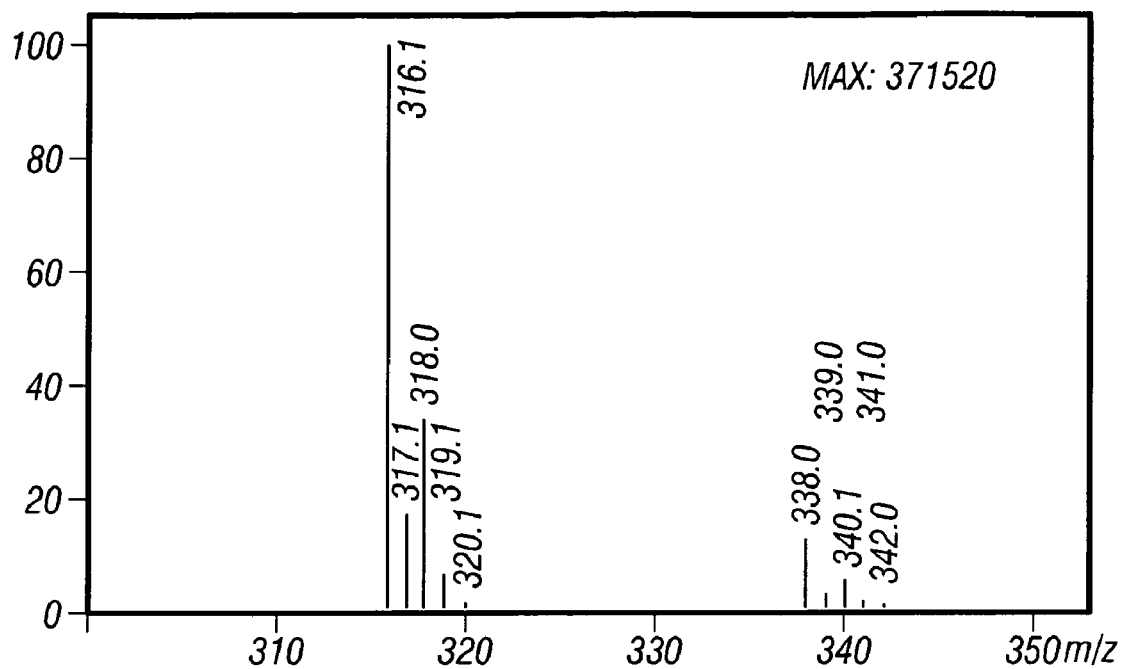
FIG. 11 depicts the mass spectrum of a compound having structure Formula II-2.

Compound of Formula II-16 (10 mg) was dissolved in acetone (5 mL) in a scintillation vial (20 mL) to which was added the 10% (w/w) Pd/C (1-2 mg) and a magnetic stirrer bar. The reaction mixture was stirred in a hydrogen atmosphere at room temperature for about 15 hours. The reaction mixture was filtered through a 3 cc silica column and washed with acetone. The filtrate was filtered again through 0.2 µm Gelman Acrodisc to remove any traces of catalyst. The solvent was evaporated off from filtrate under reduced pressure to yield the compound of Formula II-2 as a pure white powder: UV (acetonitrile/H$_2$O): $\lambda_{max}$ 225 (sh) nm. FIG. 10 depicts the NMR spectrum of the compound of Formula II-2 in DMSO-d$_6$. FIG. 11 depicts the low resolution mass spectrum of the compound of Formula II-2: m/z 316 (M+H), 338 (M+Na).

Example 6B

Catalytic Hydrogenation of Compound of Formula II-17

Compound of Formula II-17 (5 mg) was dissolved in acetone (3 mL) in a scintillation vial (20 mL) to which was added the 10% (w/w) Pd/C (about 1 mg) and a magnetic stirrer bar. The reaction mixture was stirred in a hydrogen atmosphere at room temperature for about 15 hours. The reaction mixture was filtered through a 0.2 µm Gelman Acrodisc to remove the catalyst. The solvent was evaporated off from filtrate to yield the compound of Formula II-3 as a white powder which was purified by normal phase HPLC using the following conditions:

| Column: | Phenomenex Luna 10u Silica |
|---|---|
| Dimensions: | 25 cm × 21.2 mm ID |
| Flow rate: | 14.5 ml/min |
| Detection: | ELSD |
| Solvent: | 5% to 60% EtOAc/Hex for 19 min, 60 to 100% EtOAc in 1 min, then 4 min at 100% EtOAc |

Figure 12:
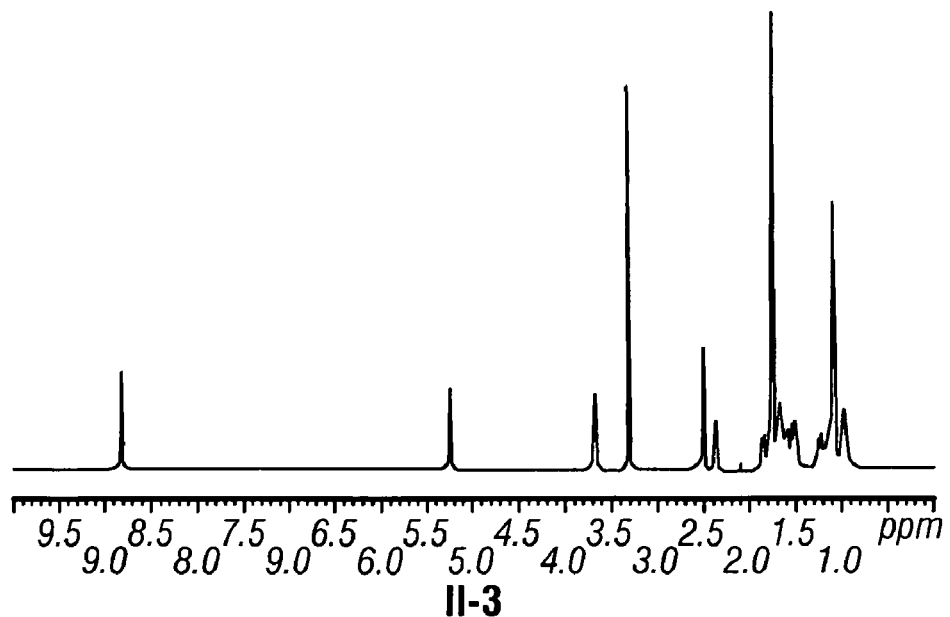
FIG. 12 depicts the 1H NMR spectrum of a compound having structure Formula II-3.

Compound of Formula II-3 eluted at 22.5 min as a pure compound: UV (acetonitrile/H$_2$O): $\lambda_{max}$ 225 (sh) nm. FIG. 12

Figure 13:
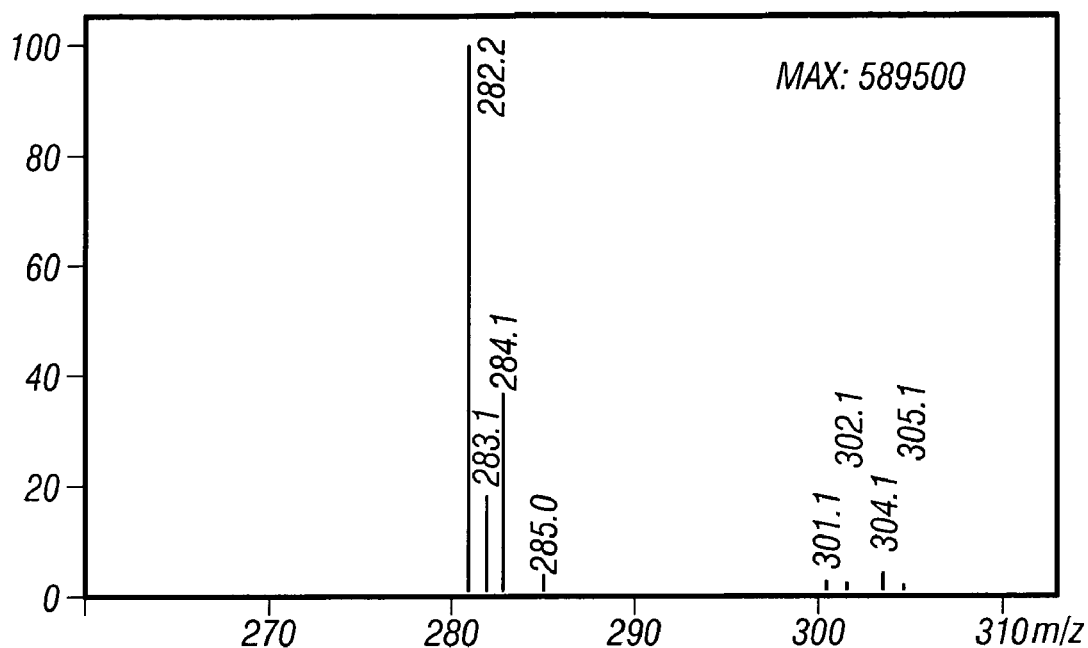
FIG. 13 depicts the mass spectrum of a compound having structure Formula II-3.

52 depicts the NMR spectrum of the compound of Formula II-3 in DMSO-d$_6$. FIG. 13 depicts the low resolution mass spectrum of the compound of Formula II-3: m/z 282 (M+H), 304 (M+Na).

Example 6C

Catalytic Hydrogenation of Compound of Formula II-18

3.2 mg of compound of Formula II-18 was dissolved in acetone (3 mL) in a scintillation vial (20 mL) to which was added the 10% (w/w) Pd/C (about 1 mg) and a magnetic stirrer bar. The reaction mixture was stirred in hydrogen atmosphere at room temperature for about 15 hours. The reaction mixture was filtered through a 0.2 µm Gelman Acrodisc to remove the catalyst. The solvent was evaporated off from filtrate to yield the compound of Formula II-4 as a white powder which was further purified by normal phase HPLC using the following conditions:

| Column: | Phenomenex Luna 10u Silica |
|---|---|
| Dimensions: | 25 cm × 21.2 mm ID |
| Flow rate: | 14.5 ml/min |
| Detection: | ELSD |
| Solvent: | 5% to 80% EtOAc/Hex for 19 min, 80 to 100% EtOAc in 1 min, then 4 min at 100% EtOAc |

Figure 14:
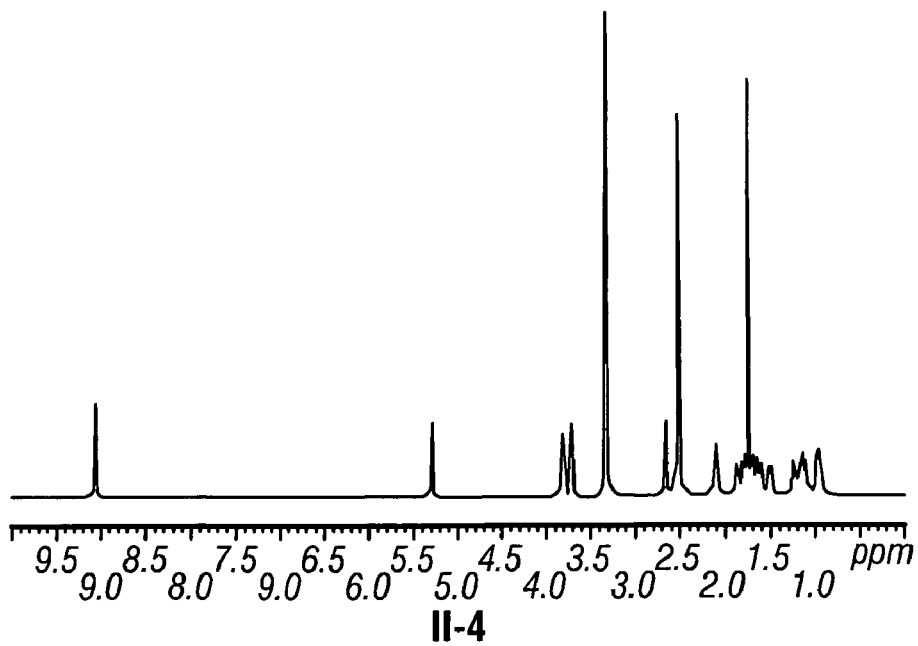
FIG. 14 depicts the 1H NMR spectrum of a compound having structure Formula II-4.
Figure 15:
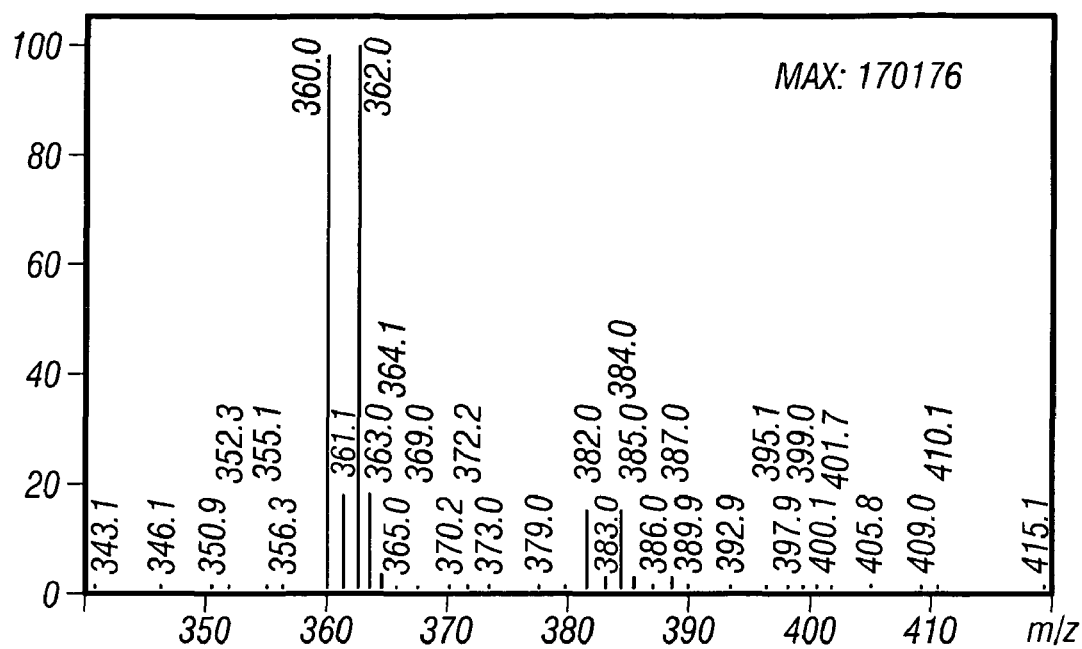
FIG. 15 depicts the mass spectrum of a compound having structure Formula II-4.

Compound of Formula II-4 eluted at 16.5 min as a pure compound: UV (acetonitrile/H$_2$O): $\lambda_{max}$ 225 (sh) nm. FIG. 14 depicts the NMR spectrum of the compound of Formula II-4 in DMSO-d$_6$. FIG. 15 depicts the low resolution mass of the compound of Formula II-4: m/z 360 (M+H), 382 (M+Na).

Example 7

Synthesis of the Compounds of Formulae II-5A and II-5B

Compounds of Formula II-5A and Formula II-5B can be synthesized from compound of Formula II-16 by epoxidation with mCPBA.

Compound of Formula II-16 (101 mg, 0.32 mmole) was dissolved in methylenechloride (30 mL) in a 100 ml of round bottom flask to which was added 79 mg (0.46 mmole) of meta-chloroperbenzoic acid (mCPBA) and a magnetic stir bar. The reaction mixture was stirred at room temperature for about 18 hours. The reaction mixture was poured onto a 20 cc silica flash column and eluted with 120 ml of CH$_2$Cl$_2$, 75 ml of 1:1 ethyl acetate/hexane and finally with 40 ml of 100% ethyl acetate. The 1:1 ethyl acatete/hexane fractions yield a mixture of diastereomers of epoxyderivatives, Formula II-5A and II-5B, which were separated by normal phase HPLC using the following conditions:

| Column | Phenomenex Luna 10 u Silica |
|---|---|
| Dimensions | 25 cm × 21.2 mm ID |
| Flow rate | 14.5 ml/min |
| Detection | ELSD |
| Solvent | 25% to 80% EtOAc/Hex over 19 min, 80 to 100% EtOAc in 1 min, then 5 min at 100% EtOAc |

Compound Formula II-5A (major product) and II-5B (minor product) eluted at 21.5 and 19 min, respectively, as pure compounds. Compound II-5B was further chromatographed on a 3 cc silica flash column to remove traces of chlorobenzoic acid reagent.

Chemical Structures:

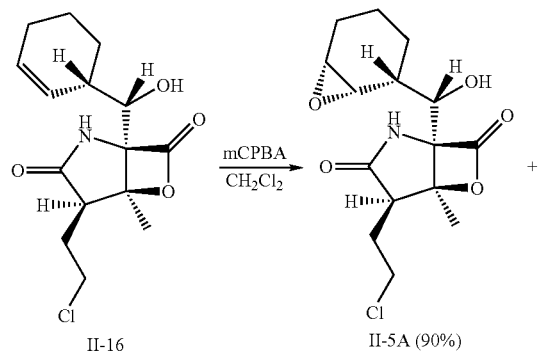

II-16     II-5A (90%)

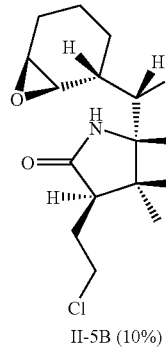

II-5B (10%)

Structural Characterization

Figure 16:
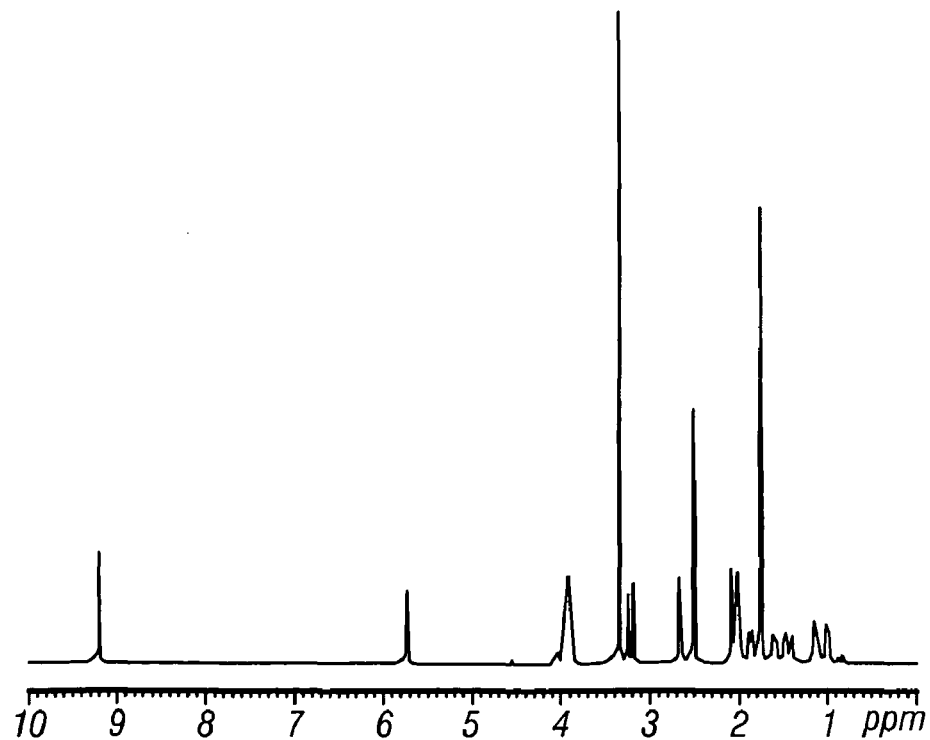
FIG. 16 depicts the 1H NMR spectrum of a compound having structure Formula II-5A.
Figure 17:
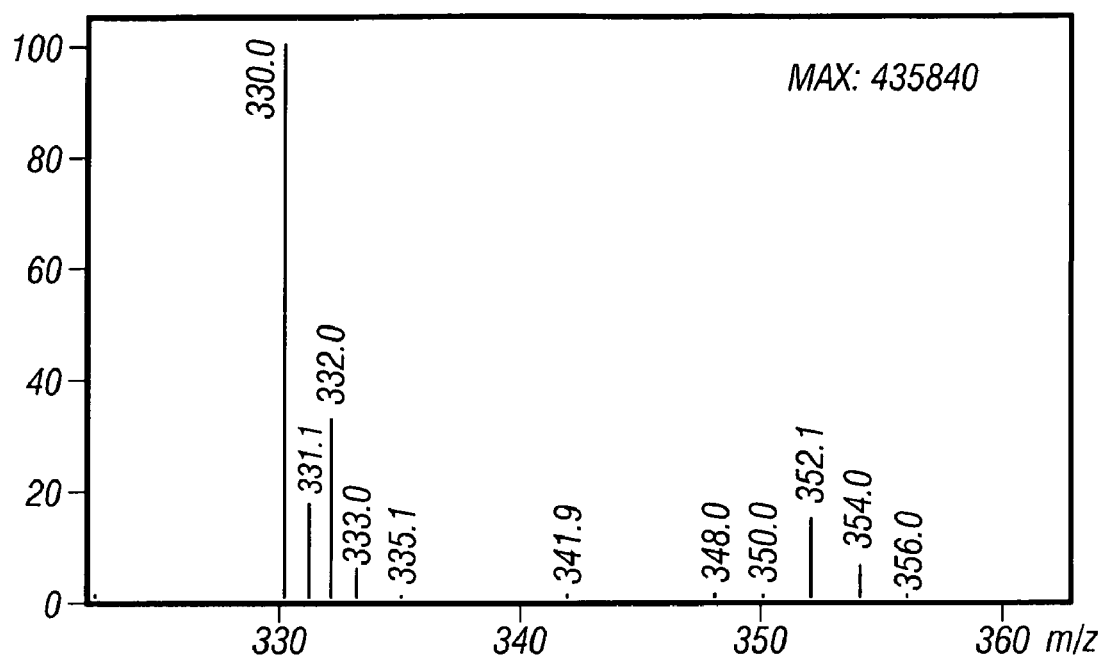
FIG. 17 depicts the mass spectrum of a compound having structure Formula II-5A.

Formula II-5A: UV (Acetonitrile/H$_2$O) $\lambda_{max}$ 225 (sh) nm. Low Res. Mass: m/z 330 (M+H), 352 (M+Na). FIGS. 16-17, respectively depict the 1H NMR spectrum of Formula II-5A and the mass spectrum of Formula II-5A.

Figure 18:
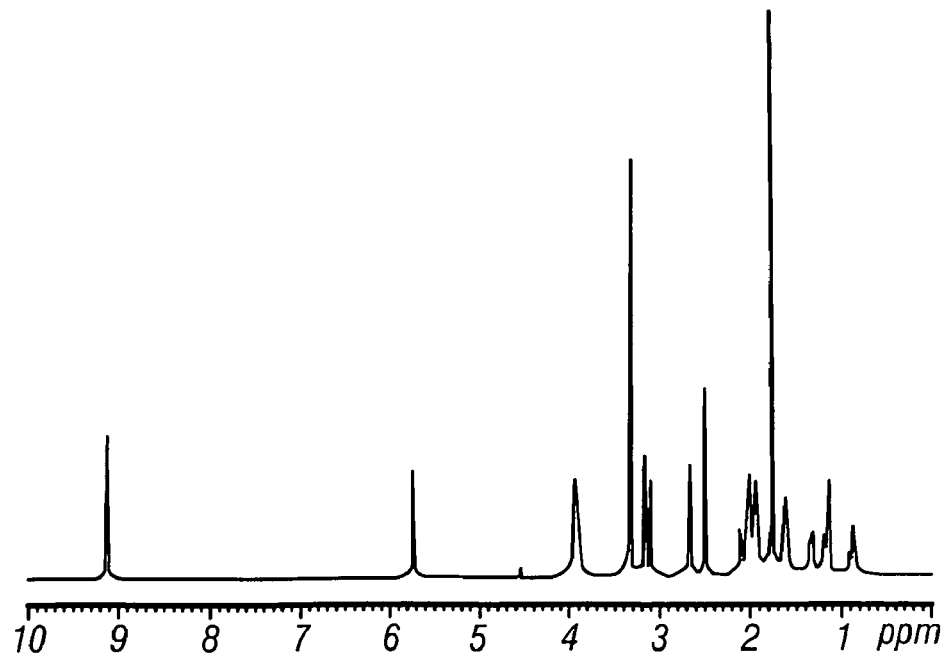
FIG. 18 depicts the 1H NMR spectrum of a compound having structure Formula II-5B.
Figure 19:
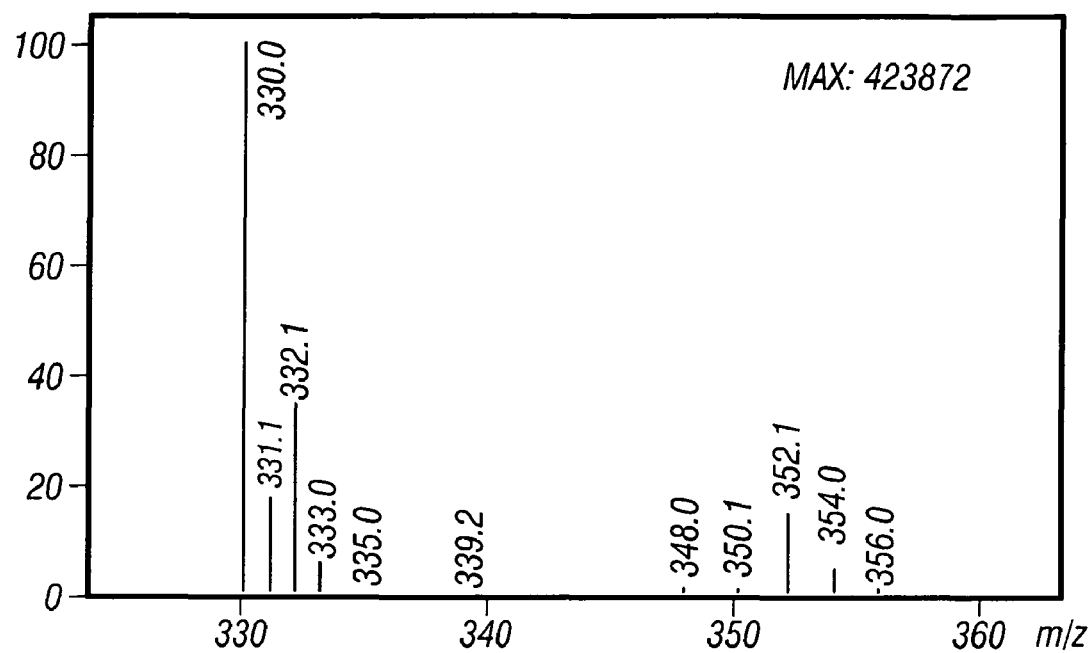
FIG. 19 depicts the mass spectrum of a compound having structure Formula II-5B.

Formula II-5B: UV (Acetonitrile/H$_2$O) $\lambda_{max}$ 225 (sh) nm. Low Res. Mass: m/z 330 (M+H), 352 (M+Na). FIGS. 18-19, respectively depict the 1H NMR spectrum of II-5B and the mass spectrum of II-5B.

Example 8

Synthesis of the Compounds of Formulae IV-1, IV-2, IV-3 and IV-4

Synthesis of Diol Derivatives (Formula IV-2)

Diols may be synthesized by Sharpless dihydroxylation using AD mix-α and β: AD mix-α is a premix of four reagents, K$_2$OsO$_2$(OH)$_4$; K$_2$CO$_3$; K$_3$Fe(CN)$_6$; (DHQ)$_2$-PHAL [1,4-bis(9-O-dihydroquinine)phthalazine] and AD mix-13 is a premix of K$_2$OsO$_2$(OH)$_4$; K$_2$CO$_3$; K$_3$Fe(CN)$_6$; (DHQD)$_2$-PHAL [1,4-bis(9-O-dihydroquinidine)phthalazine] which are commercially available from Aldrich. Diol can also be synthesized by acid or base hydrolysis of epoxy compounds (Formula II-5A and II-5B) which may be different to that of products obtained in Sharpless dihydroxylation in their stereochemistry at carbons bearing hydroxyl groups Sharpless Dihydroxylation of Compounds II-16, II-17 and II-18

Any of the compounds of Formulae II-16, II-17 and II-18 may be used as the starting compound. In the example below, compound of Formula II-16 is used. The starting compound is dissolved in t-butanol/water in a round bottom flask to which is added AD mix-α or β and a magnetic stir bar. The reaction is monitored by silica TLC as well as mass spectrometer. The pure diols are obtained by usual workup and purification by flash chromatography or HPLC. The structures are confirmed by NMR spectroscopy and mass spectrometry. In this method both hydroxyl groups are on same side.

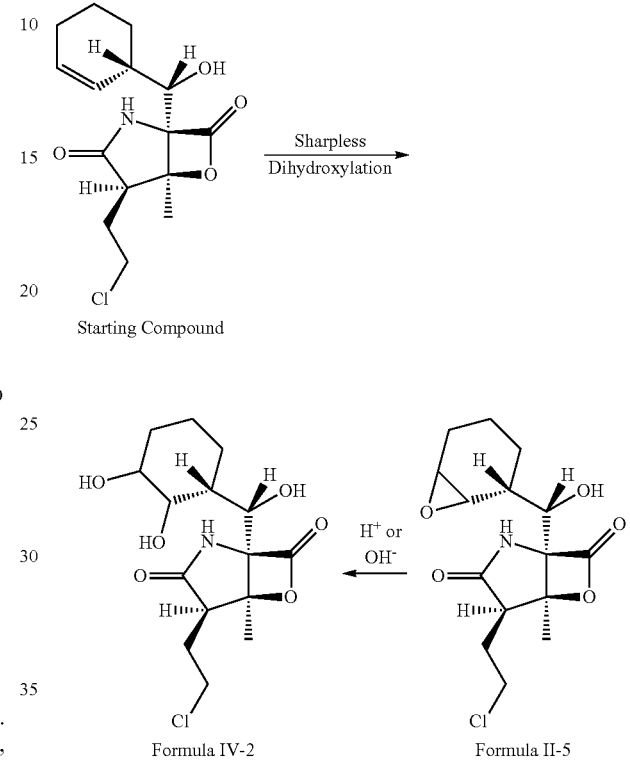

Nucleophilic Ring Opening of Epoxy Compounds (II-5):

The epoxy ring is opened with various nucleophiles like NaCN, NaN$_3$, NaOAc, HBr, HCl, etc. to create various substituents on the cyclohexane ring, including a hydroxyl substituent.

EXAMPLES

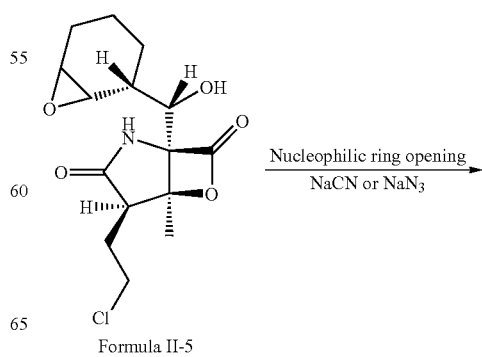

Formula II-5

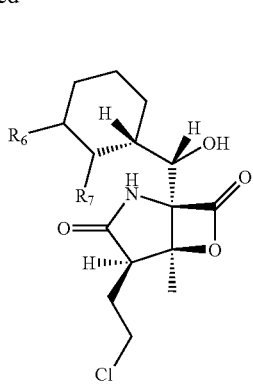

R7: CN or N3 if R6 is OH
R6: CN or N3 if R7 is OH
Formula IV-1

The epoxy is opened with HCl to make Formula IV-3:

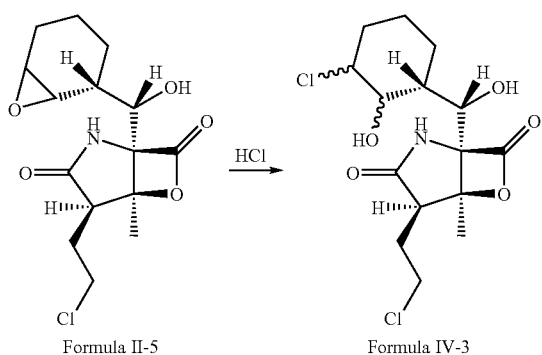

Formula II-5  Formula IV-3

Figure 20:
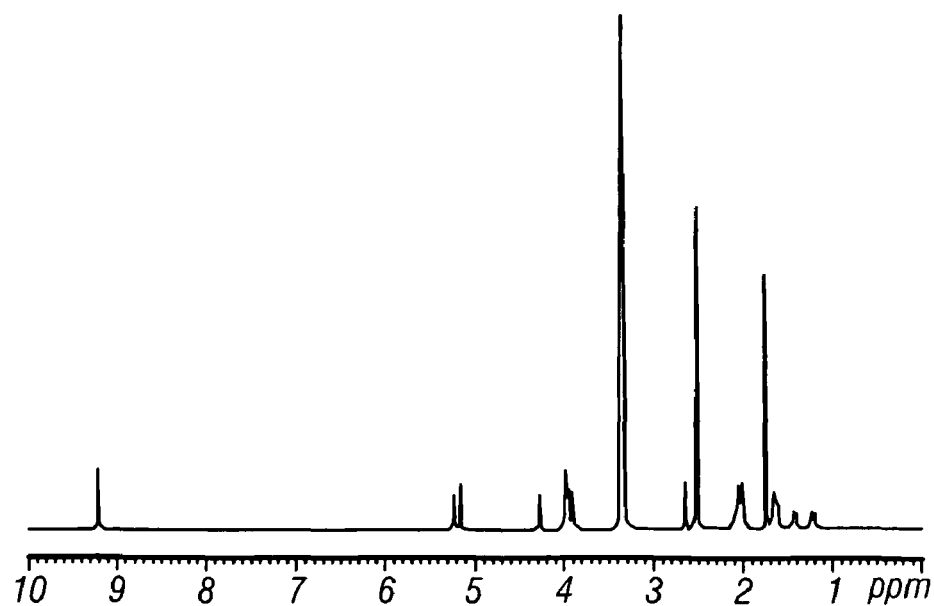
FIG. 20 depicts the 1H NMR spectrum of a compound having structure Formula IV-3C in DMSO-$d_6$.
Figure 21:
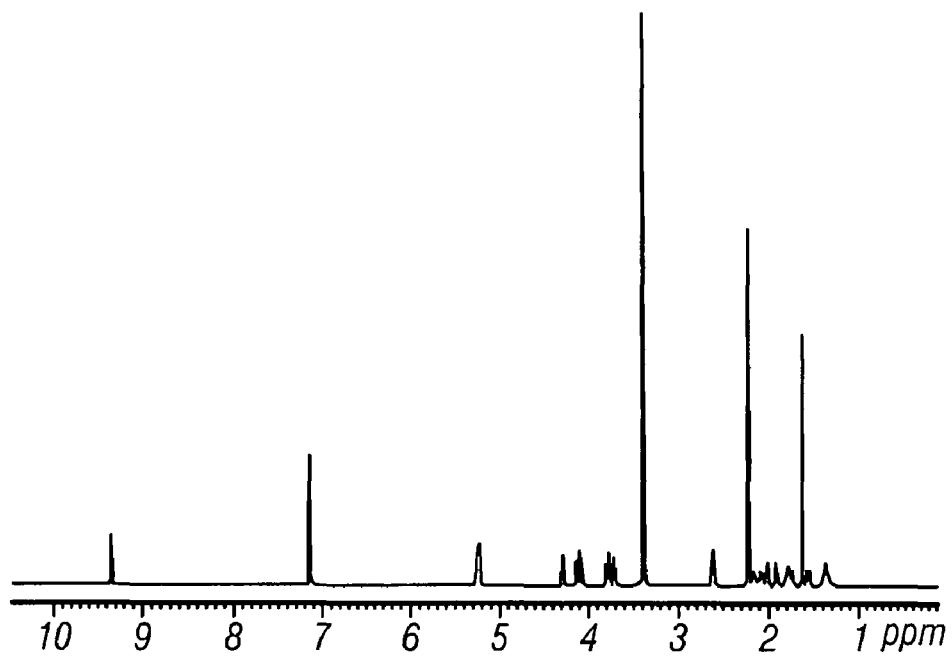
FIG. 21 depicts the 1H NMR spectrum of a compound having structure Formula IV-3C in $C_6D_6$/DMSO-$d_6$.

Compound of Formula II-5A (3.3 mg) was dissolved in acetonitrile (0.5 ml) in a 1 dram vial to which was added 5% HCl (500 ul) and a magnetic stir bar. The reaction mixture was stirred at room temperature for about an hour. The reaction was monitored by mass spectrometry. The reaction mixture was directly injected on normal phase HPLC to obtain compound of Formula IV-3C as a pure compound without any work up. The HPLC conditions used for the purification were as follows: Phenomenex Luna 10u Silica column (25 cm×21.2 mm ID) with a solvent gradient of 25% to 80% EtOAc/Hex over 19 min, 80 to 100% EtOAc in 1 min, then 5 min at 100% EtOAc at a flow rate of 14.5 ml/min. An ELSD was used to monitor the purification process. Compound of Formula IV-3C eluted at about 18 min (2.2 mg). Compound of Formula IV-3C: UV (Acetonitrile/$H_2O$) $\lambda_{max}$ 225 (sh) nm; ESMS, m/z 366 (M+H), 388 (M+Na); $^1$H NMR in DMSO-$d_6$ (FIG. 20) The stereochemistry of the compound of Formula IV-3C was determined based on coupling constants observed in the cyclohexane ring in 1:1 $C_6D_6$/DMSO-$d_6$ (FIG. 21)

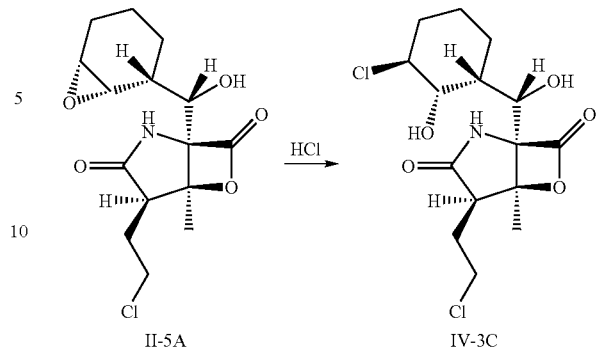

II-5A  IV-3C

Reductive ring opening of epoxides (II-5): The compound of Formula is treated with metalhydrides like $BH_3$-THF complex to make compound of Formula IV-4.

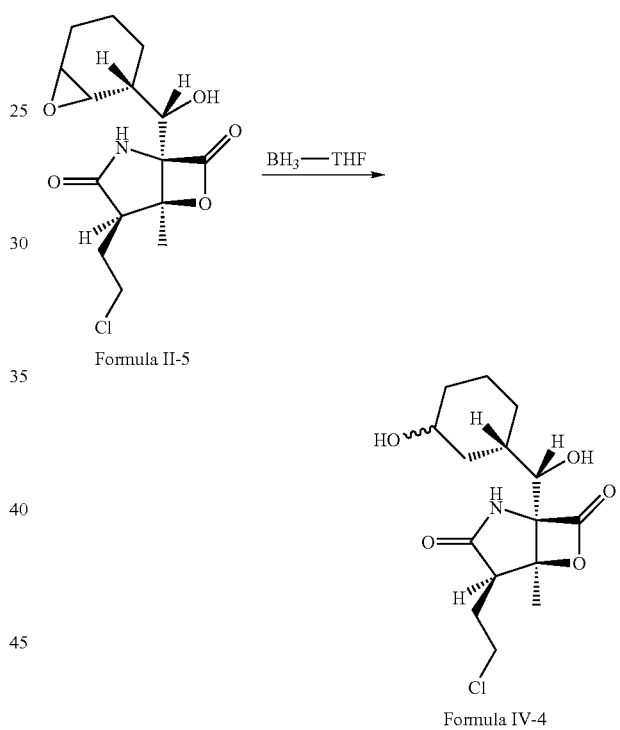

Formula II-5

Formula IV-4

Example 9

Synthesis of the Compounds of Formulae II-13C and II-8C

Figure 22:
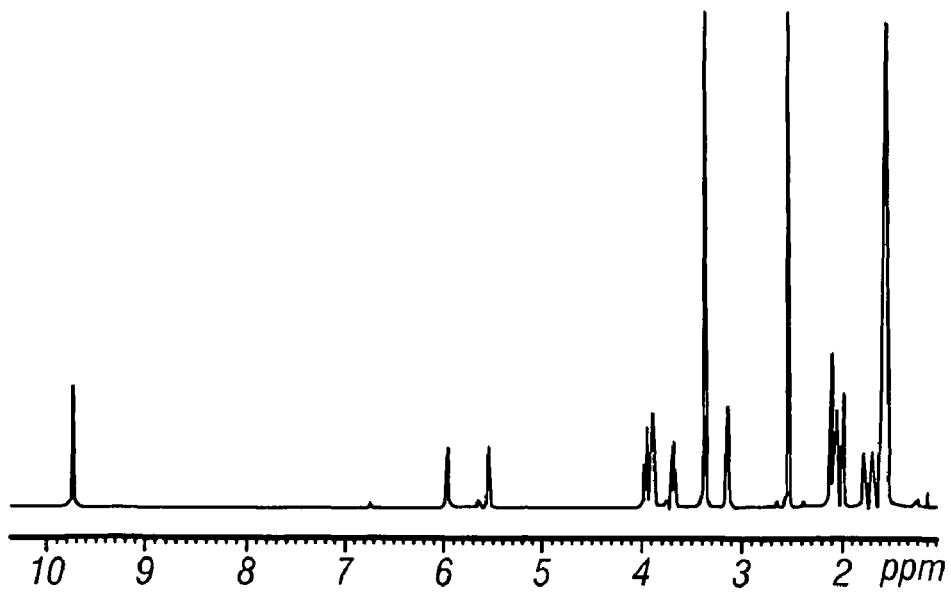
FIG. 22 depicts the 1H NMR spectrum of a compound having structure Formula II-13C.

Compound of Formula II-16 (30 mg) was dissolved in $CH_2Cl_2$ (6 ml) in a scintillation vial (20 ml) to which Dess-Martin Periodinane (122 mg) and a magnetic stir bar were added. The reaction mixture was stirred at room temperature for about 2 hours. The progress of the reaction was monitored by TLC (Hex:EtOAc, 6:4) and analytical HPLC. From the reaction mixture, the solvent volume was reduced to one third, absorbed on silica gel, poured on top of a 20 cc silica flash column and eluted in 20 ml fractions using a gradient of Hexane/EtOAc from 10 to 100%. The fraction eluted with 30% EtOAc in Hexane contained a mixture of rotamers of Formula II-13C in a ratio of 1.5:8.5. The mixture was further purified by normal phase HPLC using the Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-13C eluted at 13.0 and 13.2 mins as a mixture of rotamers with in a ratio of 1.5:8.5 (7 mg). Formula II-13C: UV (Acetonitrile/H$_2$O) $\lambda_{max}$ 226 (sh) & 300 (sh) nm; ESMS, m/z 312 (M+H)$^+$, 334 (M+Na)$^+$; $^1$H NMR in DMSO-d$_6$ (see FIG. 22).

Figure 23:
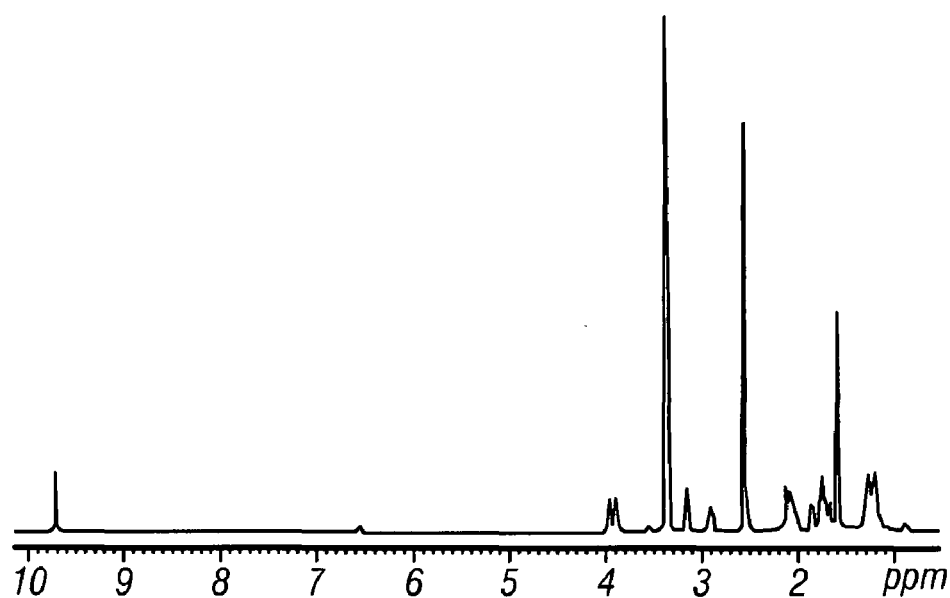
FIG. 23 depicts the 1H NMR spectrum of a compound having structure Formula II-8C.

The rotamer mixture of Formula II-13C (4 mg) was dissolved in acetone (1 ml) in a scintillation vial (20 ml) to which a catalytic amount (0.5 mg) of 10% (w/w) Pd/C and a magnetic stir bar were added. The reaction mixture was stirred in a hydrogen atmosphere at room temperature for about 15 hours. The reaction mixture was filtered through a 0.2 μm Gelman Acrodisc to remove the catalyst. The solvent was evaporated from the filtrate to yield compound of Formula II-8C as a colorless gum which was further purified by normal phase HPLC using a Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-8C (1 mg) eluted at 13.5 min as a pure compound. Formula II-8C: UV (Acetonitrile/H$_2$O) $\lambda_{max}$ 225 (sh) nm; ESMS, m/z 314 (M+H)$^+$, 336 (M+Na)$^+$; $^1$H NMR in DMSO-d$_6$ (See FIG. 23).

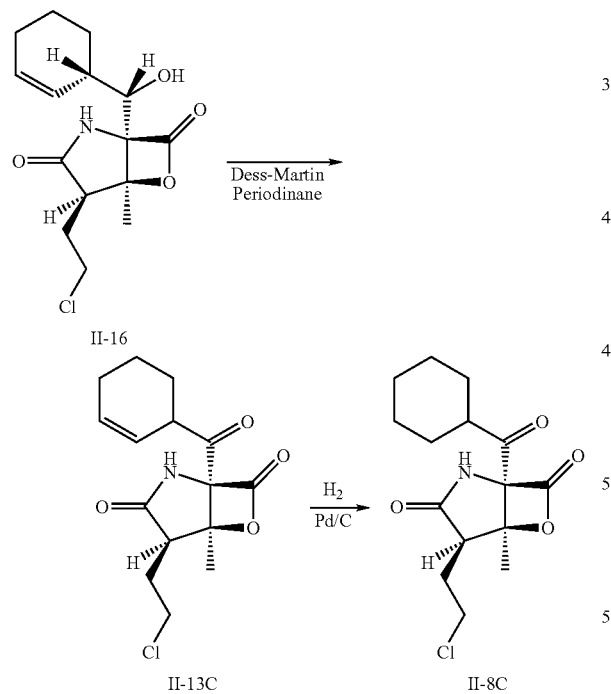

Example 10

Synthesis of the Compound of Formulae II-25 from II-13C

Figure 24:
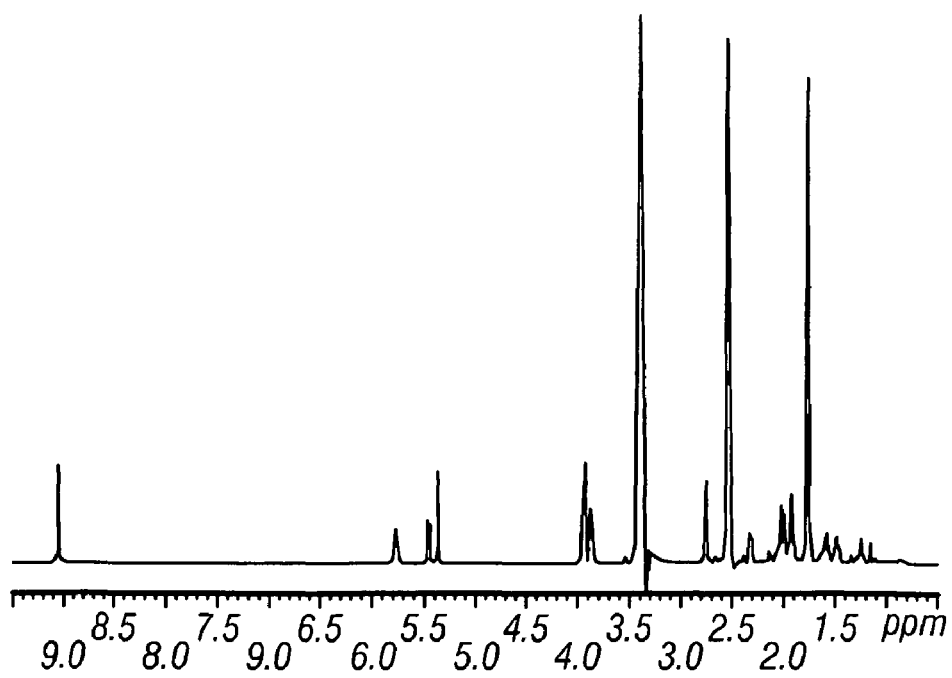
FIG. 24 depicts the 1H NMR spectrum of a compound having structure Formula II-25.

The rotamer mixture of Formula II-13C (5 mg) was dissolved in dimethoxy ethane (monoglyme; 1.5 ml) in a scintillation vial (20 ml) to which water (15 μl (1% of the final solution concentration)) and a magnetic stir bar were added. The above solution was cooled to −78° C. on a dry ice-acetone bath, and a sodium borohydride solution (3.7 mg of NaBH$_4$ in 0.5 ml of monoglyme (created to allow for slow addition)) was added drop-wise. The reaction mixture was stirred at −78° C. for about 14 minutes. The reaction mixture was acidified using 2 ml of 4% HCl solution in water and extracted with CH$_2$Cl$_2$. The organic layer was evaporated to yield mixture of compound of formulae II-25 and II-16 in a 9.5:0.5 ratio as a white solid, which was further purified by normal phase HPLC using a Phenomenex Luna 10u Silica column (25 cm×21.2 mm ID). The mobile phase was 24% EtOAc/76% Hexane, which was held isocratic for 19 min, followed by a linear gradient of 24% to 100% EtOAc over 1 min, and held at 100% EtOAc for 3 min; the flow rate was 25 ml/min. An ELSD was used to monitor the purification process. Compound of formula II-25 (1.5 mg) eluted at 11.64 min as a pure compound. Compound of Formula II-25: UV (Acetonitrile/H$_2$O) $\lambda_{max}$ 225 (sh) nm; ESMS, m/z 314 (M+H)$^+$, 336 (M+Na)$^+$; $^1$H NMR in DMSO-d$_6$ (see FIG. 24).

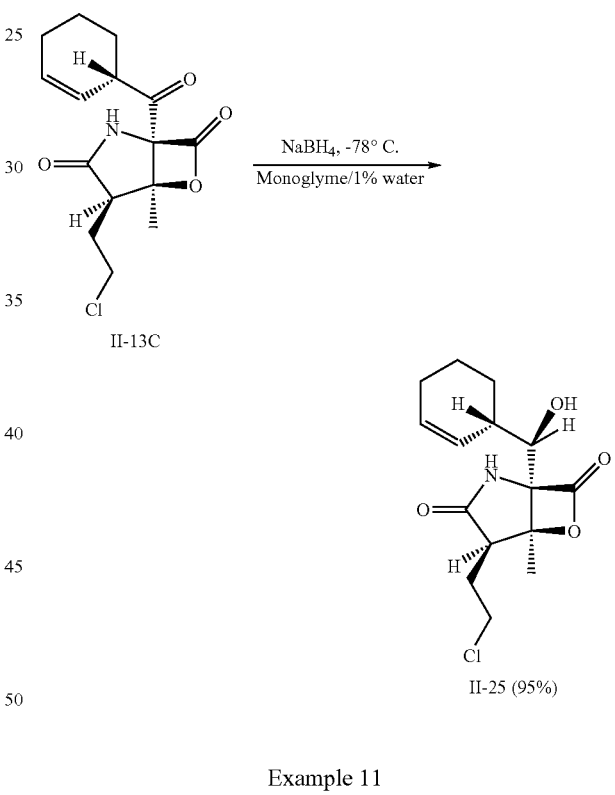

Example 11

Synthesis of the Compound of Formulae II-21 from II-19

Acetone (7.5 ml) was vigorously mixed with 5 N NaOH (3 ml) and the resulting mixture evaporated to a minimum volume in vacuo. A sample of 100 μl of this solution was mixed with compound of Formula II-19 (6.2 mg) in acetone (1 ml) and the resulting biphasic mixture vortexed for 2 minutes. The reaction solution was immediately subjected to preparative C18 HPLC. Conditions for the purification involved a linear gradient if 10% acetonitrile/90% water to 90% acetonitrile/10% water over 17 minutes using an Ace 5μ C18 HPLC column of dimensions 22 mm id by 150 mm length.

Figure 25:
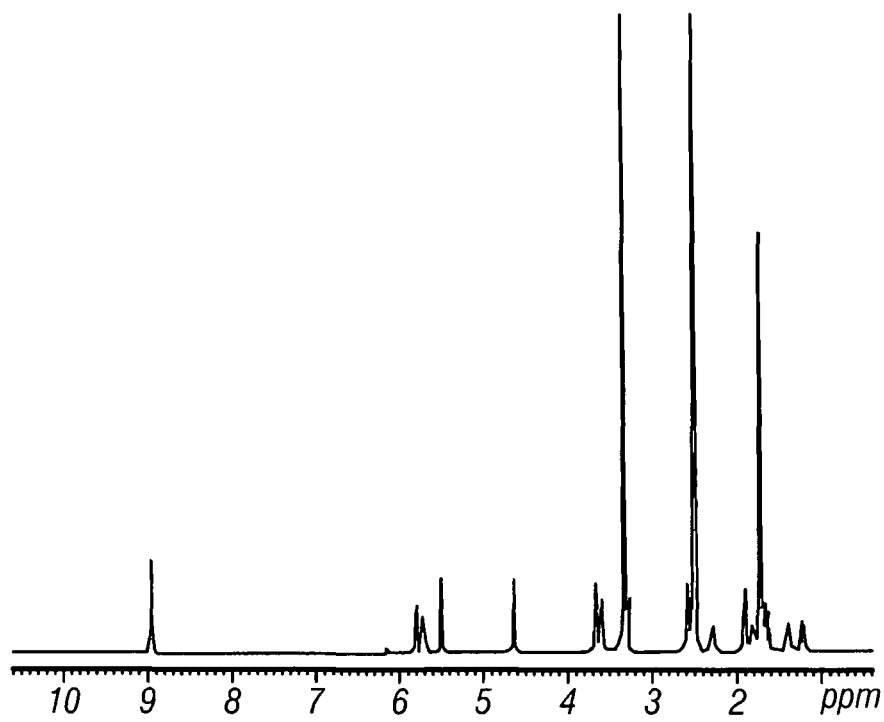
FIG. 25 depicts the 1H NMR spectrum of a compound having structure Formula II-21.

Compound of Formula II-21 eluted at 9.1 minutes under these conditions to yield 0.55 mg compound. Compound of Formula II-21: UV (Acetonitrile/H$_2$O) 225 (sh), ESMS, m/z 296.1 (M+H); $^1$H NMR in DMSO-d$_6$ (see FIG. 25).

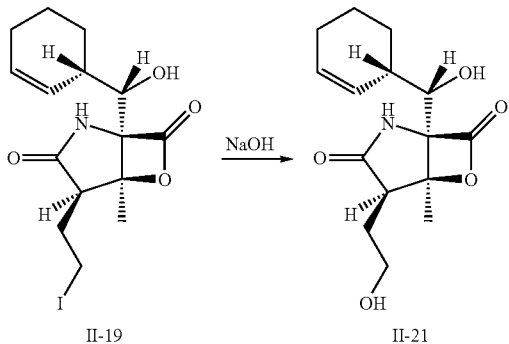

II-19  II-21

Example 12

Synthesis of the Compound of Formulae II-22 from II-19

Figure 26:
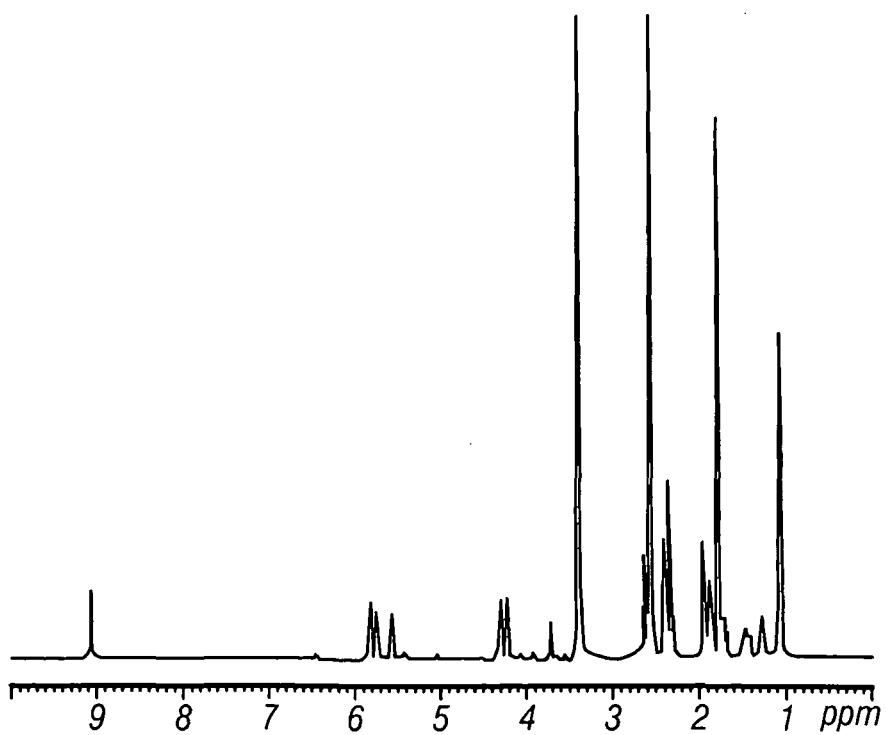
FIG. 26 depicts the 1H NMR spectrum of a compound having structure Formula II-22.

A sample of 60 mg sodium propionate was added to a solution of compound of Formula II-19 (5.3 mg) in DMSO (1 ml) and the mixture sonicated for 5 minutes, though the sodium propionate did not completely dissolve. After 45 minutes, the solution was filtered through a 0.45µ syringe filter and purified directly using HPLC. Conditions for the purification involved a linear gradient if 10% acetonitrile/90% water to 90% acetonitrile/10% water over 17 minutes using an Ace 5µ C18 HPLC column of dimensions 22 mm id by 150 mm length. Under these conditions, compound of Formula II-22 eluted at 12.3 minutes to yield 0.7 mg compound (15% isolated yield). UV (Acetonitrile/H$_2$O) 225 (sh), ESMS, m/z 352.2 (M+H); $^1$H NMR in DMSO-d$_6$ (see FIG. 26).

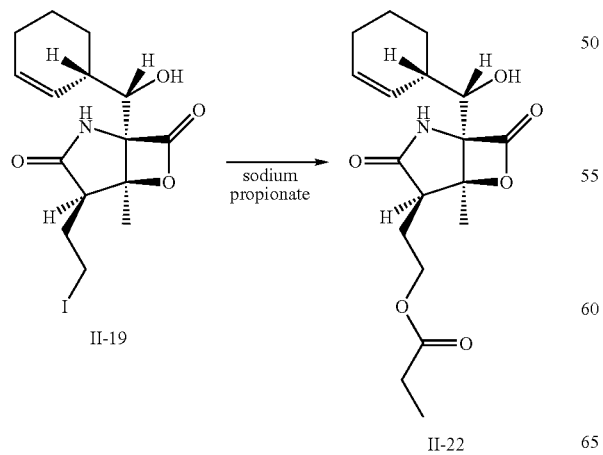

II-19  II-22

Example 13

Oxidation of Secondary Hydroxyl Group in Compounds of Formulae II-16, II-17 and II-18 and Reaction with Hydroxy or Methoxy Amines Any of the compounds of Formulae II-16, II-17 and II-18 may be used as the starting compound. The secondary hydroxyl group in the starting compound is oxidized using either of the following reagents: pyridinium dichromate (PDC), pyridinium chlorochromate (PCC), Dess-Martin periodinane or oxalyl chloride (Swern oxidation) (Ref: Organic Syntheses, collective volumes I-VIII). Preferably, Dess-Martin periodinane may be used as a reagent for this reaction. (Ref: Fenteany G. et al. *Science,* 1995, 268, 726-73). The resulting keto compound is treated with hydroxylamine or methoxy amine to generate oximes.

EXAMPLES

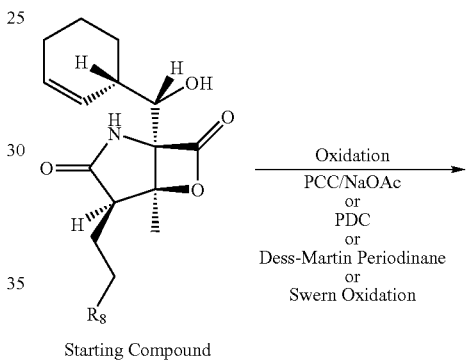

Starting Compound

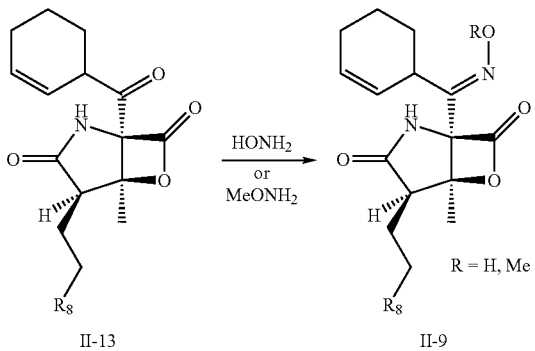

II-13  II-9

Example 14

Reductive Amination of Keto-Derivative

The keto derivatives, for example Formula II-8 and II-13, are treated with sodium cyanoborohydride (NaBH$_3$CN) in the presence of various bases to yield amine derivatives of the starting compounds which are subsequently hydrogenated with 10% Pd/C, $H_2$ to reduce the double bond in the cyclohexene ring.

Example

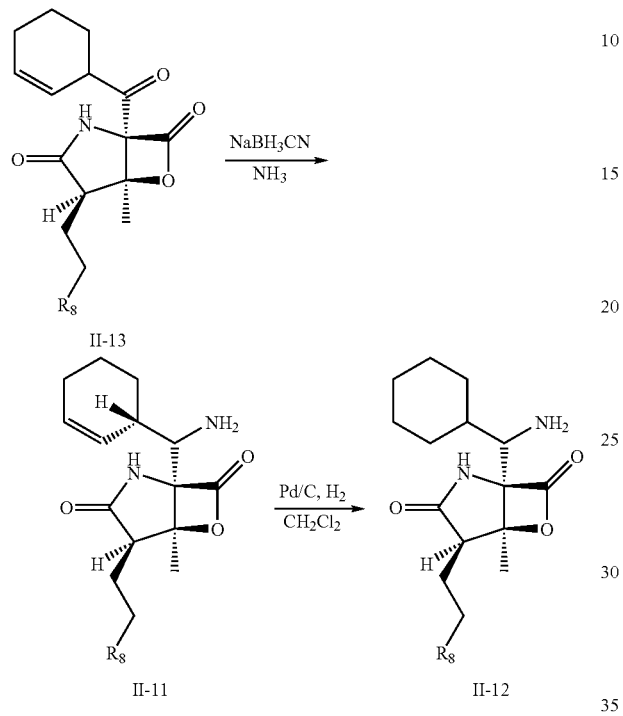

II-13

II-11                II-12

Example 15

Cyclohexene Ring Opening

Any compound of Formulae II-16, II-17 and II-18 may be used as a starting compound. The starting compound is treated with $OsO_4$ and $NaIO_4$ in THF—$H_2O$ solution to yield dial derivatives which are reduced to alcohol with $NaBH_4$ in the same pot.

Example

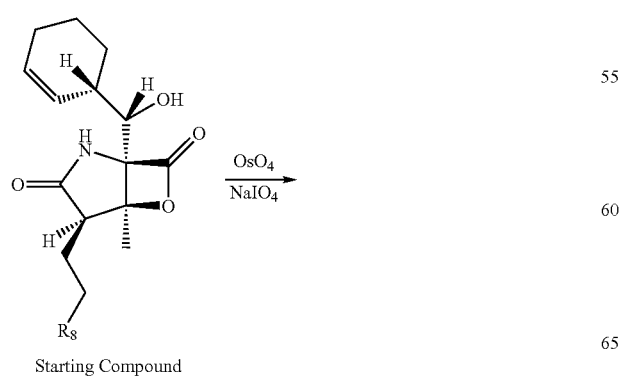

Starting Compound

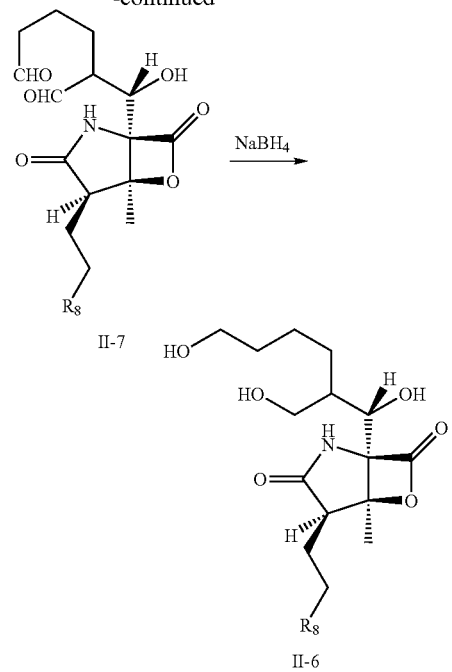

II-7

II-6

Example 16

Dehydration of Alcohol Followed by Aldehyde Formation at Lactone-Lactam Ring Junction A starting compound of any of Formulae II-16, II-17 or II-18 is treated with mesylchloride in the presence of base to yield a dehydrated derivative. The resulting dehydrated compound is treated with $OsO_4$ and $NaIO_4$ in THF—$H_2O$ to yield an aldehyde group at the lactone-lactam ring junctin.

Starting Compound

I-6                I-1

Example 17

Various Reactions on Aldehyde Derivatives I-1

Wittig reactions are performed on the aldehyde group using various phosphorus ylides [e.g., (triphenylphosphoranylidene)ethane] to yield an olefin. The double bond in the side chain is reduced by catalytic hydrogenation.

Example

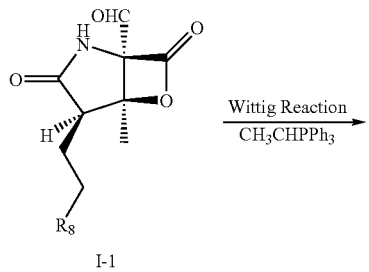

I-1

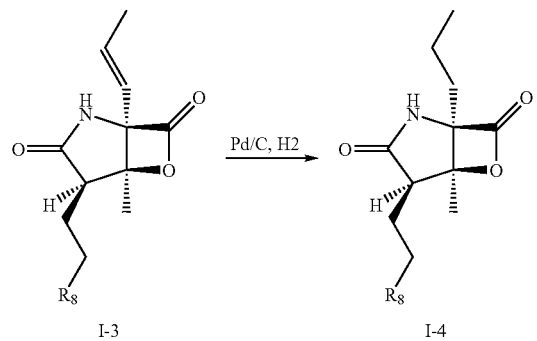

I-3    I-4

Reductive amination is performed on the aldehyde group using various bases (eg. $NH_3$) and sodium cyanoborohydride to yield amine derivatives. Alternatively, the aldehyde is reduced with $NaBH_4$ to form alcohols in the side chain.

Example

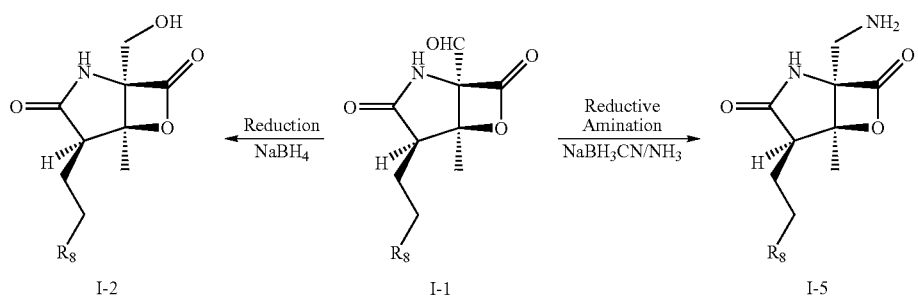

I-2    I-1    I-5

Organometallic addition reactions to the aldehyde carbonyl, such as Grignard reactions, may be performed using various alkyl magnesium bromide or chloride reagents (eg. isopropylmagnesium bromide, phenylmagnesium bromide) to yield various substituted secondary alcohols.

Example

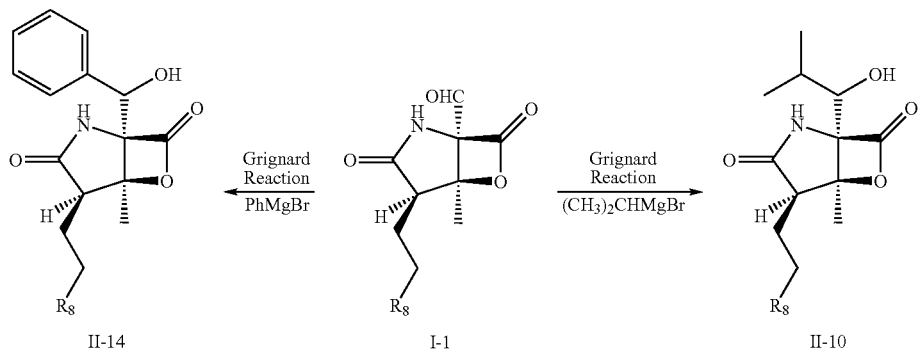

II-14    I-1    II-10

Example 18

In Vitro Biology

Initial studies of a compound of Formula II-16, which is also referred to as Salinosporamide A, employed the National Cancer Institute (NCI) screening panel, which consists of 60 human tumor cell lines that represent leukemia, melanoma and cancers of the lung, colon, brain, ovary, breast, prostate and kidney. A detailed description of the screening procedure can be found at hypertext transfer protocol (http://) "dtp.nci.nih.gov/branches/btb/ivclsp.html."

In brief, each of the 60 human tumor cell lines were grown in RPMI 1640 medium, supplemented with 5% fetal bovine serum and 2 mM L-glutamine. Cells were plated at their appropriate density in 96-well microtiter plates and incubated at 37° C., 5% $CO_2$, 95% air and 100% relative humidity. After 24 hours, 100 µL of various 10-fold serial dilutions of Salinosporamide A were added to the appropriate wells containing 100 µL of cells, resulting in a final Salinosporamide A concentration ranging from 10 nM to 100 µM. Cells were incubated for an additional 48 hours and a sulforhodamine B protein assay was used to estimate cell viability or growth.

Three dose response parameters were calculated as follows:

$GI_{50}$ indicates the concentration that inhibits growth by 50%.

TGI indicates the concentration that completely inhibits growth.

$LC_{50}$ indicates the concentration that is lethal to 50% of the cells.

An example of a study evaluating Salinosporamide A in the NCI screen is shown in Table 1 below.

Data indicate that the mean $GI_{50}$ value of Salinosporamide A was less than 10 nM. The wide range (>1000-fold difference) observed in both the mean TGI and mean $LC_{50}$ values for the most sensitive and the most resistant tumor cell lines illustrates that Salinosporamide A displays good selectivity and does not appear to be a general toxin. Furthermore, the mean TGI data suggest that Salinosporamide A shows preferred specificity towards melanoma and breast cancer cell lines. The assay was repeated and showed similar results.

The results of the NCI tumor screen show that Salinosporamide A: (1) is a potent compound with a mean $GI_{50}$ value of <10 nM, and (2) displays good tumor selectivity of more than 1000-fold difference in both the mean TGI and mean $LC_{50}$ values between the most sensitive and resistant tumor cell lines.

TABLE 1

Relative Sensitivity of the NCI 60 Human Tumor Cell Lines to Salinosporamide A
National Cancer Institute Developmental Therapeutics Program Mean Graphs NSC: D-721267/1     Units: Molar     SSPL: 0.75T     Exp. ID: 0108RS09-1
Report Date: Sep. 17, 2001                           Test Date: Aug. 6, 2001

| Panel/Cell Line | $Log_{10}$ GI50 | GI50 |
|---|---|---|
| Leukemia | | |
| CCRF-CEM | <−8.00 | |
| HL-60 (TB) | <−8.00 | |
| K-562 | <−8.00 | |
| MOLT-4 | <−8.00 | |
| RPMI-8226 | <−8.00 | |
| SR | <−8.00 | |
| Non-Small Cell Lung Cancer | | |
| A549/ATCC | <−8.00 | |
| EKVX | <−8.00 | |
| HOP-62 | <−8.00 | |
| HOP-92 | <−8.00 | |
| NCI-H226 | <−8.00 | |
| NCI-H23 | <−8.00 | |
| NCI-H322M | <−8.00 | |
| NCI-H460 | <−8.00 | |
| NCI-H522 | <−8.00 | |
| Colon Cancer | | |
| COLO 205 | <−8.00 | |
| HCC-2998 | <−8.00 | |
| HCT-116 | <−8.00 | |
| HCT-15 | <−8.00 | |
| HT29 | <−8.00 | |
| KM12 | <−8.00 | |
| SW-620 | <−8.00 | |
| CNS Cancer | | |
| SF-268 | <−8.00 | |
| SF-295 | <−8.00 | |
| SF-539 | <−8.00 | |
| SNB-19 | <−8.00 | |
| SNB-75 | <−8.00 | |
| U251 | <−8.00 | |
| Melanoma | | |
| LOX IMVI | <−8.00 | |
| MALME-3M | <−8.00 | |
| M14 | <−8.00 | |
| SK-MEL-2 | <−8.00 | |
| SK-MEL-28 | <−8.00 | |
| UACC-257 | <−8.00 | |
| UACC-62 | <−8.00 | |

TABLE 1-continued

| | | |
|---|---|---|
| Ovarian Cancer | | |
| IGROV1 | <−8.00 | |
| OVCAR-3 | <−8.00 | |
| OVCAR-4 | <−8.00 | |
| OVCAR-5 | <−8.00 | |
| OVCAR-8 | <−8.00 | |
| SK-OV-3 | <−8.00 | |
| Renal Cancer | | |
| 786-0 | <−8.00 | |
| A498 | <−8.00 | |
| ACHN | <−8.00 | |
| CAKI-1 | <−8.00 | |
| RXF 393 | <−8.00 | |
| SN 12C | <−8.00 | |
| TK-10 | <−8.00 | |
| UO-31 | <−8.00 | |
| Prostate Cancer | | |
| PC-3 | <−8.00 | |
| DU-145 | <−8.00 | |
| Breast Cancer | | |
| MCF7 | <−8.00 | |
| NCI/ADR-RES | <−8.00 | |
| MDA-MB-231/ATCC | <−8.00 | |
| MDA-MB-435 | <−8.00 | |
| MDA-N | <−8.00 | |
| BT-549 | <−8.00 | |
| T-47D | <−8.00 | |
| MG_MID | −8.00 | |
| Delta | 0.00 | |
| Range | 0.00 | |

| Panel/Cell Line | $Log_{10}$ GI50 | TGI |
|---|---|---|
| Leukemia | | |
| CCRF-CEM | <−8.00 | |
| HL-60 (TB) | −4.32 | |
| K-562 | −5.39 | |
| MOLT-4 | <−8.00 | |
| RPMI-8226 | <−8.00 | |
| SR | <−8.00 | |
| Non-Small Cell Lung Cancer | | |
| A549/ATCC | −4.70 | |
| EKVX | −5.67 | |
| HOP-62 | −4.89 | |
| HOP-92 | −7.77 | |
| NCI-H226 | <−8.00 | |
| NCI-H23 | −7.85 | |
| NCI-H322M | −5.48 | |
| NCI-H460 | −6.97 | |
| NCI-H522 | <−8.00 | |
| Colon Cancer | | |
| COLO 205 | −6.19 | |
| HCC-2998 | <−8.00 | |
| HCT-116 | −7.84 | |
| HCT-15 | −6.06 | |
| HT29 | −7.37 | |
| KM12 | −6.00 | |
| SW-620 | >−4.00 | |
| CNS Cancer | | |
| SF-268 | −6.92 | |
| SF-295 | <−8.00 | |
| SF-539 | <−8.00 | |
| SNB-19 | >−4.00 | |
| SNB-75 | <−8.00 | |
| U251 | −5.99 | |
| Melanoma | | |
| LOX IMVI | −7.87 | |
| MALME-3M | <−8.00 | |
| M14 | −7.94 | |
| SK-MEL-2 | <−8.00 | |
| SK-MEL-28 | <−8.00 | |
| UACC-257 | <−8.00 | |
| UACC-62 | <−8.00 | |

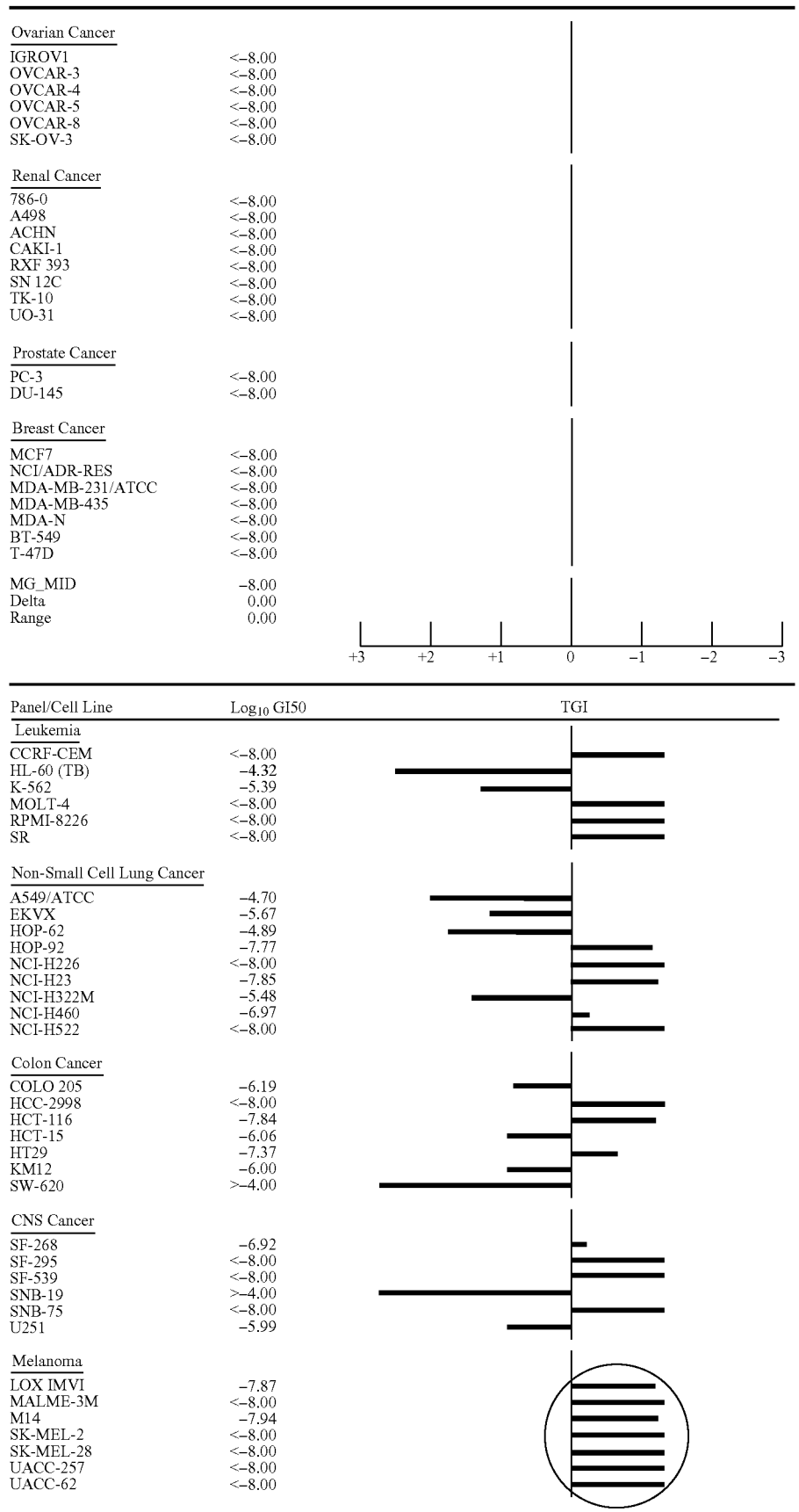

TABLE 1-continued

| Panel/Cell Line | $Log_{10}$ GI50 | LC50 |
|---|---|---|
| Ovarian Cancer | | |
| IGROV1 | −5.18 | |
| OVCAR-3 | −4.88 | |
| OVCAR-4 | <−8.00 | |
| OVCAR-5 | −7.26 | |
| OVCAR-8 | −7.70 | |
| SK-OV-3 | <−8.00 | |
| Renal Cancer | | |
| 786-0 | −5.37 | |
| A498 | <−8.00 | |
| ACHN | −5.27 | |
| CAKI-1 | >−4.00 | |
| RXF 393 | <−8.00 | |
| SN 12C | <−8.00 | |
| TK-10 | −7.13 | |
| UO-31 | −5.88 | |
| Prostate Cancer | | |
| PC-3 | −5.81 | |
| DU-145 | >−4.00 | |
| Breast Cancer | | |
| MCF7 | >−4.00 | |
| NCI/ADR-RES | <−8.00 | |
| MDA-MB-231/ATCC | <−8.00 | |
| MDA-MB-435 | <−8.00 | |
| MDA-N | <−8.00 | |
| BT-549 | <−8.00 | |
| T-47D | >−4.00 | |
| MG_MID | −6.79 | |
| Delta | 1.21 | |
| Range | 4.00 | |

| Panel/Cell Line | $Log_{10}$ GI50 | LC50 |
|---|---|---|
| Leukemia | | |
| CCRF-CEM | >−4.00 | |
| HL-60 (TB) | >−4.00 | |
| K-562 | >−4.00 | |
| MOLT-4 | >−4.00 | |
| RPMI-8226 | >−4.00 | |
| SR | −4.19 | |
| Non-Small Cell Lung Cancer | | |
| A549/ATCC | >−4.00 | |
| EKVX | >−4.00 | |
| HOP-62 | >−4.00 | |
| HOP-92 | −5.36 | |
| NCI-H226 | <−8.00 | |
| NCI-H23 | −6.31 | |
| NCI-H322M | −4.37 | |
| NCI-H460 | >−4.00 | |
| NCI-H522 | −7.37 | |
| Colon Cancer | | |
| COLO 205 | −4.06 | |
| HCC-2998 | −7.75 | |
| HCT-116 | −4.99 | |
| HCT-15 | −4.25 | |
| HT29 | −4.42 | |
| KM12 | −4.23 | |
| SW-620 | >−4.00 | |
| CNS Cancer | | |
| SF-268 | >−4.00 | |
| SF-295 | −6.63 | |
| SF-539 | <−8.00 | |
| SNB-19 | >−4.00 | |
| SNB-75 | −7.50 | |
| U251 | >−4.00 | |
| Melanoma | | |
| LOX IMVI | >−4.00 | |
| MALME-3M | −4.89 | |
| M14 | −6.73 | |
| SK-MEL-2 | −6.79 | |
| SK-MEL-28 | <−8.00 | |
| UACC-257 | −4.37 | |
| UACC-62 | >−4.00 | |

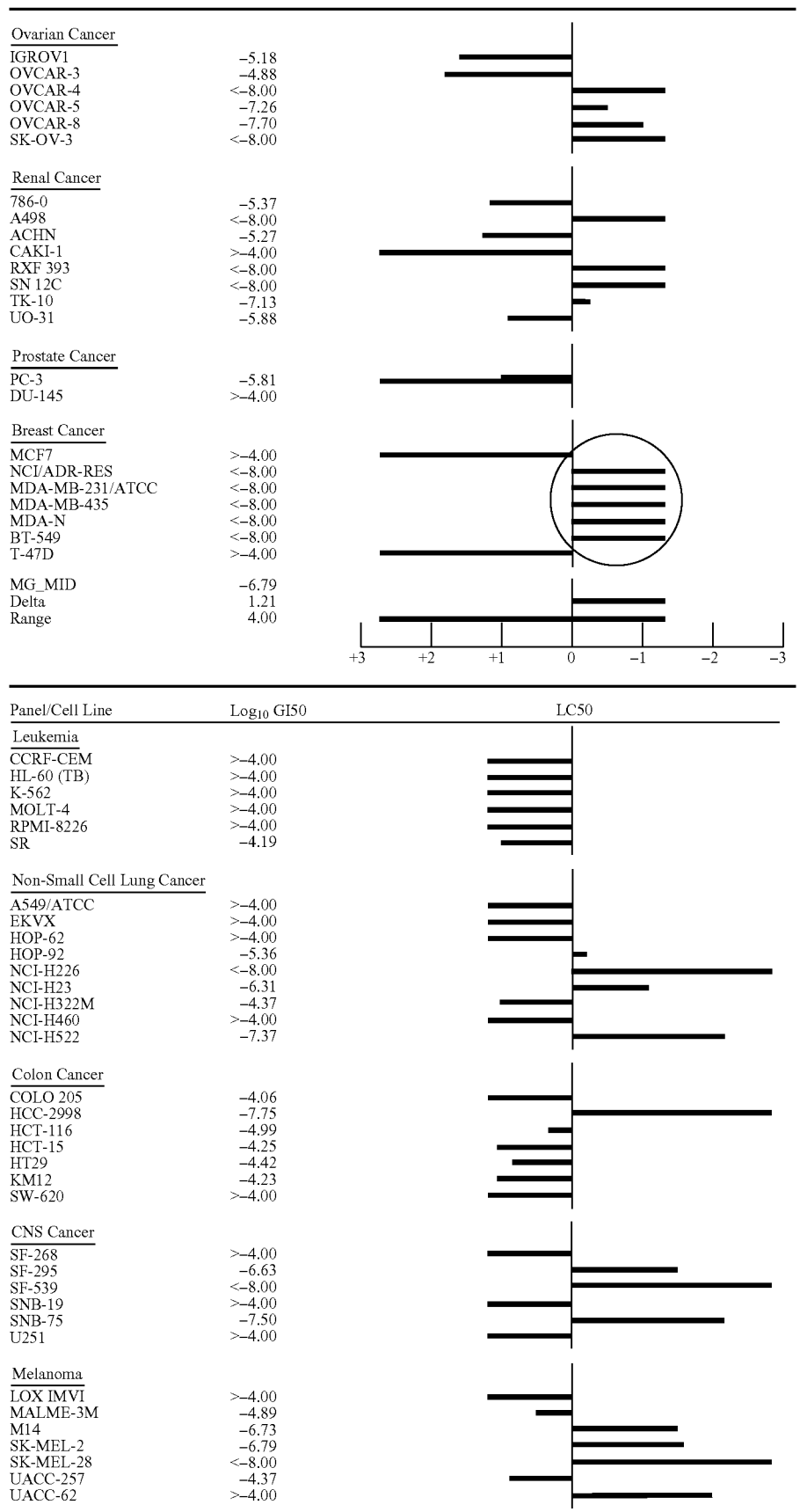

TABLE 1-continued

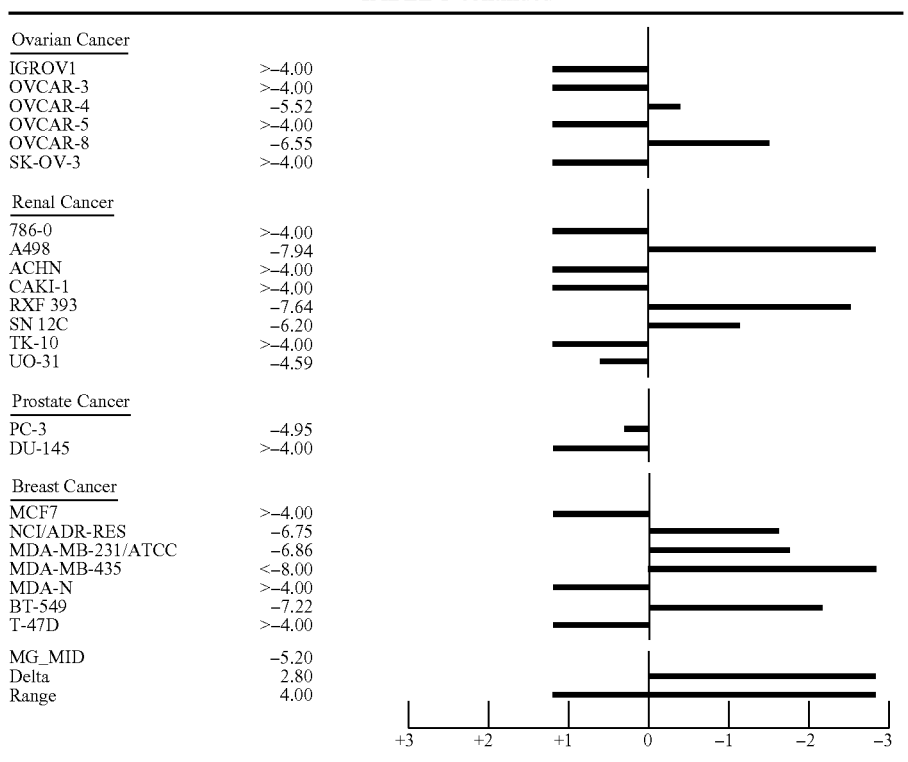

| | |
|---|---|
| Ovarian Cancer | |
| IGROV1 | >−4.00 |
| OVCAR-3 | >−4.00 |
| OVCAR-4 | −5.52 |
| OVCAR-5 | >−4.00 |
| OVCAR-8 | −6.55 |
| SK-OV-3 | >−4.00 |
| Renal Cancer | |
| 786-0 | >−4.00 |
| A498 | −7.94 |
| ACHN | >−4.00 |
| CAKI-1 | >−4.00 |
| RXF 393 | −7.64 |
| SN 12C | −6.20 |
| TK-10 | >−4.00 |
| UO-31 | −4.59 |
| Prostate Cancer | |
| PC-3 | −4.95 |
| DU-145 | >−4.00 |
| Breast Cancer | |
| MCF7 | >−4.00 |
| NCI/ADR-RES | −6.75 |
| MDA-MB-231/ATCC | −6.86 |
| MDA-MB-435 | <−8.00 |
| MDA-N | >−4.00 |
| BT-549 | −7.22 |
| T-47D | >−4.00 |
| MG_MID | −5.20 |
| Delta | 2.80 |
| Range | 4.00 |

Example 19

Growth Inhibition of Tumor Cell Lines

B16-F10 (ATCC; CRL-6475), DU 145 (ATCC; HTB-81), HEK293 (ATCC; CRL-1573), HT-29 (ATCC; HTB-38), LoVo (ATCC; CCL-229), MDA-MB-231 (ATCC; HTB-26), MIA PaCa-2 (ATCC; CRL-1420), NCI-H292 (ATCC; CRL-1848), OVCAR-3 (ATCC, HTB-161), PANC-1 (ATCC; CRL-1469), PC-3 (ATCC; CRL-1435), RPMI 8226 (ATCC; CCL-155) and U266 (ATCC; TIB-196) were maintained in appropriate culture media. The cells were cultured in an incubator at 37° C. in 5% CO2 and 95% humidified air.

For cell growth inhibition assays, B16-F10, DU 145, HEK293, HT-29, LoVo, MDA-MB-231, MIA PaCa-2, NCI-H292, OVCAR-3, PANC-1, PC-3, RPMI 8226 and U266 cells were seeded at $1.25 \times 10^3$, $5 \times 10^3$, $1.5 \times 10^4$, $5 \times 10^3$, $5 \times 10^3$, $1 \times 10^4$, $2 \times 10^3$, $4 \times 10^3$, $1 \times 10^4$, $7.5 \times 10^3$, $5 \times 10^3$, $2 \times 10^4$, $2.5 \times 10^4$ cells/well respectively in 90 μl complete media into Corning 3904 black-walled, clear-bottom tissue culture plates. 20 mM stock solutions of Formula II-16 were prepared in 100% DMSO, aliquoted and stored at −80° C. Formula II-16 was serially diluted and added in triplicate to the test wells resulting in final concentrations ranging from of 20 μM to 0.2 pM. The plates were returned to the incubator for 48 hours. The final concentration of DMSO was 0.25% in all samples.

Following 48 hours of drug exposure, 10 μl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0, ID Business Solutions Ltd or Prism 3.0, GraphPad Software Inc).

The data in Table 2 summarize the growth inhibitory effects of Formula II-16 against 13 diverse human and mouse tumor cell lines.

TABLE 2

Mean $EC_{50}$ values of Formula II-16 against various tumor cell lines

| Cell line | Source | $EC_{50}$ (nM), mean ± SD * | n |
|---|---|---|---|
| B16-F10 | Mouse, melanoma | 47 ± 20 | 12 |
| DU 145 | Human, prostate carcinoma | 37 ± 10 | 3 |
| HEK293 | Human, embryonic kidney | 47 | 2 |
| HT-29 | Human, colorectal adenocarcinoma | 40 ± 26 | 5 |
| LoVo | Human, colorectal adenocarcinoma | 70 ± 8 | 3 |
| MDA-MB-231 | Human, breast adenocarcinoma | 87 ± 40 | 12 |

TABLE 2-continued

Mean EC$_{50}$ values of Formula II-16 against various tumor cell lines

| Cell line | Source | EC$_{50}$ (nM), mean ± SD * | n |
|---|---|---|---|
| MIA PaCa-2 | Human, pancreatic carcinoma | 46 | 2 |
| NCI-H292 | Human, non small cell lung carcinoma | 66 ± 29 | 12 |
| OVCAR-3 | Human, ovarian adenocarcinoma | 49 ± 31 | 6 |
| PANC-1 | Human, pancreatic carcinoma | 60 | 2 |
| PC-3 | Human, prostate adenocarcinoma | 64 ± 26 | 19 |
| RPMI 8226 | Human, multiple myeloma | 8.6 ± 1.9 | 26 |
| U266 | Human, multiple myeloma | 4.7 ± 0.7 | 6 |

* Where n (number of independent experiments) = 2, the mean value is presented

The EC$_{50}$ values indicate that Formula II-16 was cytotoxic against B16-F10, DU 145, HEK293, HT-29, LoVo, MDA-MB-231, MIA PaCa-2, NCI-H292, OVCAR-3, PANC-1, PC-3, RPMI 8226 and U266 cells.

Example 20

In Vitro Inhibition of Proteasome Activity by Formulae II-2, II-3, II-4, II-5A, II-5B, II-8C, II-13C, II-16, II-17, II-18, II-19, II-20, II-21, II-22, II-24C, II-25 and IV-3C All the compounds were prepared as 20 mM stock solution in DMSO and stored in small aliquots at −80° C. Purified rabbit muscle 20S proteasome was obtained from CalBiochem. To enhance the chymotrypsin-like activity of the proteasome, the assay buffer (20 mM HEPES, pH7.3, 0.5 mM EDTA, and 0.05% Triton X100) was supplemented with SDS resulting in a final SDS concentration of 0.035%. The substrate used was suc-LLVY-AMC, a fluorogenic peptide substrate specifically cleaved by the chymotrypsin-like activity of the proteasome. Assays were performed at a proteasome concentration of 1 µg/ml in a final volume of 200 µl in 96-well Costar microtiter plates. Formula II-2, Formula II-4, Formula II-16, Formula II-17, Formula II-18, Formula II-19, Formula II-21 and Formula II-22 were tested as eight-point dose response curves with final concentrations ranging from 500 nM to 158 pM. Formula II-5A, Formula II-5B and Formula II-20 were tested at concentrations ranging from 1 µM to 0.32 nM. Formula II-3 was tested as an eight-dose response curve with final concentrations ranging from 10 µM to 3.2 nM, while Formula II-8C, Formula II-13C, Formula II-24C, Formula II-25 and Formula IV-3C were tested with final concentrations ranging from 20 µM to 6.3 nM. The samples were incubated at 37° C. for five minutes in a temperature controlled plate reader. During the preincubation step, the substrate was diluted 25-fold in SDS-containing assay buffer. After the preincubation period, the reactions were initiated by the addition of 10 µl of the diluted substrate and the plates were returned to the plate reader. The final concentration of substrate in the reactions was 20 µM. All data were collected every five minutes for more than 1.5 hour and plotted as the mean of triplicate data points. The EC$_{50}$ values (the drug concentration at which 50% of the maximal relative fluorescence unit is inhibited) were calculated by Prism (GraphPad Software) using a sigmoidal dose-response, variable slope model. To evaluate the activity of the compounds against the caspase-like activity of the 20S proteasomes, reactions were performed as described above except that Z-LLE-AMC was used as the peptide substrate. Formulae II-3, II-4, II-5A, II-5B, II-8C, II-13C, II-17, II-18, II-20, II-21. II-22, II-24C, II-25 and Formula IV-3C were tested at concentrations ranging from 20 µM to 6.3 nM. Formula II-2 was tested at concentrations ranging from 10 µM to 3.2 nM, while Formula II-16 and Formula II-19 were tested at concentrations ranging from 5 µM to 1.58 nM. For the evaluation of the compounds against the trypsin-like activity of the proteasome, the SDS was omitted from the assay buffer and Boc-LRR-AMC was used as the peptide substrate. Formula II-20 was tested at concentrations ranging from 5 µM to 1.6 nM. Formulae II-3, II-8C, II-13C, II-17, II-21, II-22, II-24C, II-25 and IV-3C were tested at concentrations ranging from 20 µM to 6.3 nM. For Formulae II-2 and II-5B the concentrations tested ranged from 10 µM to 3.2 nM, while Formulae II-4, II-5A, II-16, II-18 and II-19 were tested at concentrations ranging from 1 µM to 0.32 nM.

Results (mean EC$_{50}$ values) are shown in Table 3 and illustrate that among the tested compounds, Formulae II-5A, II-16, II-18, II-19, II-20, II-21 and II-22 are the most potent inhibitors of the chymotrypsin-like activity of the 20S proteasome with EC$_{50}$ values ranging from 2.2 nM to 7 nM. Formulae II-2, II-4, II-5B and II-17 inhibit the proteasomal chymotrypsin-like activity with EC$_{50}$ values ranging from 14.2 nM to 87 nM, while the EC$_{50}$ value of Formula II-3 is 927 nM. Formula II-24C, II-13C and IV-3C inhibited the chymotrypsin-like activity with EC$_{50}$ values of 2.2 µM, 8.2 µM and 7.8 µM respectively. EC$_{50}$ values for Formulae II-8C and II-25 were greater than 20 µM. Under the conditions tested, Formulae II-2, II-3, II-4, II-5A, II-5B, II-13C, II-16, II-17, II-18, II-19, II-20, II-21, II-22 and II-24C were able to inhibit the trypsin-like activity of the 20S proteasome. Formulae II-4, II-5A, II-16, II-18 and II-19 inhibited the caspase-like activity with EC$_{50}$ values ranging from 250 nM to 744 nM, while Formulae II-2, II-5B, II-17, II-20, II-21, and II-22 had EC$_{50}$ values ranging from 1.2 µM to 3.3 µM.

TABLE 3

Effects of Formulae II-2, II-3, II-4, II-5A, II-5B, II-8C, II-13C, II-16, II-17, II-18, II-19, II-20, II-21, II-22, II-24C, II-25 and IV-3C on the various enzymatic activities of purified rabbit 20S proteasomes

| | EC$_{50}$ Values | | |
|---|---|---|---|
| Analog | Chymotrypsin-like | Trypsin-like | Caspase-like |
| Formula II-2 | 18 nM | 230 nM | 1.5 µM |
| Formula II-3 | 927 nM | 6.6 µM | >20 µM |
| Formula II-4 | 14.2 nM | 109 nM | 744 nM |
| Formula II-5A | 6.5 nM | 89 nM | 487 nM |
| Formula II-5B | 87 nM | 739 nM | 3.3 µM |
| Formula II-8C* | >20 µM | >20 µM | >20 µM |
| Formula II-13C | 8.2 µM | 10.7 µM | >20 µM |
| Formula II-16 | 2.5 nM | 21 nM | 401 nM |
| Formula II-17 | 29.5 nM | 588 nM | 1.2 µM |
| Formula II-18 | 2.2 nM | 14 nM | 250 nM |
| Formula II-19* | 3 nM | 13 nM | 573 nM |
| Formula II-20* | 5 nM | 318 nM | 1.4 µM |

TABLE 3-continued

Effects of Formulae II-2, II-3, II-4, II-5A, II-5B, II-8C, II-13C, II-16, II-17, II-18, II-19, II-20, II-21, II-22, II-24C, II-25 and IV-3C on the various enzymatic activities of purified rabbit 20S proteasomes

| Analog | EC$_{50}$ Values | | |
|---|---|---|---|
| | Chymotrypsin-like | Trypsin-like | Caspase-like |
| Formula II-21* | 7 nM | 720 nM | 2.6 µM |
| Formula II-22* | 5 nM | 308 nM | 1.3 µM |
| Formula II-24C* | 2.2 µM | 3.2 µM | >20 µM |
| Formula II-25* | >20 µM | >20 µM | >20 µM |
| Formula IV-3C | 7.8 µM | >20 µM | >20 µM |

*n = 1

Example 21

Salinosporamide A (II-16) Inhibits Chymotrypsin-Like Activity of Rabbit Muscle 20S Proteasomes The effect of Salinosporamide A (II-16) on proteasomes was examined using a commercially available kit from Calbiochem (catalog no. 539158), which uses a fluorogenic peptide substrate to measure the activity of rabbit muscle 20S proteasomes (Calbiochem 20S Proteasome Kit). This peptide substrate is specific for the chymotrypsin-like enzyme activity of the proteasome.

Omuralide was prepared as a 10 mM stock in DMSO and stored in 5 µL aliquots at −80° C. Salinosporamide A was prepared as a 25.5 mM solution in DMSO and stored in aliquots at −80° C. The assay measures the hydrolysis of Suc-LLVY-AMC into Suc-LLVY and AMC. The released coumarin (AMC) was measured fluorometrically by using $\lambda_{ex}$=390 nm and $\lambda_{em}$=460 nm. The assays were performed in a microtiter plate (Corning 3904), and followed kinetically with measurements every five minutes. The instrument used was a Thermo Lab Systems Fluoroskan, with the incubation chamber set to 37° C. The assays were performed according to the manufacturer's protocol, with the following changes. The proteasome was activated as described with SDS, and held on ice prior to the assay. Salinosporamide A and Omuralide were serially diluted in assay buffer to make an 8-point dose-response curve. Ten microliters of each dose were added in triplicate to the assay plate, and 190 µL of the activated proteasome was added and mixed. The samples were pre-incubated in the Fluoroskan for 5 minutes at 37° C. Substrate was added and the kinetics of AMC were followed for one hour. All data were collected and plotted as the mean of triplicate data points. The data were normalized to reactions performed in the absence of Salinosporamide A and modeled in Prism as a sigmoidal dose-response, variable slope.

Figure 27:
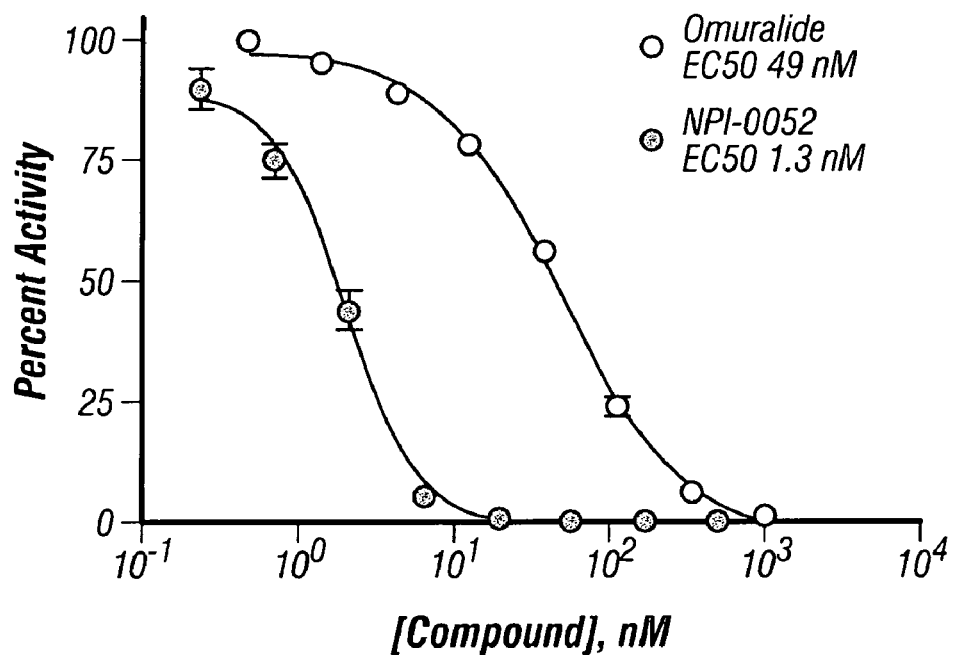
FIG. 27 shows inhibition of the chymotrypsin-like activity of rabbit muscle proteasomes.

Similar to the results obtained for the in vitro cytotoxicity (Table 2), Feling, et al., *Angew Chem Int Ed Engl* 42:355 (2003), the EC$_{50}$ values in the 20S proteasome assay showed that Salinosporamide A was approximately 40-fold more potent than Omuralide, with an average value of 1.3 nM versus 49 nM, respectively (FIG. 27). This experiment was repeated and the average EC$_{50}$ in the two assays was determined to be 2 nM for Salinosporamide A and 52 nM for Omuralide.

Salinosporamide A is a potent inhibitor of the chymotrypsin-like activity of the proteasome. The EC$_{50}$ values for cytotoxicity were in the 10-200 nM range suggesting that the ability of Salinosporamide A to induce cell death was due, at least in large part, to proteasome inhibition. The data suggest that Salinosporamide A is a potent small molecule inhibitor of the proteasome.

Example 22

Salinosporamide A (II-16) Inhibition of PGPH Activity of Rabbit Muscle 20S Proteasomes Omuralide can inhibit the PGPH activity (also known as the caspase-like) of the proteasome; therefore, the ability of Salinosporamide A to inhibit the PGPH activity of purified rabbit muscle 20S proteasomes was assessed. A commercially available fluorogenic substrate specific for the PGPH activity was used instead of the chymotrypsin substrate supplied in the proteasome assay kit described above.

Salinosporamide A (II-16) was prepared as a 20 mM solution in DMSO and stored in small aliquots at −80° C. The substrate Z-LLE-AMC was prepared as a 20 mM stock solution in DMSO, stored at −20° C. The source of the proteasomes was the commercially available kit from Calbiochem (Cat. # 539158). As with the chymotrypsin substrate, the proteasome can cleave Z-LLE-AMC into Z-LLE and free AMC. The activity can then be determined by measuring the fluorescence of the released AMC ($\lambda_{ex}$=390 nm and $\lambda_{em}$=460 nm). The proteasomes were activated with SDS and held on ice as per manufacturer's recommendation. Salinosporamide A was diluted in DMSO to generate a 400-fold concentrated 8-point dilution series. The series was diluted 20-fold with assay buffer and preincubated with the proteasomes as described for the chymotrypsin-like activity. After addition of substrate, the samples were incubated at 37° C., and release of the fluorescent AMC was monitored in a fluorimeter. All data were collected and plotted as the mean of triplicate points. In these experiments, the EC$_{50}$ was modeled in Prism as normalized activity, where the amount of AMC released in the absence of Salinosporamide A represents 100% activity. As before, the model chosen was a sigmoidal dose-response, with a variable slope.

Figure 28:
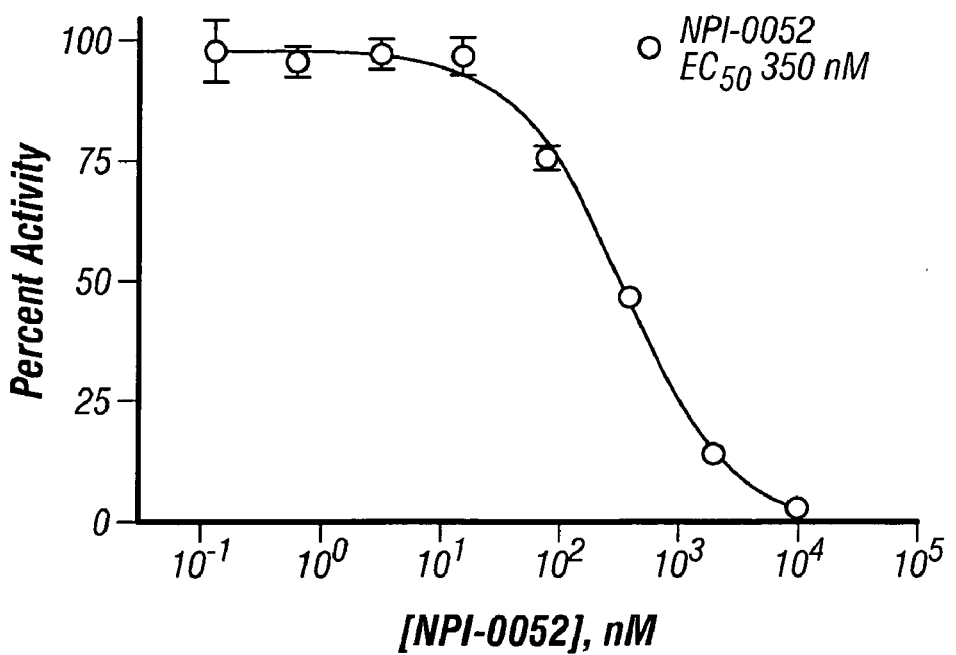
FIG. 28 shows inhibition of the PGPH activity of rabbit muscle proteasomes.

Data revealed that Salinosporamide A inhibited the PGPH activity in rabbit muscle 20S proteasomes with an EC$_{50}$ of 350 nM (FIG. 28). A replicate experiment was performed, which gave a predicted EC$_{50}$ of 610 nM. These results indicate that Salinosporamide A does block the in vitro PGPH activity of purified rabbit muscle 20S proteasomes, albeit with lower potency than seen towards the chymotrypsin-like activity.

Example 23

Inhibition of the Chymotrypsin-Like Activity of Human Erythrocyte 20S Proteasomes The ability of Salinosporamide A (II-16) to inhibit the chymotrypsin-like activity of human erythrocyte 20S proteasomes was assessed in vitro. The calculated EC$_{50}$ values ranged from 45 to 247 pM, and seemed to depend upon the lot of proteasomes tested (BIOMOL, Cat# SE-221). These data indicate that the inhibitory effect of Salinosporamide A is not limited to rabbit skeletal muscle proteasomes.

Salinosporamide A was prepared as a 20 mM solution in DMSO and stored in small aliquots at −80° C. The substrate, suc-LLVY-AMC, was prepared as a 20 mM solution in DMSO and stored at −20° C. Human erythrocyte 20S proteasomes were obtained from BIOMOL (Cat. # SE-221). The proteasome can cleave suc-LLVY-AMC into suc-LLVY and free AMC and the activity can then be determined by measuring the fluorescence of the released AMC ($\lambda_{ex}$=390 nm and $\lambda_{em}$=460 nm). The proteasomes were activated by SDS and stored on ice as with the experiments using rabbit muscle proteasomes. Salinosporamide A was diluted in DMSO to generate a 400-fold concentrated 8-point dilution series. The series was then diluted 20-fold with assay buffer and pre-incubated with proteasomes at 37° C. The reaction was initiated with substrate, and the release of AMC was followed in a Fluoroskan microplate fluorimeter. Data were collected and plotted as the mean of triplicate points. Data were captured kinetically for 3 hours, and indicated that these reactions showed linear kinetics in this time regime. The data were normalized to reactions performed in the absence of Salinosporamide A and modeled in Prism as a sigmoidal dose-response, variable slope.

Figure 29:
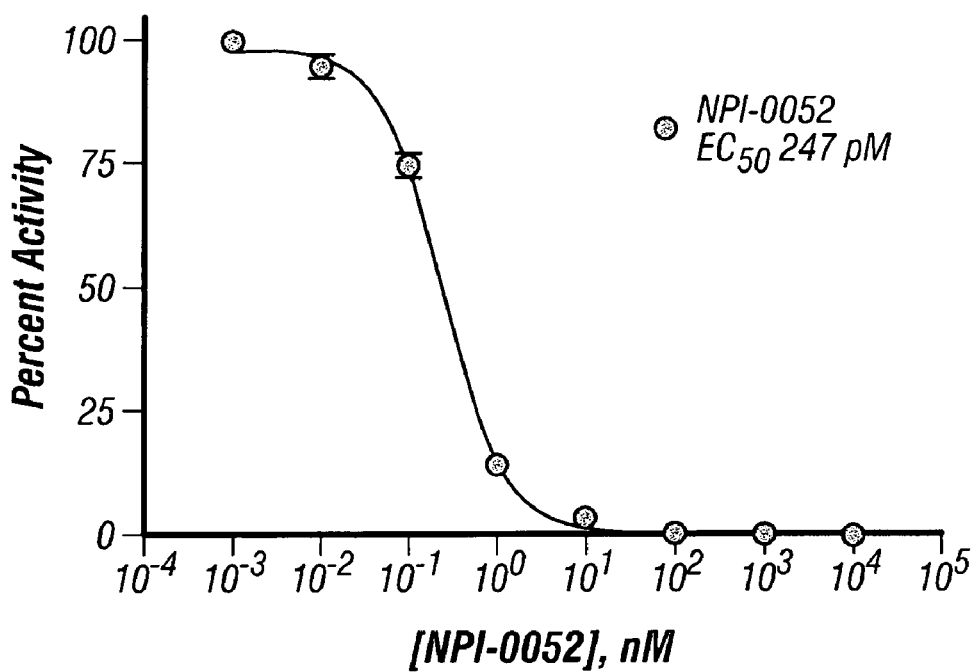
FIG. 29 shows inhibition of the chymotrypsin-like activity of human erythrocyte proteasomes.

Replicate experiments performed using human erythrocyte proteasomes from separate lots resulted in a range of $EC_{50}$ values between 45 and 250 pM (FIG. 29 shows a representative experiment). It has been reported that 20S proteasomes purified from human erythrocytes are highly heterogeneous in subunit composition. Clayerol, et al., *Mol Cell Proteomics* 1:567 (2002). The variability in these experiments may therefore be due to differences in the composition and activity of the human erythrocyte proteasome preparations. Regardless, these results indicate that the in vitro chymotrypsin-like activity of human erythrocyte 20S proteasomes is sensitive to Salinosporamide A.

Example 24

Salinosporamide A (II-16) Specificity

A possible mechanism by which Salinosporamide A inhibits the proteasome is by the reaction of the β-lactone functionality of Salinosporamide A with the active site threonine of the proteasome. This covalent modification of the proteasome would block the active site, as this residue is essential for the catalytic activity of the proteasome. Fenteany, et al., *J Biol Chem* 273:8545 (1998). A structurally related compound, Lactacystin, has been shown to also inhibit cathepsin A (Ostrowska, et al., *Int J Biochem Cell Biol* 32:747 (2000), Kozlowski, et al., *Tumour Biol* 22:211 (2001), Ostrowska, et al., *Biochem Biophys Res Commun* 234:729 (1997)) and TPPII (Geier, et al., *Science* 283:978 (1999)) but not trypsin, chymotrypsin, papain, calpain (Fenteany, et al., *Science* 268: 726 (1995)), thrombin, or plasminogen activator (Omura, et al., *J Antibiot (Tokyo)* 44:113 (1991)). Similar studies were initiated to explore the specificity of Salinosporamide A for the proteasome by evaluating its ability to inhibit the catalytic activity of a prototypical serine protease, chymotrypsin.

Salinosporamide A was prepared as a 20 mM solution in DMSO and stored in small aliquots at −80° C. The substrate, suc-LLVY-AMC, was prepared as a 20 mM solution in DMSO and stored at −20° C. Proteolytic cleavage of this substrate by either proteasomes or chymotrypsin liberates the fluorescent product AMC, which can be monitored in a fluorimeter ($\lambda_{ex}$=390 nm and $\lambda_{em}$=460 nm). Bovine pancreatic chymotrypsin was obtained from Sigma (Cat. # C-4129), and prepared as a 5 mg/ml solution in assay buffer (10 mM HEPES, 0.5 mM EDTA, 0.05% Triton X-100, pH 7.5) daily. Immediately prior to the assay, the chymotrypsin was diluted to 1 µg/ml (0.2 µg/well) in assay buffer and held on ice. Salinosporamide A was diluted in DMSO to generate an 8-point dose-response curve. The high final Salinosporamide A concentrations needed to obtain complete inhibition of chymotrypsin required that the diluted enzyme be directly added to the compound dilution series. The inclusion of 1% DMSO (the final concentration of solvent in the test wells) into the reaction had no significant effect on chymotrypsin activity towards this substrate. The reactions were pre-incubated for 5 minutes at 37° C. and the reactions were initiated by the addition of substrate. Data were collected kinetically for one hour at 37° C. in the Fluoroskan and plotted as the mean of triplicate data points. The data were normalized to reactions performed in the absence of Salinosporamide A, and modeled in Prism as a sigmoidal dose-response, variable slope. Normalized data from Salinosporamide A inhibition of the chymotrypsin-like activity of rabbit 20S proteasomes has been included on the same graph.

Figure 30:
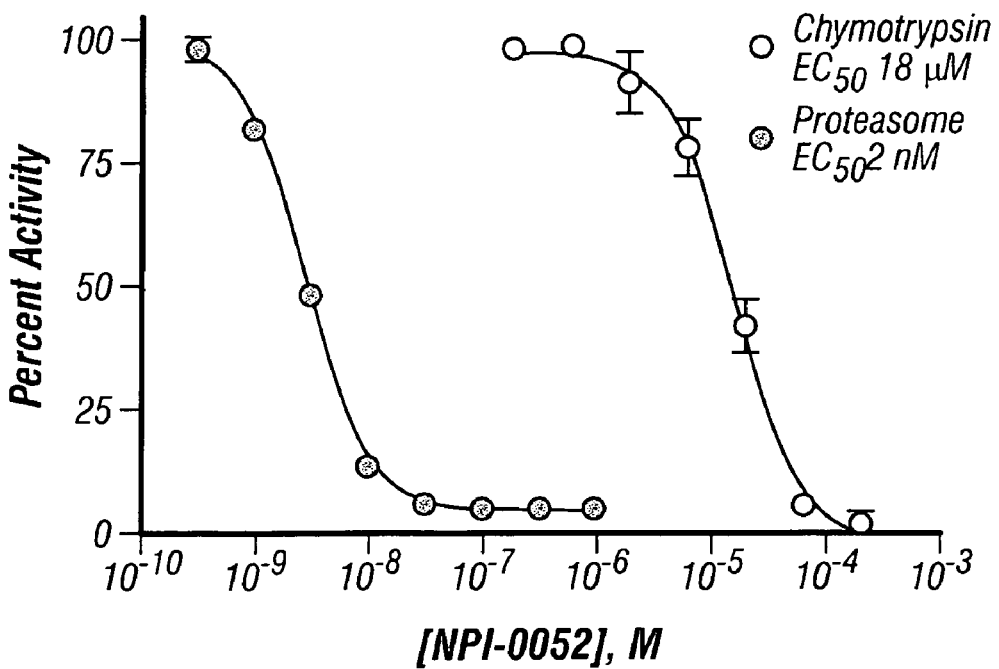
FIG. 30 shows the effect of II-16 treatment on chymotrypsin-mediated cleavage of LLVY-AMC substrate.

The average inhibition observed in two experiments using Salinosporamide A pretreatment of chymotrypsin was 17.5 µM (FIG. 30 shows a representative experiment). The data indicate that there is a preference for Salinosporamide A-mediated inhibition of the in vitro chymotrypsin-like activity of proteasomes over inhibition of the catalytic activity of chymotrypsin.

Thus, Salinosporamide A inhibits the chymotrypsin-like and PGPH activity of the proteasome. Preliminary studies indicate that Salinosporamide A also inhibits the trypsin-like activity of the proteasome with an $EC_{50}$ value of ~10 nM (data not shown).

Example 25

Inhibition of NF-κB-mediated luciferase activity by Formulae II-2, II-3, II-4, II-5A, II-5B, II-8C, II-13C, II-16, II-17, II-18, II-19, II-20, II-21, II-22, II-24C, II-25 and IV-3C; HEK293 NF-κB/Luciferase Reporter Cell Line The HEK293 NF-κB/luciferase reporter cell line is a derivative of the human embryonic kidney cell line (ATCC; CRL-1573) and carries a luciferase reporter gene under the regulation of 5×NF-κB binding sites. The reporter cell line was routinely maintained in complete DMEM medium (DMEM plus 10% (v/v) Fetal bovine serum, 2 mM L-glutamine, 10 mM HEPES and Penicillin/Streptomycin at 100 IU/ml and 100 µg/ml, respectively) supplemented with 250 µg/ml G418. When performing the luciferase assay, the DMEM basal medium was replaced with phenol-red free DMEM basal medium and the G418 was omitted. The cells were cultured in an incubator at 37° C. in 5% $CO_2$ and 95% humidified air.

For NF-κB-mediated luciferase assays, HEK293 NF-κB/luciferase cells were seeded at $1.5 \times 10^4$ cells/well in 90 µl phenol-red free DMEM complete medium into Corning 3917 white opaque-bottom tissue culture plates. For Formula II-2, Formula II-4, Formula II-5A, Formula II-16 and Formula II-18, a 400 µM starting dilution was made in 100% DMSO and this dilution was used to generate a 8-point half log dilution series. This dilution series was further diluted 40× in appropriate culture medium and ten µl aliquots were added to the test wells in triplicate resulting in final test concentrations ranging from 1 µM to 320 pM. For Formula II-3, Formula II-5B, Formula II-8C, Formula II-13C, Formula II-17, Formula II-20, Formula II-21, Formula II-22, Formula II-24C, Formula II-25 and Formula IV-3C, a 8 mM starting dilution was made in 100% DMSO and the same procedure was followed as described above resulting in final test concentrations ranging from 20 µM to 6.3 nM. For Formula II-19, a 127 µM starting dilution was made in 100% DMSO and the final test concentrations ranging from 317 nM to 0.1 nM. The plates were returned to the incubator for 1 hour. After 1 hr pretreatment, 10 µl of a 50 ng/ml TNF-α solution, prepared in the phenol-red free DMEM medium was added, and the plates were incubated for an additional 6 hr. The final concentration of DMSO was 0.25% in all samples.

At the end of the TNF-α stimulation, 100 µl of Steady Lite HTS luciferase reagent (Packard Bioscience) was added to each well and the plates were left undisturbed for 10 min at room temperature before measuring the luciferase activity. The relative luciferase units (RLU) were measured by using a Fusion microplate fluorometer (Packard Bioscience). The $EC_{50}$ values (the drug concentration at which 50% of the maximal relative luciferase unit inhibition is established) were calculated in Prism (GraphPad Software) using a sigmoidal dose response, variable slope model.

Inhibition of NF-κB Activation by Formulae II-2, II-3, II-4, II-5A, II-5B, II-8C, II-13C, II-16, II-17, II-18, II-19, II-20, II-21, II-22, II-24C, II-25 and IV-3C NF-κB regulates the expression of a large number of genes important in inflammation, apoptosis, tumorigenesis, and autoimmune diseases. In its inactive form, NF-κB complexes with IκB in the cytosol and upon stimulation, IκB is phosphorylated, ubiquitinated and subsequently degraded by the proteasome. The degradation of IκB leads to the activation of NF-κB and its translocation to the nucleus. The effects of Formula II-2, Formula II-3, Formula II-4, Formula II-5A, Formula II-5B, Formula II-8C, Formula II-13C, Formula II-16, Formula II-17, Formula II-18, Formula II-19, Formula II-20, Formula II-21, Formula II-22, Formula II-24C, Formula II-25 and Formula IV-3C on the activation of NF-κB were evaluated by assessing the NF-κB-mediated luciferase activity in HEK293 NF-κB/Luc cells upon TNF-α stimulation.

Pretreatment of NF-κB/Luc 293 cells with Formula II-2, Formula II-4, Formula II-5A, Formula II-5B, Formula II-16, Formula II-17, Formula II-18, Formula II-19, Formula II-20, Formula II-21, Formula II-22 and Formula II-24C resulted in a dose-dependent decrease of luciferase activity upon TNF-α stimulation. The mean $EC_{50}$ values to inhibit NF-κB-mediated luciferase activity are shown in Table 4 and demonstrate that compounds of Formula II-2, Formula II-4, Formula II-5A, Formula II-5B, Formula II-16, Formula II-17, Formula II-18, Formula II-19, Formula II-20, Formula II-21, Formula II-22 and Formula II-24C inhibited NF-κB activity in this cell-based assay.

TABLE 4

Mean $EC_{50}$ values of Formulae II-2, II-3, II-4, II-5A, II-5B, II-8C, II-13C, II-16, II-17, II-18, II-19, II-20, II-21, II-22, II-24C, II-25 and IV-3C from NF-κB-mediated luciferase reporter gene assay

| Compound | $EC_{50}$ (nM) |
| --- | --- |
| Formula II-2 | 82 |
| Formula II-3 | >20,000 |
| Formula II-4 | 77.7 |
| Formula II-5A | 31.5 |
| Formula II-5B | 270 |
| Formula II-8C* | >20,000 |
| Formula II-13C | >20,000 |
| Formula II-16 | 11.8 |
| Formula II-17 | 876 |
| Formula II-18 | 9.5 |
| Formula II-19 | 8.5 |
| Formula II-20* | 154 |
| Formula II-21* | 3,172 |
| Formula II-22* | 1,046 |
| Formula II-24C* | 5,298 |
| Formula II-25* | >20,000 |
| Formula IV-3C | >20,000 |

*n = 1

Example 26

Effect of Salinosporamide A on the NF-κB Signaling Pathway

Experiments were carried out to study the role of Salinosporamide A in the NF-κB signaling pathway. A stable HEK293 clone (NF-κB/Luc 293) was generated carrying a luciferase reporter gene under the regulation of 5×NF-κB binding sites. Stimulation of this cell line with TNF-α leads to increased luciferase activity as a result of NF-κB activation.

NF-κB/Luc 293 cells were pre-treated with 8-point half-log serial dilutions of Salinosporamide A (ranging from 1 µM to 317 pM) for 1 hour followed by a 6 hour stimulation with TNF-α (10 ng/mL). NF-κB inducible luciferase activity was measured at 6 hours. Viability of NF-κB/Luc 293 cells, after treatment with Salinosporamide A for 24 hr, was assessed by the addition of resazurin dye, as previously described.

Figure 31:
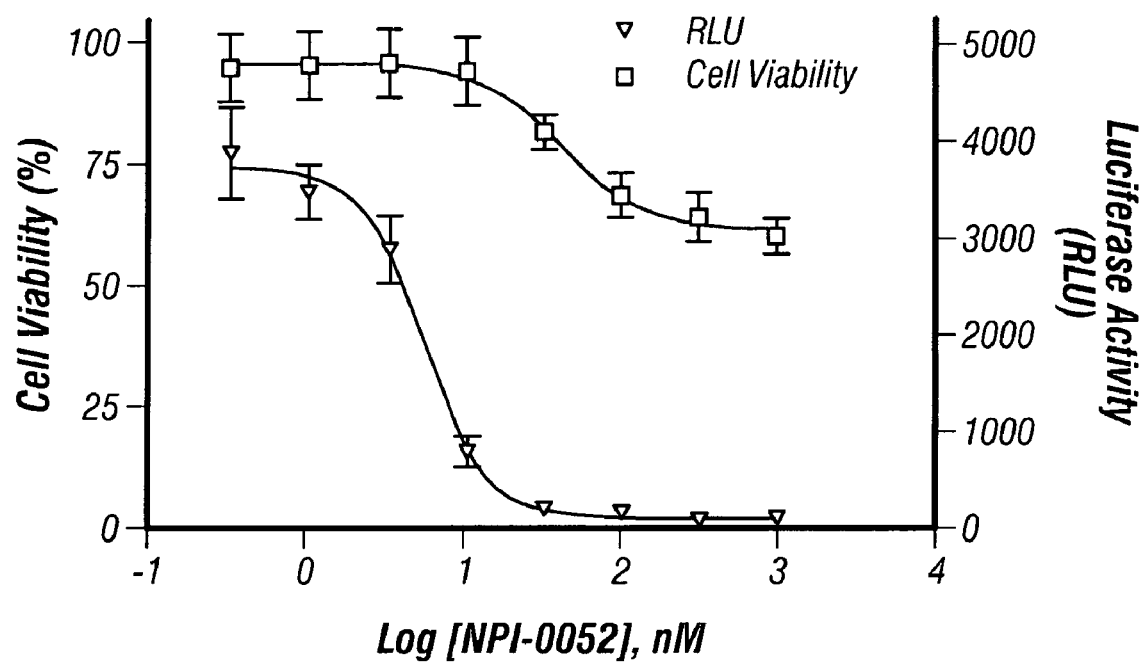
FIG. 31 shows NF-κB/luciferase activity and cytotoxicity profiles of II-16.

Pretreatment of NF-κB/Luc 293 cells with Salinosporamide A resulted in a dose-dependent decrease of luciferase activity upon TNF-α stimulation (FIG. 31, right y-axis). The calculated $EC_{50}$ for inhibition of NF-κB/luciferase activity was ~7 nM. A cytotoxicity assay was simultaneously performed, and showed that this concentration of Salinosporamide A did not affect cell viability (FIG. 31, left y-axis). These representative data suggested that the observed decrease in luciferase activity by Salinosporamide A treatment was primarily due to an NF-κB mediated-signaling event rather than cell death.

Example 27

In addition to the NF-κB luciferase reporter gene assay, the effect of Salinosporamide A on the levels of phosphorylated-IκBα and total IκBα was evaluated by western blot. Endogenous protein levels were assessed in both HEK293 cells and the NF-κB/Luc 293 reporter clone.

Cells were pre-treated for 1 hour with Salinosporamide A at the indicated concentrations followed by stimulation with 10 ng/mL of TNF-α for 30 minutes. Antibodies against total and phosphorylated forms of IκBα were used to determine the endogenous level of each protein and anti-Tubulin antibody was used to confirm equal loading of protein.

As shown in FIG. 32, treatment of both cell lines with Salinosporamide A at 50 and 500 nM not only reduced the degradation of total IκBα but also retained the phospho-IκBα level when stimulated with TNF-α. These results strongly support the mechanism of action of Salinosporamide A as a proteasome inhibitor, which prevents the degradation of phosphorylated IκBα upon TNF-α stimulation.

Example 28

Effect of Salinosporamide A on Cell Cycle Regulatory Proteins

The ubiquitin-proteasome pathway is an essential proteolytic system involved in cell cycle control by regulating the degradation of cyclins and cyclin-dependent kinase (Cdk) inhibitors such as p21 and p27. Pagano, et al., Science 269: 682 (1995), Kisselev, et al., Chem Biol 8:739 (2001), King, et al., Science 274:1652 (1996). Furthermore, p21 and p27 protein levels are increased in the presence of proteasome inhibitors. Fukuchi, et al., Biochim Biophys Acta 1451:206 (1999), Takeuchi, et al., Jpn J Cancer Res 93:774 (2002). Therefore, western blot analysis was performed to evaluate the effect of Salinosporamide A treatment on endogenous levels of p21 and p27 using the HEK293 cells and the HEK293 NF-κB/Luciferase reporter clone.

The Western blots presented in FIG. 33 were reprobed using antibodies against p21 and p27 to determine the endogenous level of each protein and anti-Tubulin antibody was used to confirm equal loading of protein.

Figure 33A:
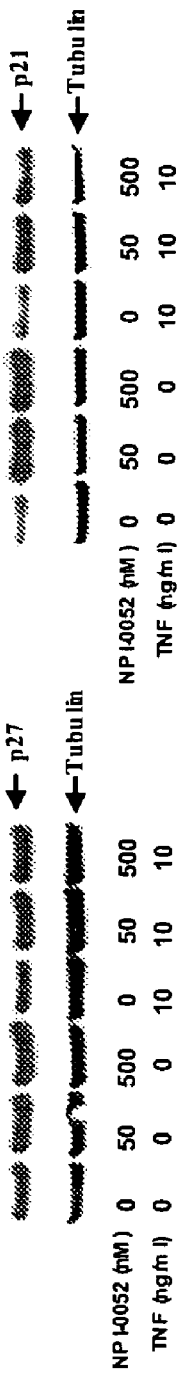
FIG. 33 shows accumulation of cell cycle regulatory proteins, p21 and p27, by II-16 treatment of HEK293 cells (A) and the HEK293 NF-κB/Luciferase reporter clone (B).
Figure 33B:
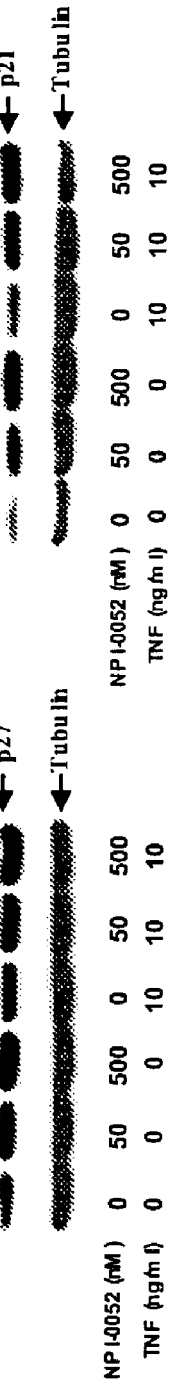

As shown in FIGS. 33A and 33B, preliminary results indicated that p21 and p27 protein levels were elevated when both cell lines were treated with Salinosporamide A at various concentrations. Data showed that Salinosporamide A acts by inhibiting proteasome activity thereby preventing the TNF-α induced activation of NF-κB. In addition, this proteasomal inhibition results in the accumulation of the Cdk inhibitors, p21 and p27, which has been reported to sensitize cells to apoptosis. Pagano, et al., supra (1995), King, et al., supra (1996).

Example 29

Activation of Caspase-3 by Salinosporamide A (II-16)

To address whether Salinosporamide A induces apoptosis, its effect on the induction of Caspase-3 activity was evaluated using Jurkat cells (American Type Culture Collection (ATCC) TIB-152, human acute T cell leukemia).

Jurkat cells were plated at $2 \times 10^6$ cells/3 mL per well in a 6-well plate and incubated at 37° C., 5% (v/v) $CO_2$ and 95% (v/v) humidity. Salinosporamide A and Mitoxantrone (Sigma, St. Louis, Mo. Cat # M6545), were prepared in DMSO at stock concentrations of 20 mM and 40 mM, respectively. Mitoxantrone is a chemotherapeutic drug that induces apoptosis in dividing and non-dividing cells via inhibition of DNA synthesis and repair and was included as a positive control. Bhalla, et al., *Blood* 82:3133 (1993). Cells were treated with $EC_{50}$ concentrations (Table 5) and incubated 19 hours prior to assessing of Caspase-3 activity. Cells treated with 0.25% DMSO served as the negative control. The cells were collected by centrifugation and the media removed. Cell pellets were processed for the Caspase-3 activity assay as described in the manufacturer's protocol (EnzChek Caspase-3 Assay Kit from Molecular Probes (E-13183; see Appendix G, which form a part of this application and is also available at hypertext transfer protocol on the worldwide web at "probes.com/media/pis/mp13183.pdf.". In brief, cell pellets were lysed on ice, mixed with the EnzChek Caspase-3 components in a 96-well plate, and then incubated in the dark for 30 minutes prior to reading fluorescence of cleaved benzyloxycarbonyl-DEVD-AMC using a Packard Fusion with $\lambda_{ex}=485$ nm and $\lambda_{em}=530$ nm filters. Protein concentrations for lysates were determined using the BCA Protein Assay Kit (Pierce) and these values were used for normalization.

Figure 34:
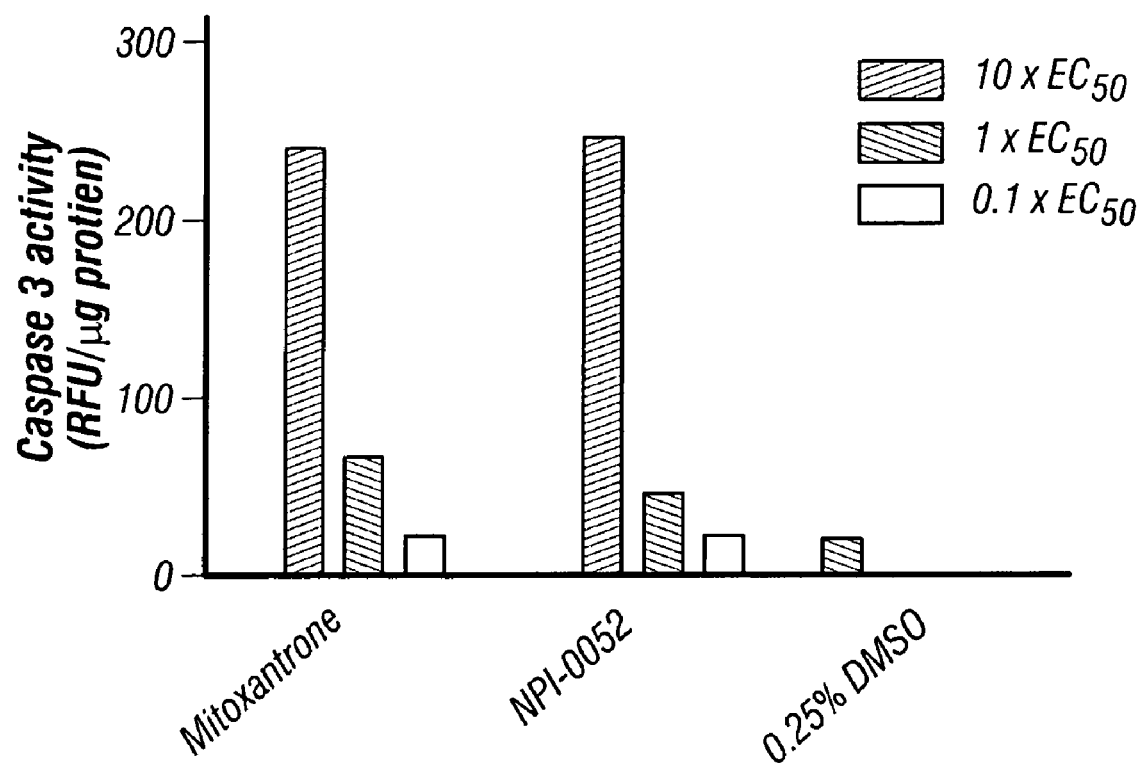
FIG. 34 shows activation of Caspase-3 by II-16 in Jurkat cells.

Data from representative experiments indicate that Salinosporamide A treatment of Jurkat cells results in cytotoxicity and activation of Caspase-3 (Table 5, FIG. 34).

TABLE 5

EC50 Values of Salinosporamide A and Mitoxantrone Cytotoxicity against Jurkat Cells

| Compound | Jurkat Cells | |
|---|---|---|
| | $EC_{50}$ (nM) | % max cell kill |
| Salinosporamide A | 10 | 97 |
| Mitoxantrone | 50 | 99 |

Example 30

PARP Cleavage by Salinosporamide A in Jurkat Cells

In order to assess the ability of Salinosporamide A to induce apoptosis in Jurkat cells, cleavage of poly (ADP-ribose) polymerase (PARP) was monitored. PARP is a 116 kDa nuclear protein that is one of the main intracellular targets of Caspase-3. Decker, et al., *J Biol Chem* 275:9043 (2000), Nicholson, D. W, Nat Biotechnol 14:297 (1996). The cleavage of PARP generates a stable 89 kDa product, and this process can be monitored by western blotting. Cleavage of PARP by caspases is a hallmark of apoptosis, and as such serves as an excellent marker for this process.

Jurkat cells were maintained in RPMI supplemented with 10% Fetal Bovine Serum (FBS) at low density ($2 \times 10^5$ cells per mL) prior to the experiment. Cells were harvested by centrifugation, and resuspended in media to $1 \times 10^6$ cells per 3 mL. Twenty mL of the cell suspension were treated with 100 nM Salinosporamide A (20 mM DMSO stock stored at −80° C.), and a 3 mL aliquot removed and placed on ice for the $T_0$ sample. Three mL aliquots of the cell suspension plus Salinosporamide A were placed in 6-well dishes and returned to the incubator. As a positive control for PARP cleavage, an identical cell suspension was treated with 350 nM Staurosporine, a known apoptosis inducer (Sigma S5921, 700 μM DMSO stock stored at −20° C.). Samples were removed at 2, 4, 6, 8, and 24 hrs in the case of Salinosporamide A treated cells, and at 4 hrs for the Staurosporine control. For each time point, the cells were recovered by brief centrifugation, the cells were washed with 400 μL of PBS, and the cells pelleted again. After removal of the PBS, the pellets were stored at −20° C. prior to SDS PAGE. Each cell pellet was resuspended in 100 μL of NuPAGE sample buffer (Invitrogen 46-5030) and 10 μL of each sample were separated on 10% NuPAGE BIS-Tris gels (Invitrogen NB302). After electrotransfer to nitrocellulose, the membrane was probed with a rabbit polyclonal antibody to PARP (Cell Signaling 9542), followed by goat anti-rabbit alkaline phosphatase conjugated secondary antibody (Jackson II-055-045). Bound antibodies were detected colorimetrically using BCIP/NBT (Roche 1681451).

Figure 35:
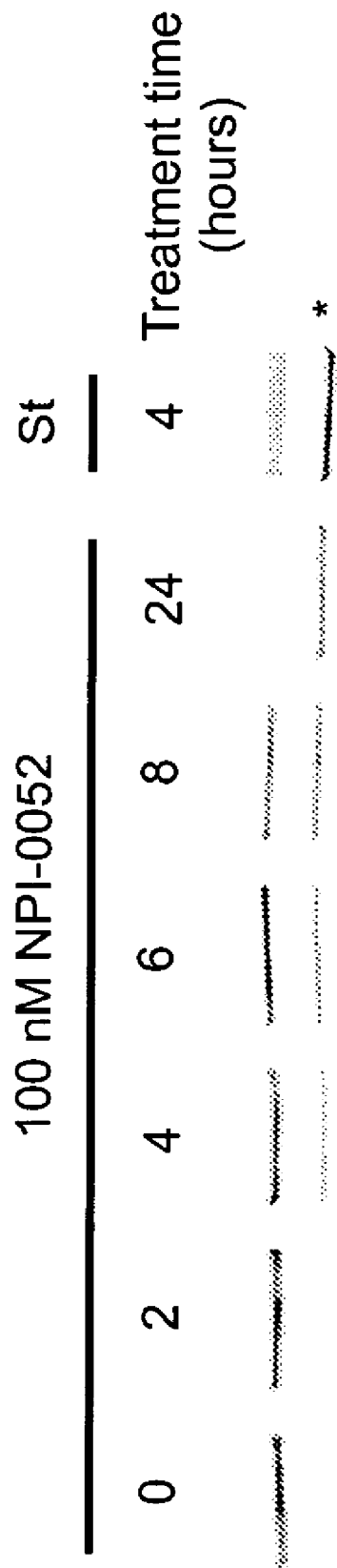
FIG. 35 shows PARP cleavage by II-16 in Jurkat cells.

The western blot presented in FIG. 35 shows the cleavage of PARP within the Jurkat cells in a time-dependent fashion. The cleaved form (denoted by the asterisk, *) appears in the treated cells between 2 and 4 hrs after exposure to Salinosporamide A while the majority of the remaining PARP is cleaved by 24 hrs. The Staurosporine treated cells (St) show rapid cleavage of PARP with most of this protein being cleaved within 4 hours. These data strongly suggest that Salinosporamide A can induce apoptosis in Jurkat cells.

Example 31

Anti-Anthrax Activity

In order to assay for the ability of Salinosporamide A or other compounds to prevent cell death resulting from LeTx exposure, RAW264.7 macrophage-like cells and recombinant LF and PA lethal toxin components were used as an in vitro model system assaying for cytotoxicity, as described below.

RAW264.7 cells (ATCC # TIB-71) were adapted to and maintained in Advanced Dulbecco's Modified Eagle Medium (Invitrogen, Carlsbad, Calif.) supplemented with 5% fetal bovine serum (ADMEM, Mediatech, Herndon, Va.) at 37° C. in a humidified 5% $CO_2$ incubator. Cells were plated overnight in ADMEM supplemented with 5% FBS at 37° C. in a humidified 5% $CO_2$ incubator at a concentration of 50,000 cells/well in a 96-well plate. Alternatively, cells cultured in DMEM supplemented with 10% fetal calf serum were also used and found to be amenable to this assay. Media was removed the following morning and replaced with serum-free ADMEM with or without Salinosporamide A or Omuralide at doses ranging from 1 µM to 0.5 nM for an 8-point dose-response. The compounds were prepared from a 1 mg/mL DMSO stock solution and diluted to the final concentration in ADMEM. After a 15 minute pre-incubation, 200 ng/mL LF or 400 ng/mL PA alone or in combination (LeTx) were added to cells. Recombinant LF and PA were obtained from List Biological Laboratories and stored as 1 mg/mL stock solutions in sterile water containing 1 mg/ml BSA at −80° C. as described by the manufacturer. Cells were incubated for 6 hours at 37° C., followed by addition of Resazurin as previously described. Plates were incubated an additional 6 hours prior to assessing cell viability by measuring fluorescence. The data are a summary of three experiments with three to six replicates per experiment and are expressed as the percent viability using the DMSO (negative) and the LeTx controls (positive) to normalize the data using the following equation: % viability=100*(observed OD−positive control)/(negative control−positive control).

Figure 36:
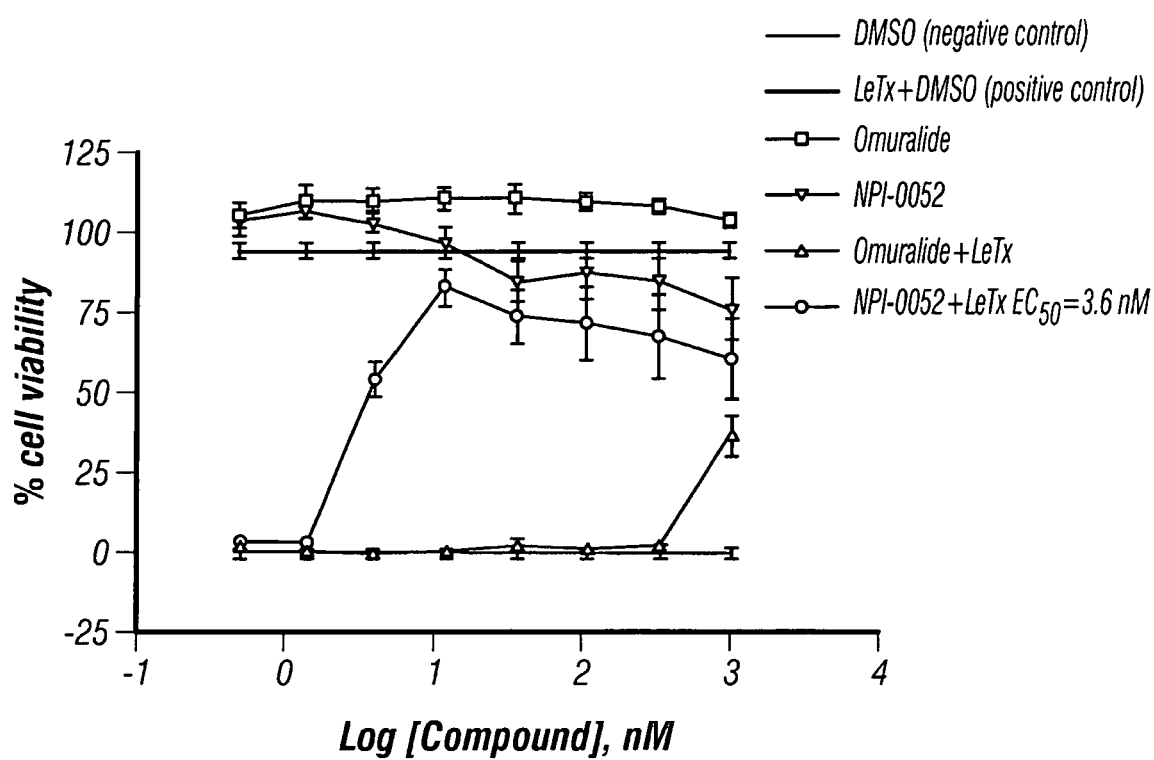
FIG. 36 shows inhibition of LeTx-induced cytotoxicity by II-16 in RAW264.7 cells.

The data represented in FIG. 36 indicate that treatment with Salinosporamide A can prevent LeTx-induced cell death of macrophage-like RAW264.7 cells in vitro. Treatment of RAW cells with either LF or PA alone or Salinosporamide A alone resulted in little reduction in cell viability, whereas treatment with LeTx resulted in approximately 0.27% cell viability as compared to controls. Salinosporamide A may enhance macrophage survival by inhibiting the degradation of specific proteins and decreasing the synthesis of cytokines, which will ultimately lead to the inhibition of the lethal effects of anthrax toxins in vivo.

Although Salinosporamide A treatment alone produced very modest cytotoxicity at concentrations of 100 nM and above, treatment with lower, relatively non-toxic levels revealed a marked increase in RAW 264.7 cell viability in LeTx treated cells (FIG. 36). For example, the Salinosporamide A+LeTx treated group showed 82% cell-viability when pretreated with 12 nM Salinosporamide A, which was a concentration that showed 96% viability with Salinosporamide A alone. The average $EC_{50}$ for Salinosporamide A in these studies was 3.6 nM. In contrast, Omuralide showed relatively little effect on cell viability until concentrations of 1 µM were reached. Even at this high concentration of Omuralide, only 37% viability was observed indicating that Salinosporamide A is a more potent inhibitor of LeTx-induced RAW264.7 cell death. Consistent with these data, Tang et. al., *Infect Immun* 67:3055 (1999), found that the $EC_{50}$ concentrations for MG132 and Lactacystin (the precursor to Omuralide) in the LeTx assay were 3 µM. Taken together, these data further illustrate that Salinosporamide A is a more potent inhibitor of LeTx-induced cytotoxicity than any other compound described to date.

Salinosporamide A promoted survival of RAW264.7 cells in the presence of LeTx indicating that this compound or it's derivatives may be a valuable clinical therapeutic for anthrax. In addition, it is worth noting that Salinosporamide A is much less cytotoxic on RAW 264.7 cells than for many tumor cells.

Example 32

Activity of Salinosporamide A Against Multiple Myeloma and Prostate Cancer Cell Lines NF-κB appears to be critical to the growth and resistance to apoptosis in Multiple Myeloma and has also been reported to be constitutively active in various prostate cancer cell lines (Hideshima T et al. 2002, Shimada K et al. 2002 and Palayoor S T et al. 1999). NF-κB activity is regulated by the proteasomal degradation of its inhibitor IκBα. Since Salinosporamide A has been shown to inhibit the proteasome in vitro and to interfere with the NF-κB signaling pathway, the activity of Salinosporamide A against the multiple myeloma cell line RPMI 8226 and the prostate cancer cell lines PC-3 and DU 145 was evaluated.

$EC_{50}$ values were determined in standard growth inhibition assays using Resazurin dye and 48 hour of drug exposure. Results from 2-5 independent experiments (Table 6) show that the $EC_{50}$ values for Salinosporamide A against RPMI 8226 and the prostate cell lines range from 10-37 nM.

TABLE 6

| | $EC_{50}$ values of Salinosporamide A (II-16) against Multiple Myeloma and Prostate Tumor cell lines | | | | | |
|---|---|---|---|---|---|---|
| | RPMI 8226 (n = 5) | | DU 145 (n = 3) | | PC-3 (n = 2) | |
| Compound | $EC_{50}$ (nM), mean ± SD | % cytotoxicity, mean ± SD | $EC_{50}$ (nM), mean ± SD | % cytotoxicity, mean ± SD | $EC_{50}$ (nM) | % cytotoxicity |
| Salinosporamide A | 10 ± 3 | 94 ± 1 | 37 ± 10 | 75 ± 4 | 31, 25 | 88, 89 |

The ability of Salinosporamide A to induce apoptosis in RPMI 8226 and PC-3 cells was evaluated by monitoring the cleavage of PARP and Pro-Caspase 3 using western blot analysis. Briefly, PC-3 and RPMI 8226 cells were treated with 100 nM Salinosporamide A (2345R01) for 0, 8 or 24 hours. Total protein lysates were made and 20 µg of the lysates were then resolved under reducing/denaturing conditions and blotted onto nitrocellulose. The blots were then probed with anti-PARP or anti-caspase 3 antibodies followed by stripping and reprobing with an anti-actin antibody.

Figure 37:
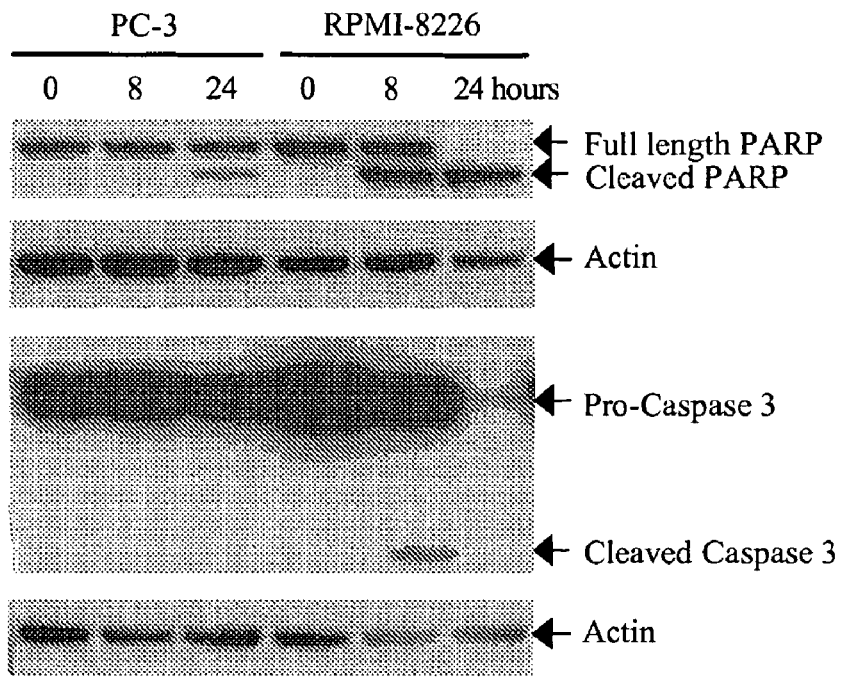
FIG. 37 shows the effects of II-16 treatment on PARP and Pro-Caspase 3 cleavage in RPMI 8226 and PC-3 cells.

Results of these experiments illustrate that Salinosporamide A treatment of RPMI 8226 cells leads to the cleavage of PARP and Pro-caspase 3 in a time-dependent manner (FIG. 37). RPMI 8226 cells seem to be more sensitive to Salinosporamide A than PC-3 cells since the induction of PARP cleavage is already noticeable at 8 hours and complete by 24 hours. In contrast, in PC-3 cells the cleavage of PARP is noticeable at 24 hours, while the cleavage of Pro-Caspase 3 is not detected in this experiment (FIG. 37).

Figure 38:
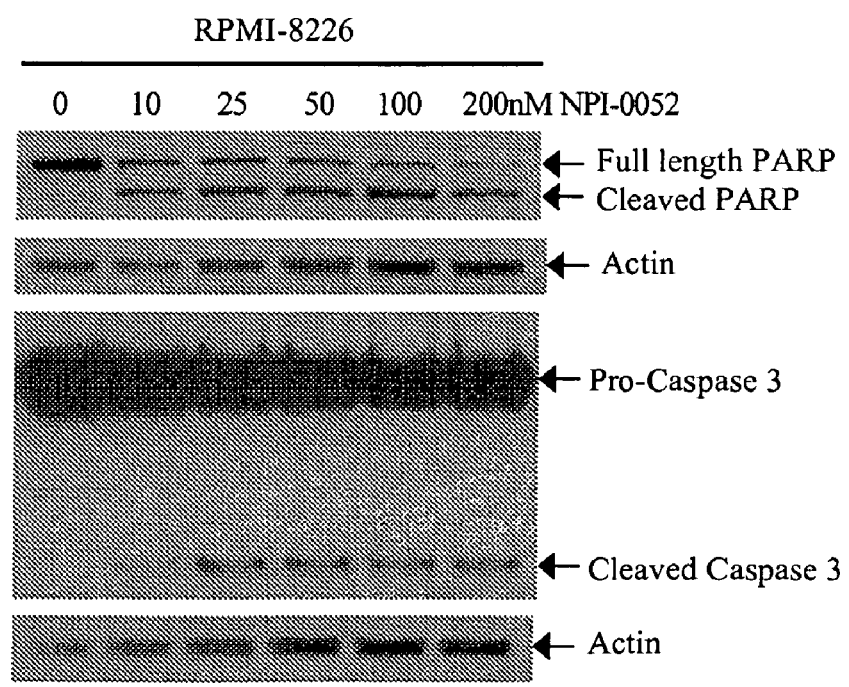
FIG. 38 shows II-16 treatment of RPMI 8226 results in a dose-dependent cleavage of PARP and Pro-Caspase 3.
Figure 39:
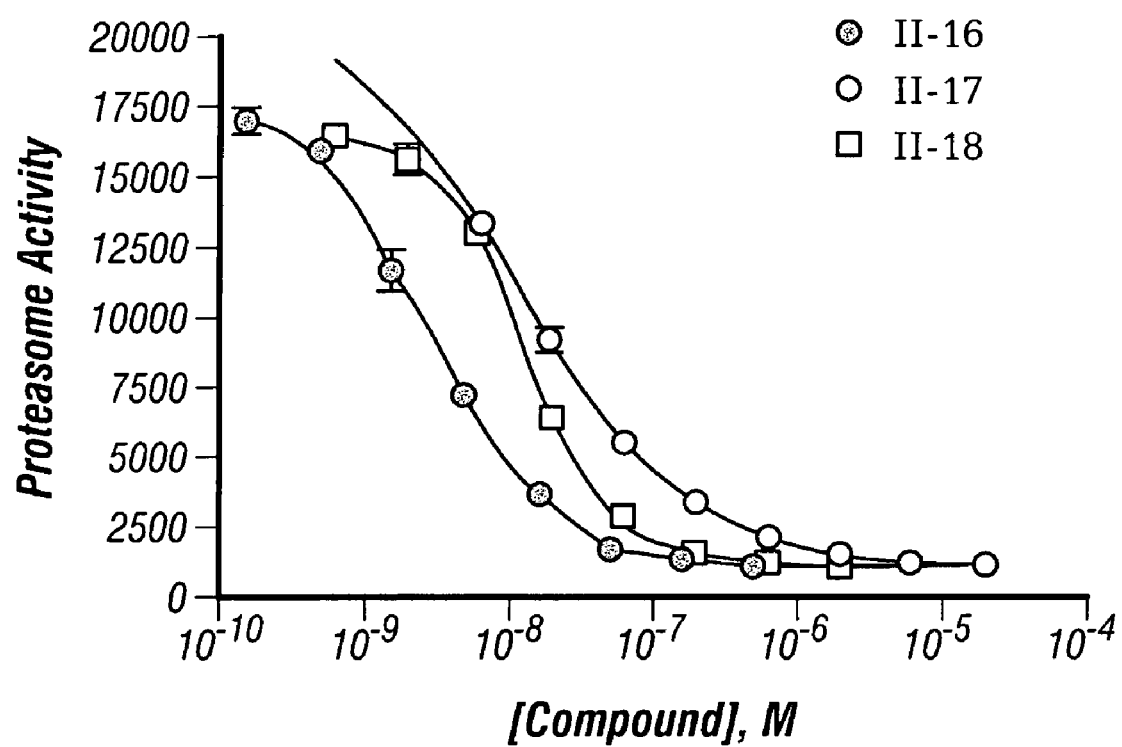
FIG. 39 shows in vitro proteasome inhibition by II-16, II-17, and II-18.

RPMI 8226 cells were used to evaluate the effect of treating the cells for 8 hours with various concentrations of Salinosporamide A. Briefly, RPMI 8226 cells were treated with varying concentrations of Salinosporamide A (2345R01) for 8 hours and protein lysates were made. 25 µg of the lysates were then resolved under reducing/denaturing conditions and blotted onto nitrocellulose. The blots were then probed with anti-PARP or anti-caspase 3 antibodies followed by stripping and reprobing with an anti-actin antibody. FIG. 38 demonstrates that Salinosporamide A induces a dose-dependent cleavage of both PARP and Pro-Caspase 3.

Example 33

Growth Inhibition of Human Multiple Myeloma by Formulae II-2, II-3, II-4, II-5A, II-5B, II-8C, II-13C, II-16, II-17, II-18, II-19, II-20, and IV-3C; RPMI 8226 and U266 cells The human multiple myeloma cell lines, RPMI 8226 (ATCC; CCL-155) and U266 (ATCC; TIB-196) were maintained in appropriate culture media. The cells were cultured in an incubator at 37° C. in 5% $CO_2$ and 95% humidified air.

For cell growth inhibition assays, RPMI 8226 cells and U266 were seeded at $2\times10^4$ and $2.5\times10^4$ cells/well respectively in 90 µl complete media into Corning 3904 black-walled, clear-bottom tissue culture plates. 20 mM stock solutions of the compounds were prepared in 100% DMSO, aliquoted and stored at –80° C. The compounds were serially diluted and added in triplicate to the test wells. The final concentration range of Formula II-3, II-8C, II-5B, II-13C, II-17, IV-3C and II-20 were from 20 µM to 6.32 nM. The final concentration of Formula II-16, II-18 and II-19 ranged from 632 nM to 200 pM. The final concentration range of Formula II-2, II-4 and II-5A were from 2 µM to 632 pM. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0, ID Business Solutions Ltd). The data are summarized in Tables 13 and 15.

Example 34

Salinosporamide A (II-16) Retains Activity Against the Multi-Drug Resistant Cell Lines MES-SA/Dx5 and HL-60/MX2

The $EC_{50}$ values of Salinosporamide A against the human uterine sarcoma MES-SA cell line and its multidrug-resistant derivative MES-SA/Dx5 were determined to evaluate whether Salinosporamide A retains activity against a cell line overexpressing the P-glycoprotein efflux pump. Paclitaxel, a known substrate for the P-glycoprotein pump was included as a control.

TABLE 7

$EC_{50}$ values of Salinosporamide A against MES-SA and the drug-resistant derivative MES-SA/Dx5

| | MES-SA | | MES-SA/Dx5 | | |
|---|---|---|---|---|---|
| | $EC_{50}$ (nM), mean | % cytotoxicity, mean ± SD | $EC_{50}$ (nM), mean ± SD | % cytotoxicity, mean ± SD | Fold change |
| Salinosporamide A | 20 ± 5 | 94 ± 1 | 23 ± 1 | 92 ± 2 | 1.2 |
| Paclitaxel | 5 ± 2 | 63 ± 7 | 2040 ± 150 | 78 ± 1 | 408 |

Results from these growth inhibition assays (Table 7) show that, as expected, Paclitaxel did not retain its activity against MES-SA/Dx5 cells as reflected by the 408 fold increase in the $EC_{50}$ values. $EC_{50}$ values for Salinosporamide A against MES-SA and MES-SA/Dx5 were similar. This illustrates that Salinosporamide A is able to inhibit the growth of the multi-drug resistant cell line MES-SA/Dx5 suggesting that Salinosporamide A does not seem to be a substrate for the P-glycoprotein efflux pump.

In addition, Salinosporamide A was evaluated against HL-60/MX2, the drug resistant derivative of the human leukemia cell line, HL-60, characterized by having a reduced Topoisomerase II activity and considered to have atypical multidrug resistance. $EC_{50}$ values for growth inhibition were determined for Salinosporamide A against the HL-60 and HL-60/MX2. The DNA binding agent Mitoxantrone was included as a control, as HL-60/MX2 cells are reported to be resistant to this chemotherapeutic agent (Harker W. G. et al. 1989).

TABLE 8

$EC_{50}$ values of Salinosporamide A against HL-60 and the drug resistant derivative HL-60/MX2

| | HL-60 | | HL-60/MX2 | | |
|---|---|---|---|---|---|
| | $EC_{50}$ (nM) | % cytotoxicity | $EC_{50}$ (nM) | % cytotoxicity | Fold change |
| Salinosporamide A | 27, 30 | 88, 91 | 28, 25 | 84, 89 | 1.0, 0.8 |
| Mitoxantrone | 59, 25 | 98, 100 | 1410, 827 | 98, 99 | 24, 33 |

The data in Table 8 reveals that Salinosporamide A was able to retain its activity against HL-60/MX2 cells relative to HL-60 cells, indicating that Salinosporamide A is active in cells expressing reduced Topoisomerase II activity. In contrast, Mitoxantrone was about 29 fold less active against HL-60/MX2 cells.

Example 35

Salinosporamide A and Several Analogs: Structure Activity Relationship

To establish an initial structure activity relationship (SAR) for Salinosporamide A, a series of Salinosporamide A analogs were evaluated against the multiple myeloma cell line RPMI 8226. $EC_{50}$ values were determined in standard growth inhibition assays using Resazurin dye and 48 hour of drug exposure.

The results of this initial series of SAR (Table 9) indicate that the addition of a halogen group to the ethyl group seems to enhance the cytotoxic activity.

TABLE 9

Initial SAR series of Salinosporamide A

| Compound No. | Molecular Structure | $EC_{50}$, μM (mean ± SD) | % Cytotoxicity (mean ± SD) |
|---|---|---|---|
| II-16 | (structure with Cl) | 0.007 ± 0.0001 | 94 ± 0 |
| II-17 | (structure with CH3) | 2.6, 2.3 | 94, 95 |
| II-18 | (structure with Br) | 0.017, 0.022 | 94, 94 |

Where n > 2, mean ± standard deviation was determined

Example 36

In Vivo Biology

Maximum Tolerated Dose (MTD) Determination

In vivo studies were designed to determine the MTD of Salinosporamide A when administered intravenously to female BALB/c mice.

BALB/c mice were weighed and various Salinosporamide A concentrations (ranging from 0.01 mg/kg to 0.5 mg/kg) were administered intravenously as a single dose (qdx1) or daily for five consecutive days (qdx5). Animals were observed daily for clinical signs and were weighed individually twice weekly until the end of the experiment (maximum of 14 days after the last day of dosing). Results are shown in Table 11 and indicate that a single intravenous Salinosporamide A dose of up to 0.25 mg/kg was tolerated. When administered daily for five consecutive days, concentrations of Salinosporamide A up to 0.1 mg/kg were well tolerated. No behavioral changes were noted during the course of the experiment.

TABLE 11

MTD Determination of Salinosporamide A in female BALB/c Mice

| Group | Dose (mg/kg) | Route/Schedule | Deaths/Total | Days of Death |
|---|---|---|---|---|
| 1 | 0.5 | i.v.; qdx1 | 3/3 | 3, 3, 4 |
| 2 | 0.25 | i.v.; qdx1 | 0/3 | |
| 3 | 0.1 | i.v.; qdx1 | 0/3 | |
| 4 | 0.05 | i.v.; qdx1 | 0/3 | |
| 5 | 0.01 | i.v.; qdx1 | 0/3 | |
| 6 | 0 | i.v.; qdx1 | 0/3 | |
| 7 | 0.5 | i.v.; qdx5 | 3/3 | 4, 6, 7 |
| 8 | 0.25 | i.v.; qdx5 | 3/3 | 4, 5, 5 |
| 9 | 0.1 | i.v.; qdx5 | 0/3 | |
| 10 | 0.05 | i.v.; qdx5 | 0/3 | |
| 11 | 0.01 | i.v.; qdx5 | 0/3 | |
| 12 | 0 | i.v.; qdx5 | 0/3 | |

Example 37

Preliminary Assessment of Salinosporamide A Absorption, Distribution, Metabolism and Elimination (ADME) characteristics Studies to initiate the evaluation of the ADME properties of Salinosporamide A were performed. These studies consisted of solubility assessment, $LogD^{7.4}$ determination and a preliminary screen to detect cytochrome P450 enzyme inhibition. Results from these studies showed an estimated solubility of Salinosporamide A in PBS (pH 7.4) of 9.6 μM (3 μg/ml) and a $LogD^{7.4}$ value of 2.4. This $LogD^{7.4}$ value is within the accepted limits compatible with drug development ($LogD^{7.4}$<5.0) and suggests oral availability. Results from the preliminary P450 inhibition screen showed that Salinosporamide A, when tested at 10 μM, showed no or low inhibition of all P450 isoforms: CYP1A2, CYP2C9 and CYP3A4 were inhibited by 3%, 6% and 6% respectively, while CYP2D6 and CYP2C19 were inhibited by 19% and 22% respectively.

Example 38

Salinosporamide A and its effects in vivo on whole blood proteasome activity Salinosporamide A was previously demonstrated to be a potent and specific inhibitor of the proteasome in vitro, with an $IC_{50}$ of 2 nM towards the chymotrypsin-like activity of purified 20S proteasomes. To monitor the activity of Salinosporamide A in vivo, a rapid and reproducible assay (adapted from Lightcap et al. 2000) was developed to assess the proteasome activity in whole blood.

In brief, frozen whole blood samples were thawed on ice for one hour, and resuspended in 700 μL of ice cold 5 mM EDTA, pH 8.0 in order to lyse the cells by hypotonic shock.

This represents approximately 2-3 times the volume of the packed whole blood cells. Lysis was allowed to proceed for one hour, and the cellular debris was removed by centrifugation at 14,000×g for 10 minutes. The supernatant (Packed Whole Blood Lysate, PWBL) was transferred to a fresh tube, and the pellet discarded. Protein concentration of the PWBL was determined by BCA assay (Pierce) using BSA as a standard. Approximately 80% of the samples had a total protein concentration between 800 and 1200 µg/mL.

Proteasome activity was determined by measuring the hydrolysis of a fluorogenic substrate specific for the chymotrypsin-like activity of proteasomes (suc-LLVY-AMC, Bachem Cat. 1-1395). Control experiments indicated that >98% of the hydrolysis of this peptide in these extracts is mediated by the proteasome. Assays were set up by mixing 5 µL of a PWBL from an animal with 185 µL of assay buffer (20 mM HEPES, 0.5 mM EDTA, 0.05% Triton X-100, 0.05% SDS, pH 7.3) in Costar 3904 plates. Titration experiments revealed there is a linear relationship between protein concentration and hydrolysis rate if the protein concentration in the assay is between 200 and 1000 µg. The reactions were initiated by the addition of 10 µL of 0.4 mM suc-LLVY-AMC (prepared by diluting a 10 mM solution of the peptide in DMSO 1:25 with assay buffer), and incubated in a fluorometer (Labsystems Fluoroskan) at 37° C. Hydrolysis of the substrate results in the release of free AMC, which was measured fluorometrically by using $\lambda_{ex}$=390 nm and $\lambda_{em}$=460 nm. The rate of hydrolysis in this system is linear for at least one hour. The hydrolysis rate of each sample is then normalized to relative fluorescent units per milligram of protein (RFU/mg).

To explore the in vivo activity of Salinosporamide A, male Swiss-Webster mice (5 per group, 20-25 g in weight) were treated with various concentrations of Salinosporamide A. Salinosporamide A was administered intravenously and given its $LogD^{7.4}$ value of 2.4, suggestive of oral availability, Salinosporamide A was also administered orally. Salinosporamide A dosing solutions were generated immediately prior to administration by dilution of Salinosporamide A stock solutions (100% DMSO) using 10% solutol yielding a final concentration of 2% DMSO. The vehicle control consisted of 2% DMSO in 10% solutol. One group of animals was not dosed with either vehicle or Salinosporamide A in order to establish a baseline for proteasome activity. Salinosporamide A or vehicle was administered at 10 mL/kg and ninety minutes after administration the animals were anesthetized and blood withdrawn by cardiac puncture. Packed whole blood cells were collected by centrifugation, washed with PBS, and re-centrifuged. All samples were stored at −80° C. prior to the evaluation of the proteasome activity.

In order to be certain that the hydrolysis of the substrate observed in these experiments was due solely to the activity of the proteasome, dose response experiments on the extracts were performed using the highly specific proteasomal inhibitor Epoxomicin. PWBL lysates were diluted 1:40 in assay buffer, and 180 µL were added to Costar 3904 plates. Epoxomicin (Calbochem Cat. 324800) was serially diluted in DMSO to generate an eight point dose response curve, diluted 1:50 in assay buffer, and 10 µL added to the diluted PWBL in triplicate. The samples were preincubated for 5 minutes at 37° C., and the reactions initiated with substrate as above. The dose response curves were analyzed in Prism, using a sigmoidal dose response with variable slope as a model.

Figure 40:
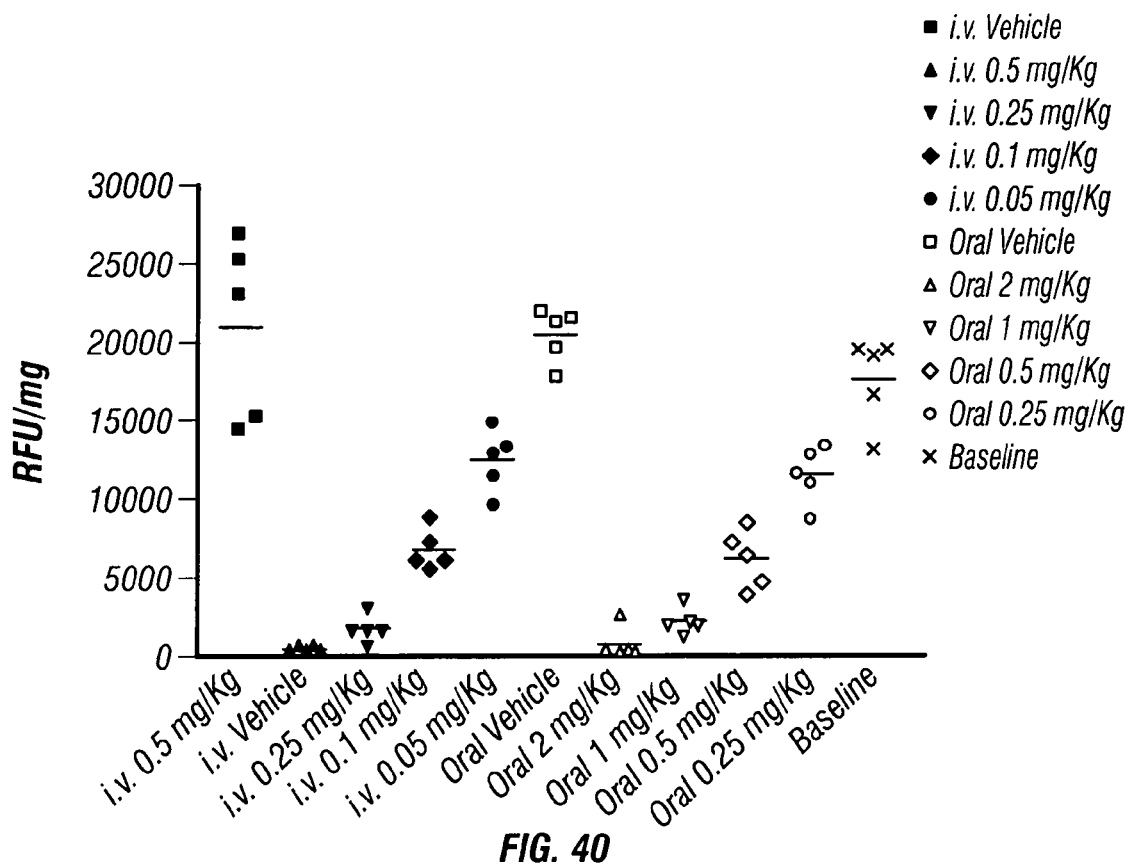
FIG. 40 shows proteasomal activity in PWBL prepared from II-16 treated mice.

FIG. 40 is a scatter plot displaying the normalized proteasome activity in PWBL's derived from the individual mice (5 mice per group). In each group, the horizontal bar represents the mean normalized activity. These data show that Salinosporamide A causes a profound decrease in proteasomal activity in PWBL, and that this inhibition is dose dependent. In addition, these data indicate that Salinosporamide A is active upon oral administration.

Figure 41:
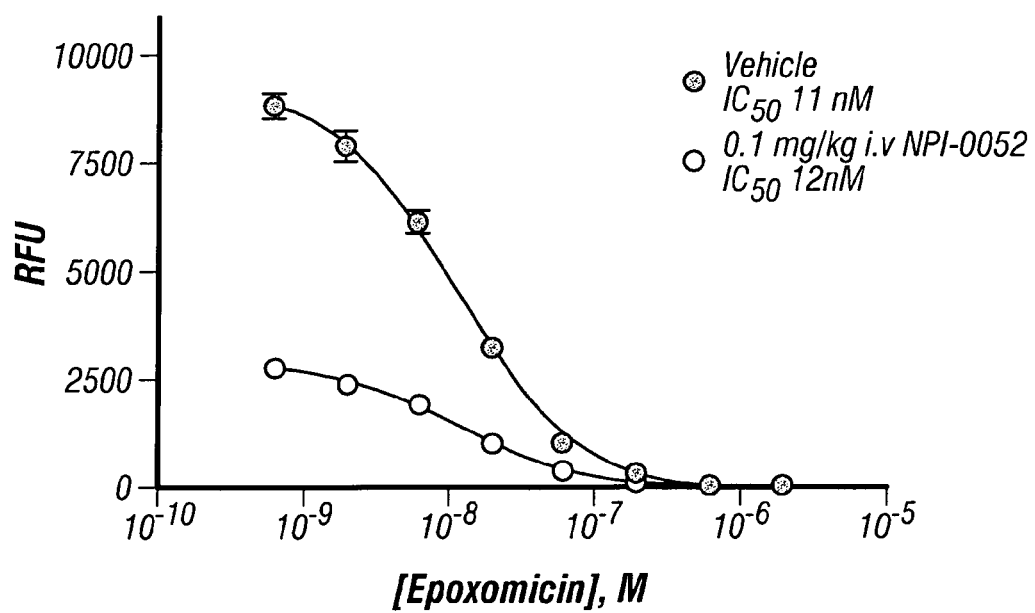
FIG. 41 shows epoxomicin treatment in the PWBL assay.

The specificity of the assay was shown by examining the effect of a known proteasome inhibitor, Epoxomicin, on hydrolysis of the peptide substrate. Epoxomicin is a peptide epoxide that has been shown to highly specific for the proteasome, with no inhibitory activity towards any other known protease (Meng et al., 1999). Lysates from a vehicle control and also from animals treated intravenous (i.v.) with 0.1 mg/kg Salinosporamide A were incubated with varying concentration of Epoxomicin, and $IC_{50}$ values were determined. Palayoor et al., *Oncogene* 18:7389-94 (1999). As shown in FIG. 41, Epoxomicin caused a dose dependent inhibition in the hydrolysis of the proteasome substrate. The $IC_{50}$ obtained in these experiments matches well with the 10 nM value observed using purified 20S proteasomes in vitro (not shown). These data also indicate that the remaining activity towards this substrate in these lysates prepared from animals treated with 0.1 mg/kg Salinosporamide A is due to the proteasome, and not some other protease. The residual activity seen in extracts treated with high doses of Epoxomicin is less than 2% of the total signal, indicating that over 98% of the activity observed with suc-LLVY-AMC as a substrate is due solely to the activity of the proteasomes present in the PWBL.

Figure 42:
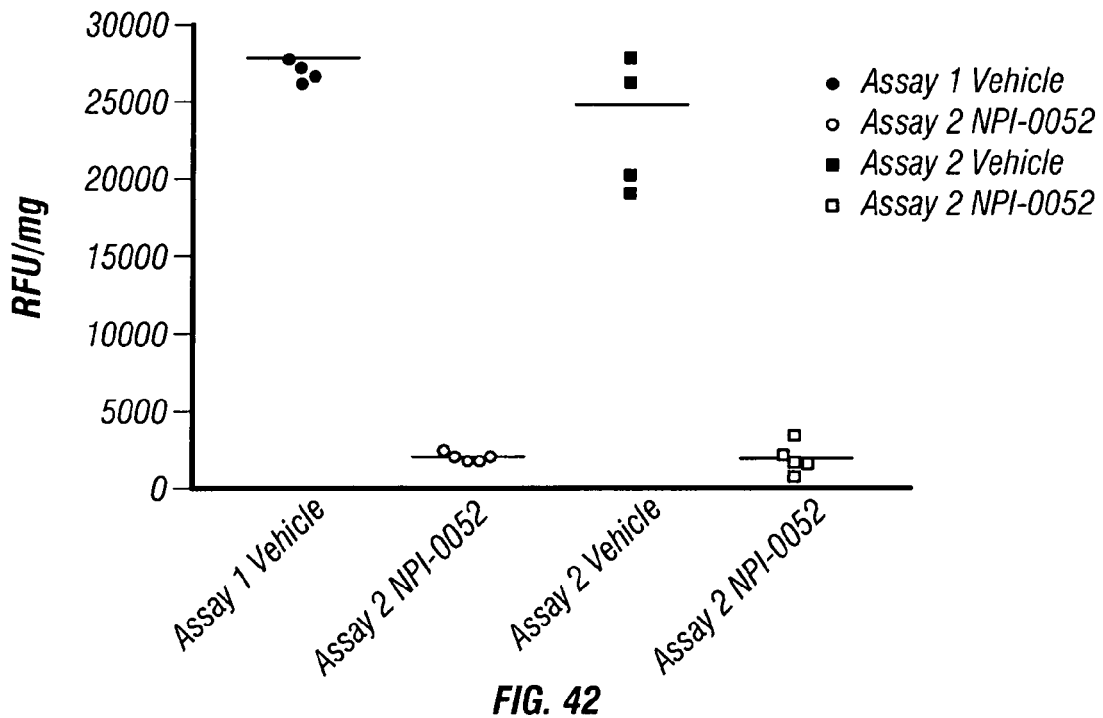
FIG. 42 shows intra-assay comparison.

Comparison of intra-run variation in baseline activity and the ability of Salinosporamide A to inhibit proteasomal activity was also assessed. In FIG. 42, the results of separate assays run several weeks apart are shown. Qureshi, et al., *J. Immunol.* 171(3):1515-25 (2003). For clarity, only the vehicle control and matching dose results are shown. While there was some variation in the proteasomal activity in PWBL derived from individual animals in the control groups, the overall mean was very similar between the two groups. The animals treated with Salinosporamide A (0.1 mg/kg i.v.) also show very similar residual activity and average inhibition. This suggests that results between assays can be compared with confidence.

Example 39

Inhibition of In Vivo LPS-Induced TNF by Salinosporamide A

Studies suggest that the proteasome plays a role in the activation of many signaling molecules, including the transcription factor NF-κB via protealytic degradation of the inhibitor of NF-κB (IκB). LPS signaling through the TLR4 receptor activates NF-κB and other transcriptional regulators resulting in the expression of a host of proinflammatory genes like TNF, IL-6, and IL-1β. The continued expression of proinflammatory cytokines has been identified as a major factor in many diseases. Inhibitors of TNF and IL-1β have shown efficacy in many inflammation models including the LPS murine model, as well as animal models of rheumatoid arthritis and inflammatory bowel disease. Recent studies have suggested that inhibition of the proteasome can prevent LPS-induced TNF secretion (Qureshi et al., 2003). These data suggest that Salinosporamide A, a novel potent proteasome inhibitor, may prevent TNF secretion in vivo in the high-dose LPS murine model.

To assess the ability of Salinosporamide A to inhibit in vivo LPS-induced plasma TNF levels in mice, in vivo studies were initiated at BolderBioPATH, Inc. in Boulder, Colo. The following methods outline the protocol design for these studies.

Male Swiss Webster mice (12/group weighing 20-25 g) were injected with LPS (2 mg/kg) by the i.p. route. Thirty minutes later, mice were injected i.v. (tail vein) with Salinosporamide A at 2.5 mg/kg after approximately 5 minutes under a heat lamp. Ninety minutes after LPS injection, the mice were anesthetized with Isoflurane and bled by cardiac puncture to obtain plasma. Remaining blood pellet was then resuspended in 500 µL of PBS to wash away residual serum proteins and centrifuged again. Supernatant was removed and blood pellet frozen for analysis of proteasome inhibition in packed whole blood lysate.

TABLE 12

| Group ID | Group | Time n = 0 min | +30 min |
|---|---|---|---|
| No injections/baseline | 1 | 5 | |
| Saline + solutol vehicle | 2 | 5 saline | |
| Saline + solutol vehicles | 3 | 5 saline | Solutol/DMSO |
| LPS i.p./Vehicle (−30 min) | 4 | 12 LPS | |
| LPS i.p./Vehicle (+30 m) | 5 | 12 LPS | Solutol/DMSO |
| saline/Salinosporamide A (−30 min) 0.25 mg/kg | 6 | 12 saline | |
| saline/Salinosporamide A (+30 m) 0.25 mg/kg | 7 | 12 saline | 0.25 mg/kg |
| LPS/Salinosporamide A (−30 min) 0.25 mg/kg | 8 | 12 LPS | |
| LPS/Salinosporamide A (+30 m) 0.25 mg/kg | 9 | 12 LPS | 0.25 mg/kg |

Dosing solutions were prepared using a 10 mg/mL Salinosporamide A stock solution in 100% DMSO. A 10% solutol solution was prepared by diluting w/w with endotoxin-free water and a 1:160 dilution was made of the 10 mg/ml Salinosporamide A stock. Animals were dosed i.v. with 4 ml/kg. A vehicle control solution was also prepared by making the same 1:160 dilution with 100% DMSO into 10% solutol solution giving a final concentration of 9.375% solutol in water and 0.625% DMSO. Measurements of plasma TNF were performed using the Biosource mTNF Cytoset kit (Biosource Intl., Camarillo, Calif.; catalog #CMC3014) according to manufacturer's instructions. Samples were diluted 1:60 for the assay.

Figure 43:
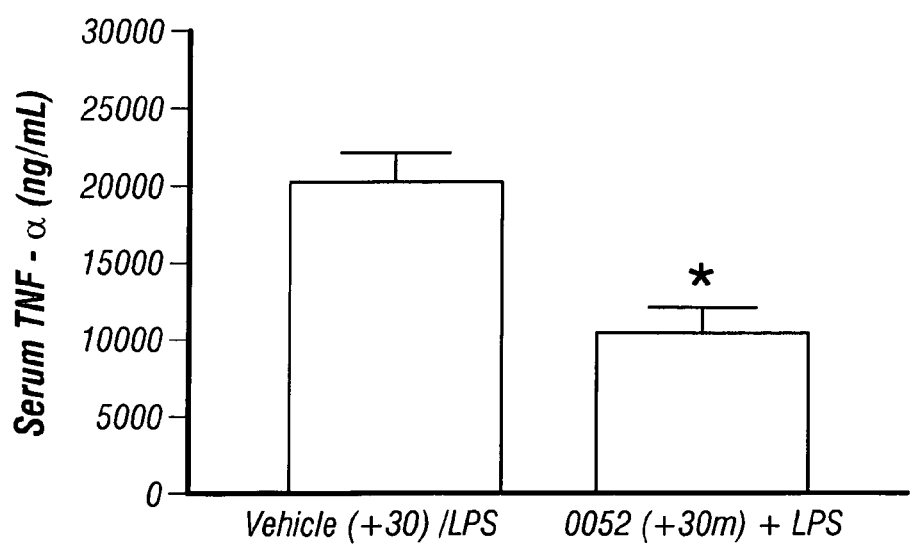
FIG. 43 shows decreased plasma TNF levels in mice treated with LPS.

Data from two independent experiments with at least ten replicate animals per group indicated that treatment with 0.125 or 0.25 mg/kg Salinosporamide A decreased LPS-induced TNF secretion in vivo. A representative experiment is shown in FIG. 43. These data reveal that treatment of animals with 0.25 mg/kg Salinosporamide A thirty minutes after 2 mg/kg LPS injection resulted in significant reduction in serum TNF levels. Packed whole blood samples were also analyzed for ex vivo proteasome inhibition revealing 70±3% inhibition in animals treated with 0.125 mg/kg and 94±3% in animals treated with 0.25 mg/kg. No significant differences were seen in proteasome inhibition in animals treated with or without LPS. Salinosporamide A reduces LPS-induced plasma TNF levels by approximately 65% when administered at 0.125 or 0.25 mg/kg i.v. into mice 30 minutes post-LPS treatment.

Example 40

Potential In Vitro Chemosensitizing Effects of Salinosporamide A

Chemotherapy agents such as CPT-11 (Irinotecan) can activate the transcription factor nuclear factor-kappa B (NF-κB) in human colon cancer cell lines including LoVo cells, resulting in a decreased ability of these cells to undergo apoptosis. Cusack, et al., *Cancer Res* 61:3535 (2001). In unstimulated cells, NF-κB resides in the cytoplasm in an inactive complex with the inhibitory protein IκB (inhibitor of NF-κB). Various stimuli can cause IκB phosphorylation by IκB kinase, followed by ubiquitination and degradation of IκB by the proteasome. Following the degradation of IκB, NF-κB translocates to the nucleus and regulates gene expression, affecting many cellular processes, including upregulation of survival genes thereby inhibiting apoptosis.

The recently approved proteasome inhibitor, Velcade™ (PS-341; Millennium Pharmaceuticals, Inc.), is directly toxic to cancer cells and can also enhance the cytotoxic activity of CPT-11 against LoVo cells in vitro and in a LoVo xenograft model by inhibiting proteasome induced degradation of IκB. Adams, J., *Eur J Haematol* 70:265 (2003). In addition, Velcade™ was found to inhibit the expression of proangiogenic chemokines/cytokines GRO-α and VEGF in squamous cell carcinoma, presumably through inhibition of the NF-κB pathway. Sunwoo, et al., *Clin Cancer Res* 7:1419 (2001). The data indicate that proteasome inhibition may not only decrease tumor cell survival and growth, but also angiogenesis.

Example 41

Growth inhibition of Colon, Prostate, Breast, Lung, Ovarian, Multiple Myeloma and Melanoma Human colon adenocarcinoma (HT-29; HTB-38), prostate adenocarcinoma (PC-3; CRL-1435), breast adenocarcinoma (MDA-MB-231; HTB-26), non-small cell lung carcinoma (NCI-H292; CRL-1848), ovarian adenocarcinoma (OVCAR-3; HTB-161), multiple myeloma (RPMI 8226; CCL-155), multiple myeloma (U266; TIB-196) and mouse melanoma (B16-F10; CRL-6475) cells were all purchased from ATCC and maintained in appropriate culture media. The cells were cultured in an incubator at 37° C. in 5% $CO_2$ and 95% humidified air.

For cell growth inhibition assays, HT-29, PC-3, MDA-MB-231, NCI-H292, OVCAR-3 and B16-F10 cells were seeded at $5\times10^3$, $5\times10^3$, $1\times10^4$, $4\times10^3$, $1\times10^4$ and $1.25\times10^3$ cells/well respectively in 90 µl complete media into 96 well (Corning; 3904) black-walled, clear-bottom tissue culture plates and the plates were incubated overnight to allow cells to establish and enter log phase growth. RPMI 8226 and U266 cells were seeded at $2\times10^4$ and $2.5\times10^4$ cells/well respectively in 90 µl complete media into 96 well plates on the day of the assay. 20 mM stock solutions of the compounds were prepared in 100% DMSO and stored at −80° C. The compounds were serially diluted and added in triplicate to the test wells. Concentrations ranging from 6.32 µM to 632 pM were tested for II-2 and II-4. II-3 and II-17 were tested at concentrations ranging from 20 µM to 6.32 nM. Formula II-18 and II-19 were tested at concentrations ranging from 2 µM to 200 pM. Formula II-5A and Formula II-5B were tested at final concentrations ranging from 204 to 632 pM and 20 µM to 6.32 nM respectively. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience)

with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an $EC_{50}$ value was not determined.

The data in Table 13 summarize the growth inhibitory effects of Formulae II-2, II-3, II-4, II-5A, II-5B, II-17, II-18 and II-19 against the human colorectal carcinoma, HT-29, human prostate carcinoma, PC-3, human breast adenocarcinoma, MDA-MB-231, human non-small cell lung carcinoma, NCI-H292, human ovarian carcinoma, OVCAR-3, human multiple myelomas, RPMI 8226 and U266 and murine melanoma B16-F10 cell lines.

TABLE 15

Mean $EC_{50}$ values of Formulae II-2, II-3, II-4, II-5A, II-5B, II-8C, II-13C, II-16, II-17, II-18, II-19, IV-3C and Formula II-20 against RPMI 8226 and U266 cells

| Compound | RPMI 8226 $EC_{50}$ (nM) | U266 $EC_{50}$ (nM) |
|---|---|---|
| Formula II-17 | 4800 | 1670 |
| Formula II-16 | 7.0 | 4.1 |
| Formula II-18 | 6.3 | 4.2 |
| Formula II-2 | 47 | 36 |
| Formula II-3 | >20000 | >20000 |
| Formula II-4 | 54 | 36 |
| Formula II-5A | 33 | 10 |
| Formula II-5B | 327 | 115 |
| Formula II-8C | >20000 | >20000 |
| Formula II-13C | >20000 | >20000 |
| Formula II-19 | 6.5 | 3.3 |
| Formula IV-3C | >20000 | 8020 |
| Formula II-20* | 10500 | 3810 |

*n = 1

TABLE 13

$EC_{50}$ values of Formulae II-2, II-3, II-4, II-5A, II-5B, II-17, II-18 and II-19 against various tumor cell lines

| Cell line | $EC_{50}$ (nM)* | | | | | | | |
|---|---|---|---|---|---|---|---|---|
| | II-2 | II-3 | II-4 | II-5A | II-5B | II-17 | II-18 | II-19 |
| HT-29 | 129 ± 21 | >20000 | 132 ± 36 | 85 | 1070 | >20000 | 18 ± 7.8 | 13 |
| PC-3 | 284 ± 110 | >20000 | 204 ± 49 | 97 | 1330 | >20000 | 35 ± 5.6 | 27 |
| MDA-MB-231 | 121 ± 23 | >20000 | 114 ± 4 | 66 | 1040 | 5900 ± 601 | 16 ± 2.8 | 17 |
| NCI-H292 | 322 | >20000 | 192 | 90 | >20000 | >20000 | 29 | 31 |
| | 395 | >20000 | 213 | | | >20000 | 41 | |
| OVCAR-3 | 188 | >20000 | >6320 | NT | NT | >20000 | >2000 | NT |
| | 251 | | >6320 | | | >20000 | >2000 | |
| RPMI 8226 | 49 | >20000 | 57 | 36 | 326 | 6200 | 6.3 | 5.9 |
| | 45 | >20000 | 51 | 29 | 328 | 3500 | 6.3 | 7.1 |
| U266 | 39 | >20000 | 39 | 10 | 118 | 1620 | 4.2 | 3.2 |
| | 32 | >20000 | 34 | 9 | 111 | 1710 | 4.2 | 3.4 |
| B16-F10 | 194 | >20000 | 163 | NT | NT | 10500 | 19 | NT |
| | 180 | >20000 | 175 | | | 10300 | 36 | |

*Where n = 3, mean ± standard deviation is presented;
NT = not tested

The $EC_{50}$ values indicate that the Formulae II-2, II-4 and II-18 were cytotoxic against the HT-29, PC-3, MDA-MB-231, NCI-H292, RPMI 8226, U266 and B16-F10 tumor cell lines. II-2 was also cytotoxic against the OVCAR-3 tumor cells. Formula II-17 was cytotoxic against MDA-MB-231, RPMI 8226, U266 and B16-F10 tumor cell lines. Formulae II-5A, II-5B and II-19 were cytotoxic against HT-29, PC-3, MDA-MB-231, RPMI 8226 and U266 tumor cells. Formula II-5A and II-19 were also cytotoxic against NCI-H292 tumor cells.

The data in Table 15 summarize the growth inhibitory effects of Formulae II-2, II-3, II-4, II-5A, II-5B, II-8C, II-13C, II-16, II-17, II-18, II-19, IV-3C and Formula II-20 against the human multiple myeloma cell lines, RPMI 8226 and U266.

The $EC_{50}$ values indicate that Formulae II-2, II-4, II-5A, II-5B, II-16, II-17, II-18, II-19 and II-20 were cytotoxic against RPMI 8226 and U266 cells. Formula IV-3C was cytotoxic against U266 cells Example 42

Growth Inhibition of MES-SA, MES-SA/Dx5, HL-60 and HL-60/MX2 Tumor Cell Lines

Human uterine sarcoma (MES-SA; CRL-1976), its multidrug resistant derivative (MES-SA/Dx5; CRL-1977), human acute promyelocytic leukemia cells (HL-60; CCL-240) and its multidrug resistant derivative (HL-60/MX2; CRL-2257) were purchased from ATCC and maintained in appropriate culture media. The cells were cultured in an incubator at 37° C. in 5% $CO_2$ and 95% humidified air.

For cell growth inhibition assays, MES-SA and MES-SA/Dx5 cells were both seeded at 3×10³ cells/well in 90 µl complete media into 96 well (Corning; 3904) black-walled, clear-bottom tissue culture plates and the plates were incubated overnight to allow cells to establish and enter log phase growth. HL-60 and HL-60/MX2 cells were both seeded at 5×10⁴ cells/well in 90 µl complete media into 96 well plates on the day of compound addition. 20 mM stock solutions of the compounds were prepared in 100% DMSO and stored at −80° C. The compounds were serially diluted and added in triplicate to the test wells. Concentrations ranging from 6.32 µM to 2 nM were tested for II-2 and II-4. II-3 and II-17 were tested at concentrations ranging from 20 µM to 6.32 nM. Compound II-18 was tested at concentrations ranging from 2 µM to 632 pM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an $EC_{50}$ value was not determined.

The multidrug resistant MES-SA/Dx5 tumor cell line was derived from the human uterine sarcoma MES-SA tumor cell line and expresses elevated P-Glycoprotein (P-gp), an ATP dependent efflux pump. The data in Table 16 summarize the growth inhibitory effects of Formulae II-2, II-3, II-4, II-17 and II-18 against MES-SA and its multidrug resistant derivative MES-SA/Dx5. Paclitaxel, a known substrate of the P-gp pump was included as a control.

TABLE 16

$EC_{50}$ values of Formulae II-2, II-3, II-4, II-17 and II-18 against MES-SA and MES-SA/Dx5 tumor cell lines

| Compound | $EC_{50}$ (nM) | | Fold |
|----------|--------|-----------|---------|
|          | MES-SA | MES-SA/Dx5 | change* |
| II-2     | 193    | 220       | 1.0     |
|          | 155    | 138       |         |
| II-3     | >20000 | >20000    | NA      |
|          | >20000 | >20000    |         |
| II-4     | 163    | 178       | 0.9     |
|          | 140    | 93        |         |
| II-17    | 9230   | 9450      | 0.8     |
|          | 12900  | 7530      |         |
| II-18    | 22     | 32        | 1.2     |
|          | 17     | 14        |         |
| Paclitaxel | 5.6  | 2930      | 798     |
|          | 4.6    | 5210      |         |

*Fold change = the ratio of $EC_{50}$ values (MES-SA/Dx5:MES-SA)

The $EC_{50}$ values indicate that II-2, II-4, II-17 and II-18 have cytotoxic activity against both MES-SA and MES-SA/Dx5 tumor cell lines. The multidrug resistant phenotype was confirmed by the observation that Paclitaxel was ~800 times less active against the resistant MES-SA/Dx5 cells.

HL-60/MX2 is a multidrug resistant tumor cell line derived from the human promyelocytic leukemia cell line, HL-60 and expresses reduced topoisomerase II activity. The data presented in Table 17 summarize the growth inhibitory effects of Formulae II-2, II-3, II-4, II-17 and II-18 against HL-60 and its multidrug resistant derivative HL-60/MX2. Mitoxantrone, the topoisomerase II targeting agent was included as a control.

TABLE 17

$EC_{50}$ values of Formulae II-2, II-3, II-4, II-17 and II-18 against HL-60 and HL-60/MX2 tumor cell lines

| Compound | $EC_{50}$ (nM) | | Fold |
|----------|-------|----------|---------|
|          | HL-60 | HL-60/MX2 | change* |
| II-2     | 237   | 142      | 0.7     |
|          | 176   | 133      |         |
| II-3     | >20000 | >20000  | NA      |
|          | >20000 | >20000  |         |
| II-4     | 143   | 103      | 0.8     |
|          | 111   | 97       |         |
| II-17    | >20000 | >20000  | NA      |
| II-18    | 27    | 19       | 0.7     |
|          | 23    | 18       |         |
| Mitoxantrone | 42 | 1340    | 30.6    |
|          | 40    | 1170     |         |

*Fold change = the ratio of $EC_{50}$ values (HL-60/MX2:HL-60)

The $EC_{50}$ values indicate that II-2, II-4 and II-18 retained cytotoxic activity against both HL-60 and HL-60/MX2 tumor cell lines. The multidrug resistant phenotype was confirmed by the observation that Mitoxantrone was ~30 times less active against the resistant HL-60/MX2 cells.

Example 43

Inhibition of NF-κB-Mediated Luciferase Activity; HEK293 NF-κB/Luciferase Reporter Cell Line The HEK293 NF-κB/luciferase reporter cell line is a derivative of the human embryonic kidney cell line (ATCC; CRL-1573) and carries a luciferase reporter gene under the regulation of 5×NF-κB binding sites. The reporter cell line was routinely maintained in complete DMEM medium (DMEM plus 10% (v/v) Fetal bovine serum, 2 mM L-glutamine, 10 mM HEPES and Penicillin/Streptomycin at 100 IU/ml and 100 µg/ml, respectively) supplemented with 250 µg/ml G418. When performing the luciferase assay, the DMEM basal medium was replaced with phenol-red free DMEM basal medium and the G418 was omitted. The cells were cultured in an incubator at 37° C. in 5% CO2 and 95% humidified air.

For NF-κB-mediated luciferase assays, HEK293 NF-κB/luciferase cells were seeded at 1.5×10⁴ cells/well in 90 µl phenol-red free DMEM complete medium into Corning 3917 white opaque-bottom tissue culture plates. For Formula II-2, Formula II-4 and Formula II-5A, a 400 µM starting dilution was made in 100% DMSO and this dilution was used to generate a 8-point half log dilution series. This dilution series was further diluted 40× in appropriate culture medium and ten µl aliquots were added to the test wells in triplicate resulting in final test concentrations ranging from 1 µM to 320 pM. For Formula II-3 and Formula II-5B, a 8 mM starting dilution was made in 100% DMSO and the same procedure was followed as described above resulting in final test concentrations ranging from 20 μM to 6.3 nM. The plates were returned to the incubator for 1 hour. After 1 hr pretreatment, 10 μl of a 50 ng/ml TNF-α solution, prepared in the phenol-red free DMEM medium was added, and the plates were incubated for an additional 6 hr. The final concentration of DMSO was 0.25% in all samples.

At the end of the TNF-α stimulation, 100 μl of Steady Lite HTS luciferase reagent (Packard Bioscience) was added to each well and the plates were left undisturbed for 10 min at room temperature before measuring the luciferase activity. The relative luciferase units (RLU) were measured by using a Fusion microplate fluorometer (Packard Bioscience). The $EC_{50}$ values (the drug concentration at which 50% of the maximal relative luciferase unit inhibition is established) were calculated in Prism (GraphPad Software) using a sigmoidal dose response, variable slope model.

NF-κB regulates the expression of a large number of genes important in inflammation, apoptosis, tumorigenesis, and autoimmune diseases. Thus compounds capable of modulating or affecting NF-κB activity are useful in treating diseases related to inflammation, cancer, and autoimmune diseases, for example. In its inactive form, NF-κB complexes with IκB in the cytosol and upon stimulation, IκB is phosphorylated, ubiquitinated and subsequently degraded by the proteasome. The degradation of IκB leads to the activation of NF-κB and its translocation to the nucleus. The effects of Formula II-2, Formula II-3, Formula II-4, Formula II-5A and Formula II-5B on the activation of NF-κB was evaluated by assessing the NF-κB-mediated luciferase activity in HEK293 NF-κB/ Luc cells upon TNF-α stimulation.

Figure 44:
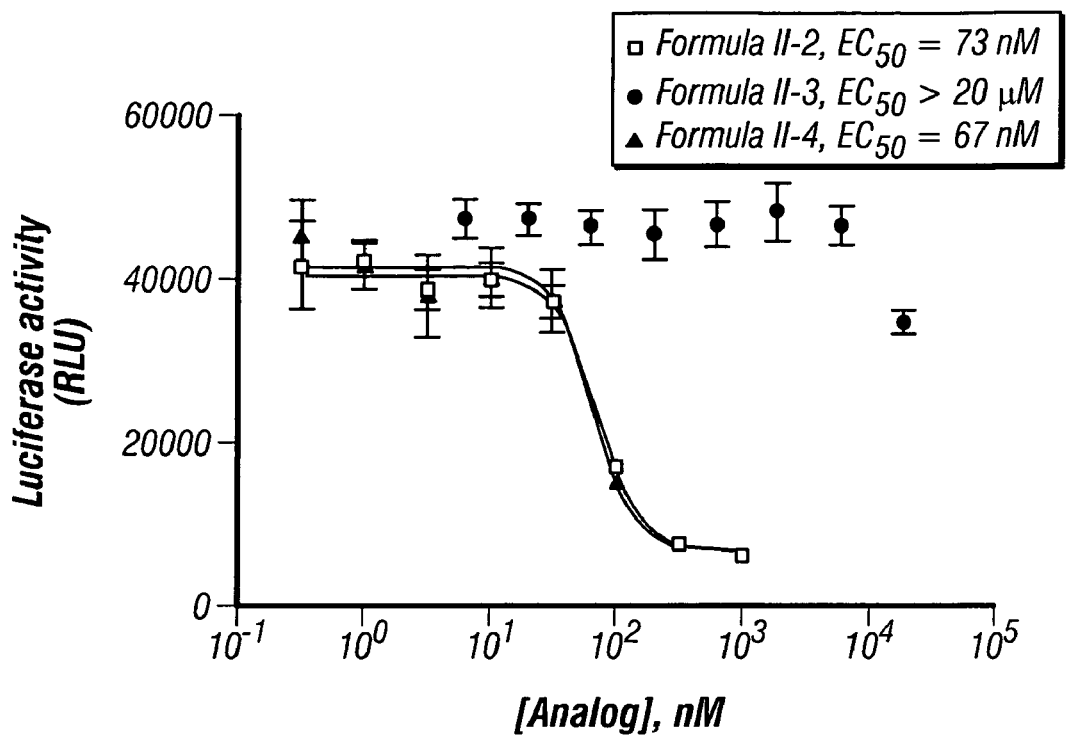
FIG. 44 depicts assay results showing the effect of Formula II-2, Formula II-3 and Formula II-4 on NF-κB mediated luciferase activity in HEK293 NF-κB/Luc Cells.

Results from a representative experiment evaluating Formula II-2, Formula II-3 and Formula II-4 (FIG. 44) revealed that pretreatment with Formula II-2 and Formula II-4 resulted in a dose-dependent decrease of luciferase activity in NF-κB/ Luc 293 cells upon TNF-α stimulation. The calculated $EC_{50}$ to inhibit NF-κB inducible luciferase activity in this experiment was 73 nM for Formula II-2, while $EC_{50}$ value for Formula II-4 was 67 nM. Similar data were observed in a replicate experiment.

Figure 45:
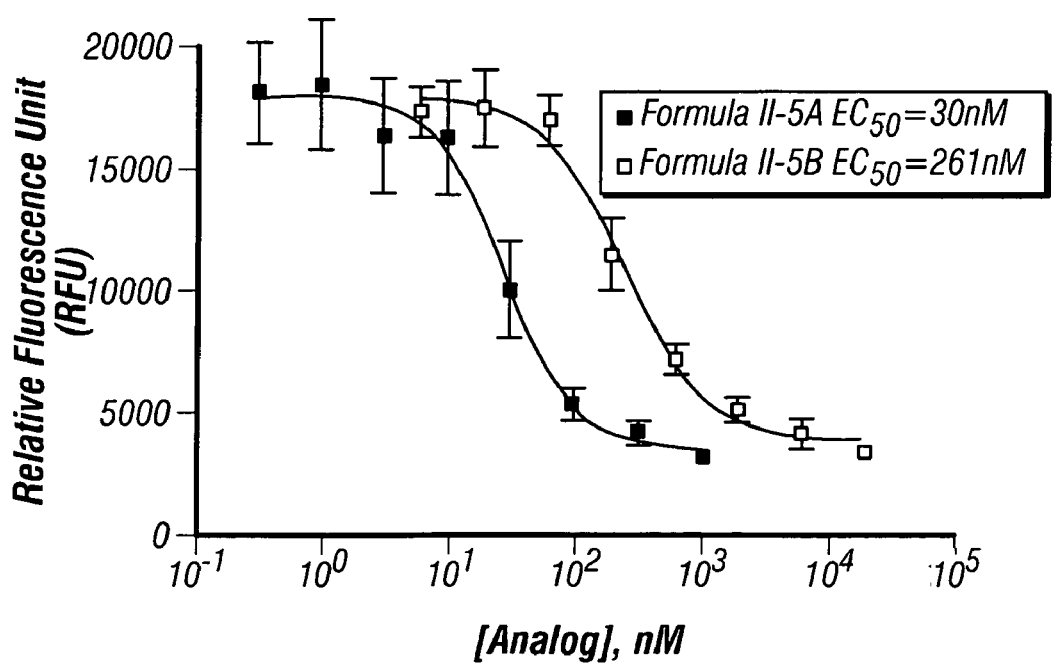
FIG. 45 depicts assay results showing the effect of Formula II-5A and Formula II-5B on NF-κB mediated luciferase activity in HEK293 NF-κB/Luc Cells

Results from a representative experiment evaluating Formula II-5A and Formula II-5B are shown in FIG. 45 and illustrate that Formula II-5A and Formula II-5B inhibit NF-κB inducible luciferase activity with $EC_{50}$ values of 30 nM and 261 nM respectively. Similar data were observed in a replicate experiment.

Example 44

In Vitro Inhibition of Proteasome Activity by Formula II-2, Formula II-3, Formula II-4, Formula II-5A and Formula II-5B Formula II-2, Formula II-3, Formula II-4, Formula II-5A and Formula II-5B were prepared as 20 mM stock solution in DMSO and stored in small aliquots at −80° C. Purified rabbit muscle 20S proteasome was obtained from CalBiochem. To enhance the chymotrypsin-like activity of the proteasome, the assay buffer (20 mM HEPES, pH7.3, 0.5 mM EDTA, and 0.05% Triton X100) was supplemented with SDS resulting in a final SDS concentration of 0.035%. The substrate used was sucLLVY-AMC, a fluorogenic peptide substrate specifically cleaved by the chymotrypsin-like activity of the proteasome. Assays were performed at a proteasome concentration of 1 μg/ml in a final volume of 200 μl in 96-well Costar microtiter plates. Formula II-2 and Formula II-4 were tested as eight-point dose response curves with final concentrations ranging from 500 nM to 0.16 nM, while Formula II-3 was tested with final concentrations ranging from 10 μM to 3.2 nM. Formula II-5A and Formula II-5B were tested with final concentrations ranging from 1 μM to 0.32 nM. The samples were incubated at 37° C. for five minutes in a temperature controlled plate reader. During the preincubation step, the substrate was diluted 25-fold in assay buffer supplemented with 0.035% SDS. After the preincubation period, the reactions were initiated by the addition of 10 μl of the diluted substrate and the plates were returned to the plate reader. The final concentration of substrate in the reactions was 20 μM. All data were collected every five minutes for more than 1.5 hour and plotted as the mean of triplicate data points. The $EC_{50}$ values (the drug concentration at which 50% of the maximal relative fluorescence unit is inhibited) were calculated by Prism (GraphPad Software) using a sigmoidal dose-response, variable slope model.

Figure 46:
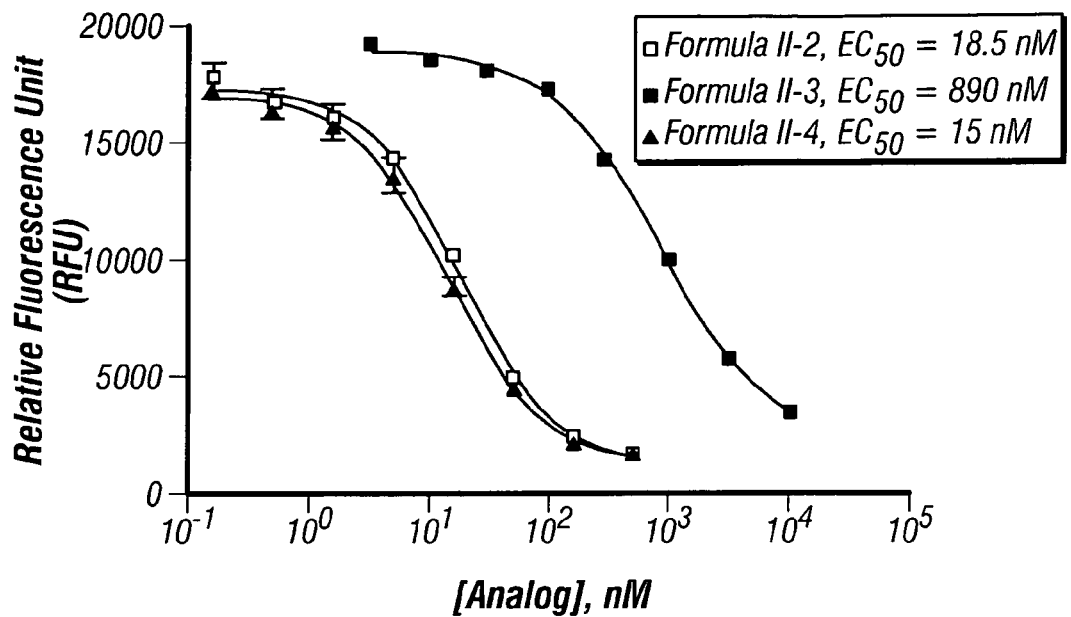
FIG. 46 depicts assay results showing the effect of Formula II-2, Formula II-3, and Formula II-4 on the chymotrypsin-like activity of rabbit 20S proteasome.

Results from a representative experiment evaluating Formula II-2, Formula II-3 and Formula II-4 are shown in FIG. 46 and illustrate that Formula II-2 and Formula II-4 inhibit the chymotrypsin-like activity of the proteasome with $EC_{50}$ values of 18.5 nM and 15 nM respectively. Formula II-3 is active in this assay with an $EC_{50}$ value of 890 nM. Similar results were obtained from an independent experiment.

Figure 47:
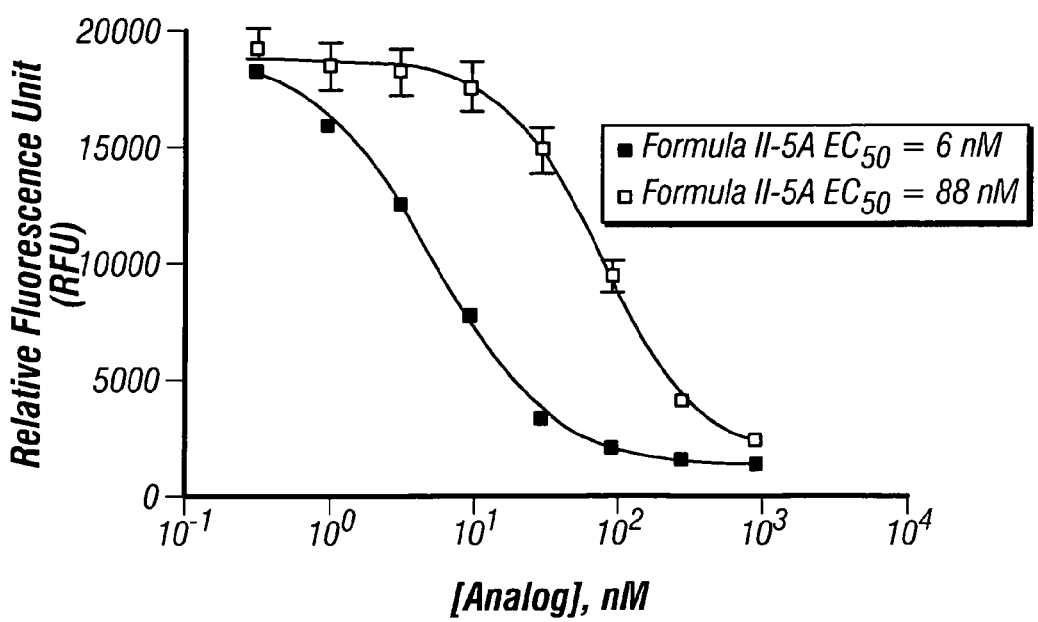
FIG. 47 depicts the effect of Formula II-5A and Formula II-5B on the chymotrypsin-like activity of rabbit 20S proteasome.

Results from a representative experiment evaluating Formula II-5A and Formula II-5B are shown in FIG. 47 and illustrate that Formula II-5A and Formula II-5B inhibit the chymotrypsin-like activity of the proteasome with $EC_{50}$ values of 6 nM and 88 nM respectively. Similar results were obtained in an independent experiment.

Example 45

Inhibition of Anthrax Lethal Toxin

Anthrax toxin is responsible for the symptoms associated with anthrax. In this disease, *B. anthracis* spores are inhaled and lodge in the lungs where they are ingested by macrophages. Within the macrophage, spores germinate, replicate, resulting in killing of the cell. Before killing occurs, however, infected macrophages migrate to the lymph nodes where, upon death, they release their contents, allowing the organism to enter the bloodstream, further replicate, and secrete lethal toxins.

Two proteins called protective antigen (PA 83 kDa) and lethal factor (LF, 90 kDa), play a key role in the pathogenesis of anthrax. These proteins are collectively known as lethal toxin (LeTx). When combined, PA and LF cause death when injected intravenously in animals. Lethal toxin is also active in a few cell culture lines of macrophages causing cell death within a few hours. LeTx can induce both necrosis and apoptosis in mouse macrophage-like RAW264.7 cells upon in vitro treatment.

In Vitro Cell-Based Assay for Inhibitors of Lethal Toxin-Mediated Cytotoxicity

RAW264.7 cells (obtained from the American Type Culture Collection) were adapted to and maintained in RPMI-1640 medium supplemented with 10% fetal bovine serum, 2 mM L-glutamine and 1% Penicillin/Streptomycin (complete medium) at 37° C. in a humidified 5% $CO_2$ incubator. For the assay, cells were plated overnight in complete medium at a concentration of 50,000 cells/well in a 96-well plate. Media was removed the following day and replaced with serum-free complete medium with or without varying concentrations of Formulae II-2, II-3, II-4, II-5A, II-5B, II-13C, II-17, II-18 and IV-3C starting at 330 nM and diluting at ½ log intervals for an 8-point dose-response. After a 45 minute preincubation, 1 μg/ml LF and 1 μg/ml PA alone or in combination (LF:PA, also termed lethal toxin (LeTx)) were added to cells. Recombinant LF and PA were obtained from List Biological Laboratories. Additional plates with no LeTx added were included as a control. Cells were then incubated for six hours followed by addition of 0.02 mg/ml resazurin dye (Molecular Probes, Eugene, Oreg.) prepared in Mg++, Ca++ free PBS (Mediatech, Herndon, Va.). Plates were then incubated an additional 1.5 hours prior to the assessment of cell viability. Since resazurin is metabolized by living cells, cytotoxicity or cell viability can be assessed by measuring fluorescence using 530 excitation and 590 emission filters. Data are expressed as the percent viability as compared to a DMSO alone control (high) and the LeTx alone control (low) using the following equation: Percent viability=100*((Measured OD-low control)/(high control-low control)).

Inhibition of Anthrax Lethal Toxin-Mediated Cytotoxicity in RAW 264.7 Cells

Data in FIG. 48 summarize the effects of Formula II-2, Formula II-3 and Formula II-4 against LeTx-mediated cytotoxicity of the RAW 264.7 murine macrophage-like cell line. Treatment of RAW 264.7 cells with Formula II-2 and Formula II-4 resulted in an increase in the viability of LeTx treated cells with $EC_{50}$ values of 14 nM (FIG. 48). The $EC_{50}$ values for Formula II-3 for LeTx protection was not be determined at the concentrations tested ($EC_{50}$>330 nM, the maximum concentration evaluated). Data in Table 18 show the effects of Formulae II-5A, II-5B, II-13C, II-17, II-18 and IV-3C against LeTx-mediated cytotoxicity of the RAW 264.7 murine macrophage-like cell line. Treatment of RAW 264.7 cells with Formula II-5A and II-18 showed an increase in the viability of LeTx treated RAW 264.7 cells with $EC_{50}$ values of 3 nM and 4 nM respectively. Treatment with Formula II-17 and Formula II-5B resulted in an increase in the viability of LeTx treated cells with $EC_{50}$ values of 42 nM and 45 nM respectively. The $EC_{50}$ values for Formulae II-13C and IV-3C for LeTx protection could not be determined at the concentrations tested ($EC_{50}$>330 nM, the maximum concentration evaluated).

TABLE 18

$EC_{50}$ values for inhibition of RAW 264.7 cell cytotoxicity mediated by anthrax lethal toxin

| Compound | $EC_{50}$ (nM) |
| --- | --- |
| Formula II-17 | 42 |
| Formula II-18 | 4 |
| Formula II-5A | 3 |
| Formula II-5B | 45 |
| Formula II-13C | >330 nM |
| Formula IV-3C | >330 nM |

Example 46

Formulation to be Administered Orally or the Like

A mixture obtained by thoroughly blending 1 g of a compound obtained and purified by the method of the embodiment, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

The examples described above are set forth solely to assist in the understanding of the embodiments. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the embodiments disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention, which is limited only by the following claims.

What is claimed is:

1. A method of treating a neoplastic disease in an animal, the method consisting essentially of administering alone to the animal, a therapeutically effective amount of a compound, and pharmaceutically acceptable salts and pro-drug esters thereof, wherein the compound has the structure:

wherein:
the neoplastic disease is a cancer selected from the group consisting of angiosarcoma; sinus cancer; esophageal cancer; uretal cancer; liver cancer; and angioma.
2. The method of claim 1, wherein the animal is a mammal.
3. The method of claim 1, wherein the animal is a human.

4. The method of claim 1, wherein the animal is a rodent.

5. The method of claim 1, further comprising identifying an animal that would benefit from administration of the compound, and pharmaceutically acceptable salts and pro-drug esters thereof.

6. A method of inhibiting the growth of a cancer cell, consisting essentially of contacting a cancer cell alone with a compound, and pharmaceutically acceptable salts and pro-drug esters thereof, wherein the compound has the structure:

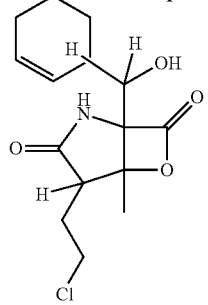

wherein:
the cancer cell is selected from the group consisting of angiosarcoma cell; sinus cancer cell; esophageal cancer cell; uretal cancer cell; liver cancer cell; and angioma cell.

7. A method of inhibiting proteasome activity consisting essentially of the step contacting a cell alone with a compound, and pharmaceutically acceptable salts and pro-drug esters thereof, wherein the compound has the structure:

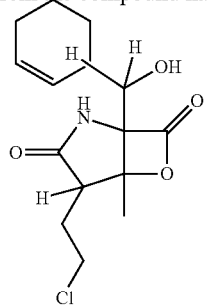

wherein:
the cell is a cancer cell selected from the group consisting of angiosarcoma cell; sinus cancer cell; esophageal cancer cell; uretal cancer cell; liver cancer cell; and angioma cell.

8. A method of inhibiting NF-κB activation consisting essentially of the step contacting a cell alone with a compound, and pharmaceutically acceptable salts and pro-drug esters thereof, wherein the compound the structure:

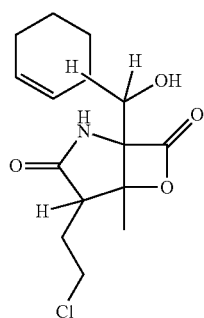

wherein:
the cell is a cancer cell selected from the group consisting of angiosarcoma cell; sinus cancer cell; esophageal cancer cell; uretal cancer cell; liver cancer cell; and angioma cell.

9. A method for treating an inflammatory condition, comprising administering an effective amount of a compound to a patient in need thereof, wherein the compound has the structure:

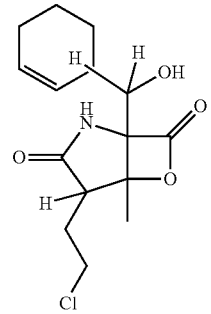

wherein:
the inflammatory condition is selected from the group consisting of ischemia, septic shock, autoimmune diseases, rheumatoid arthritis, inflammatory bowel disease, systemic lupus eythematosus, multiple sclerosis, asthma, osteoarthritis, osteoporosis, fibrotic diseases, dermatosis, psoriasis, atopic dermatitis, ultraviolet radiation (UV)-induced skin damage, psoriatic arthritis, alkylosing spondylitis, tissue rejection, organ rejection, Alzheimer's disease, stroke, atherosclerosis, restenosis, diabetes, glomerulonephritis, cachexia, inflammation associated with an infection, inflammation associated with acquired immune deficiency syndrome (AIDS), inflammation associated with adult respiratory distress syndrome and inflammation associated with Ataxia Telangiestasia.

10. The method of claim 9, wherein the inflammatory condition is selected from the group consisting of rheumatoid arthritis, asthma, multiple sclerosis, psoriasis, stroke, tissue rejection, and organ rejection.

11. A method for treating a microbial illness comprising administering an effective amount of a compound to a patient in need thereof, wherein the compound has the structure:

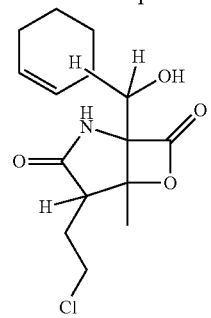

wherein:
the microbial illness is caused by a microbe selected from the group consisting of *B. anthracis, Plasmodium, Leishmania,* and *Trypanosoma*.

12. The method of claim 9, wherein the inflammatory condition is selected from tissue rejection and organ rejection.

* * * * *

UNITED STATES PATENT AND TRADEMARK OFFICE
CERTIFICATE OF CORRECTION

PATENT NO. : 8,168,803 B2
APPLICATION NO. : 12/136688
DATED : May 1, 2012
INVENTOR(S) : Palladino et al.

It is certified that error appears in the above-identified patent and that said Letters Patent is hereby corrected as shown below:

Column 3, Line 33, Change "aminocarboyloxy," to --aminocarbonylox y,--.

Column 3, Lines 45-46, Change "aminocarboyloxy," to --aminocarbonyloxy,--.

Column 3, Line 56, Change "aminocarboyloxy," to --aminocarbonyloxy,--.

Column 7, Line 1, Change "aminocarboyloxy," to --aminocarbonyloxy,--.

Column 11, Lines 19-20, Change "aminocarboyloxy," to --aminocarbonyloxy,--.

Column 24, Lines 19-20, Change "aminocarboyloxy," to --aminocarbonyloxy,--.

Column 24, Line 30, Change "aminocarboyloxy," to --aminocarbonyloxy,--.

Column 24, Lines 63-64, Change "aminocarboyloxy," to --aminocarbonyloxy,--.

Column 25, Line 39, Change "aminocarboyloxy," to --aminocarbonyloxy,--.

Column 28, Line 21, Change "aminocarboyloxy," to --aminocarbonyloxy,--.

Column 28, Line 44, Change "pivoyloxymethyl," to --pivaloyloxymethyl,--.

Column 29, Line 13, Change "p-toluensulfonic" to --p-toluenesulfonic--.

Column 33, Line 46, Change "cotttonseed" to --cottonseed--.

Column 34, Line 8, Change "know" to --known--.

Column 34, Line 22, Change "μM" to --pM--.

Column 45, Line 29, Change "gouadotropin" to --gonadotropin--.

Column 45, Line 36, Change "Caminomycin," to --Carminomycin,--.

Column 45, Line 60, Change "eythematosus," to --erythematosus,--.

Column 45, Line 63, Change "alkylosing" to --ankylosing--.

Column 46, Line 2, Change "Telangiestasia." to --Telangiectasia.--.

Column 52, Line 52, Change "acatete" to --acetate--.

Column 53, Line 55, Change "mix-13" to --mix-β--.

Column 92, Line 57, Change "204" to --2 μM--.

Signed and Sealed this
Twenty-seventh Day of November, 2012

David J. Kappos
*Director of the United States Patent and Trademark Office*

Column 101, Line 51, In Claim 8, after "compound" insert --has--.

Column 102, Line 26, In Claim 9, change "eythematosus," to --erythematosus,--.

Column 102, Lines 29-30, In Claim 9, change "alkylosing" to --ankylosing--.

Column 102, Line 37, In Claim 9, change "Telangiestasia." to --Telangiectasia.--.